United States Patent
Vogelstein et al.

(10) Patent No.: US 9,695,479 B2
(45) Date of Patent: Jul. 4, 2017

(54) MEDULLOBLASTOMA GENES AS TARGETS FOR DIAGNOSIS AND THERAPEUTICS

(75) Inventors: Bert Vogelstein, Baltimore, MD (US); Kenneth Kinzler, Baltimore, MD (US); Nickolas Papadopoulos, Towson, MD (US); Donald Williams Parsons, Ellicott City, MD (US); Rebecca J. Leary, Baltimore, MD (US); Meng Li, Baltimore, MD (US); Xiaosong Zhang, Baltimore, MD (US); Sian Jones, Baltimore, MD (US); Gregory J. Riggins, Baltimore, MD (US); Victor Velculescu, Dayton, MD (US); Darell Bigner, Mebane, NC (US); Hai Yan, Chapel Hill, NC (US)

(73) Assignees: The Johns Hopkins University, Baltimore, MD (US); Duke University, Durham, NC (US)

( * ) Notice: Subject to any disclaimer, the term of this patent is extended or adjusted under 35 U.S.C. 154(b) by 541 days.

(21) Appl. No.: 13/884,154

(22) PCT Filed: Nov. 8, 2011

(86) PCT No.: PCT/US2011/059751
§ 371 (c)(1),
(2), (4) Date: Jul. 22, 2013

(87) PCT Pub. No.: WO2012/064721
PCT Pub. Date: May 18, 2012

(65) Prior Publication Data
US 2013/0296408 A1    Nov. 7, 2013

Related U.S. Application Data

(60) Provisional application No. 61/411,332, filed on Nov. 8, 2010.

(51) Int. Cl.
*C12Q 1/68* (2006.01)
*G01N 33/574* (2006.01)

(52) U.S. Cl.
CPC ..... *C12Q 1/6886* (2013.01); *G01N 33/57407* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS 6,326,163 B1 * 12/2001 Forssmann ........ G01N 33/6818
435/24

OTHER PUBLICATIONS

Balakrishnan et al. Cancer Research (2007) 67:3545-3550.*
(Continued)

*Primary Examiner* — Joseph G Dauner
(74) *Attorney, Agent, or Firm* — Banner & Witcoff, Ltd.

(57) ABSTRACT

Medulloblastoma (MB) is the most common malignant brain tumor of children. To identify the genetic alterations in this tumor type, we searched for copy number alterations using high density microarrays and sequenced all known protein-coding genes and miRNA genes using Sanger sequencing. We found that, on average, each tumor had 11 gene alterations, markedly fewer than in common adult cancers. In addition to alterations in the Hedgehog and Wnt pathways, our analysis led to the discovery of genes not previously known to be altered in MBs. Most notably, inactivating mutations of the histone H3K4 trimethylase genes MLL2 or MLL3 were identified in 16% of MB patients. These results demonstrate key differences between the genetic landscapes of adult and childhood cancers, highlight dysregulation of developmental pathways as an important mechanism underlying MBs, and identify a role for a specific type of histone methylation in human tumorigenesis.

17 Claims, 51 Drawing Sheets

MLL2

MLL3

(56) References Cited

OTHER PUBLICATIONS

Guran et al. Cancer Genetics and Cytogenetics. 1999. 113(2): 145-151.*
Scott et al. Nature Clinical Practice. 2007. 4(2): 130-134.*
Zhu et al. Proceedings of the 2009 2nd International Conference on Biomedical Engineering and Informatics. Oct. 17-19, 2009.*
GeneCard. Retrieved on Oct. 29, 2015 from the internet: www.genecards.org.*
Li. From Cancer genetics to noninvasive molecular diagnostics. Oct. 2010. Dissertation, Johns Hopkins University.*
Supporting material at Science Online. Retrieved on Jun. 30, 2016 from the internet: http://science.sciencemag.org/content/331/6016/435.figures-only.*
Ng et al. Nature Genetics. 2010. 42:790-793.*
Parsons et al. Science 2008. 321(5897):1807-1812.*

* cited by examiner table S1. Primers used for PCR amplification and sequencing*

| Gene Symbol | Gene ID | Transcript ID | Coding Exon Number | Genomic Region of Interest | Forward primer sequence | Reverse primer sequence | High Quality Sequence |
|---|---|---|---|---|---|---|---|
| A1BG | ENSG00000121410 | ENST00000263100 | 1 | chr19:63556578-63556619 | M13-CTCAGAAGTTCACCGTTTGCC | TATGGGTGCTTGTGTCACTGG | Yes |
| A1BG | ENSG00000121410 | ENST00000263100 | 2 | chr19:63556466-63556309 | M13-GAAGGACAAACACAGGGAAGAG | TGGGTGTCATAAACTGGAAGG | Yes |
| A1BG | ENSG00000121410 | ENST00000263100 | 3 | chr19:63556102-63556379 | M13-GGTGACTTGGACGAAGGGAG | GTGAGGTCTGCGGAATGGTGG | Yes |
| A1BG | ENSG00000121410 | ENST00000263100 | 4 | chr19:63555457-63555737 | M13-CTCATGCCTGTCCTTCAC | TCAGGATGAATGTGTGTCATGC | Yes |
| A1BG | ENSG00000121410 | ENST00000263100 | 5 | chr19:63554366-63554969 | M13-GAAGGGGTGTTGCTGGGATTG | AAAGTTGGTATTGGAGGGTGG | Yes |
| A1BG | ENSG00000121410 | ENST00000263100 | 6 | chr19:63553644-63553833 | M13-GACGCCCAAGGAAAGAGG | AGACTGAGCCAAGGCAAAGAG | Yes |
| A1BG | ENSG00000121410 | ENST00000263100 | 7 | chr19:63553527-63550822 | M13-AGGGGAAGATGAAGCCGGG | GACCCAGGCGGTAACCAGG | Yes |
| A1BG | ENSG00000121410 | ENST00000263100 | 8 | chr19:63550196-63550211 | M13-GATTGGGTGAGGAGGAG | AGCCATCCACTTGAGGACAC | No |
| A1CF | ENSG00000148584 | ENST00000282641 | 3 | chr10:52289064-52289710 | M13-CACGAAATGTTCGAATTCCTTCTC | AAGACGACATTTACACACCCTTG | Yes |
| A1CF | ENSG00000148584 | ENST00000282641 | 10 | chr10:52243619-52243802 | M13-AATCAACGTTGAGTTGGGCTAAC | CCCAGCATTCCTTCAAAGAC | Yes |
| A1CF | ENSG00000148584 | ENST00000396439 | 1 | chr10:52280427-52280557 | M13-AAAGCTCCAAACGGATTAAGG | GGATTATTCAGTATCAAGCTTGAAG | Yes |
| A1CF | ENSG00000148584 | ENST00000396439 | 2 | chr10:52273756-52273892 | M13-AAGCTGCTGAAGACACAGAGTG | AACAGGCACTGACCAAGGAGG | Yes |
| A1CF | ENSG00000148584 | ENST00000396439 | 3 | chr10:52271624-52271762 | M13-TGTATTTCATTCTTGGGTTGGC | GGGAAAGTTCAGAAAGGATTG | Yes |
| A1CF | ENSG00000148584 | ENST00000396439 | 4 | chr10:52263826-52260882 | M13-ATTTGGGCAGAGCCATAC | CAGGAAATGGAATCAACTGTG | Yes |
| A1CF | ENSG00000148584 | ENST00000396439 | 5 | chr10:52257863-52258065 | M13-CATTGAAGCAGCCTCAAGGGTCA | TTCCTGACACATACACCCTC | Yes |
| A1CF | ENSG00000148584 | ENST00000396439 | 6 | chr10:52250014-52250419 | M13-AGAAGGCTGGAGTGGACAGG | TTCCACCCCTAGACACCTTG | Yes |
| A1CF | ENSG00000148584 | ENST00000396439 | 7 | chr10:52245768-52246040 | M13-AAGTGGACGACAGCATGAATGATC | TGTATTAGGGCTGAGGACAC | Yes |
| A1CF | ENSG00000148584 | ENST00000396439 | 9 | chr10:52240862-52240946 | M13-GGCACATCCAACTACACATC | TGAGTCATTAAATCATGTGGCA | Yes |
| A1CF | ENSG00000148584 | ENST00000396439 | 10 | chr10:52239666-52239812 | M13-TGTCCAGGAATGTCATCAAC | CAAACATTTCTGTATTCAATGG | Yes |
| A1CF | ENSG00000148584 | ENST00000396439 | 11 | chr10:52236641-52236653 | M13-TGATTCTGACACAAGGTGGTTG | TGTGGAAAGCATTTCTTTAGG | Yes |
| A2LD1 | ENSG00000134897 | ENST00000378250 | 3 | chr19:99982591-99982639 | M13-GGATGGGCCTAGTGTTCGTG | TGAAAGATTGGTTCGTTCGGG | Yes |
| A2LD1 | ENSG00000134894 | ENST00000357259 | 3 | NULL:99982590-99982850 | M13-CAGACACAGAGCTTCCCACTG | CTCTGAAACCTAGGCCCACC | Yes |

| Gene | Ensembl Gene ID | Transcript ID | Region | Coordinates | Forward Primer | Reverse Primer | Sequenced |
|---|---|---|---|---|---|---|---|
| A2M | ENSG00000175899 | ENST00000404465 | 36 | chr12:9111682-9111736 | M13-TTGAATGAACAGGAAACAGGG | GATTGCTTATGGGTAATGATTTGG | Yes |
| A2ML1 | ENSG00000166535 | ENST00000031537 | 1 | chr12:8866511-8866680 | M13-CACAGTCCTCCTGTGTTCCAG | GCTTCCTCTTCATGCGTCAG | Yes |
| A2ML1 | ENSG00000166535 | ENST00000031537 | 2 | chr12:8867041-8867232 | M13-TTCACTGCTACTTGCTGAGCG | AACCGTGGGTGAGTTATAGCC | Yes |
| A2ML1 | ENSG00000166535 | ENST00000031537 | 3 | chr12:8867579-8867749 | M13-TCACTGTTGGGTTGAGACCAG | TGTAGCCAGCATGTATTCAAC | Yes |
| A2ML1 | ENSG00000166535 | ENST00000031537 | 7 | chr12:8880114-8880206 | M13-TTTGAATCGATGCTGAACCAG | CCACTCCCATGTCATCCC | Yes |
| A2ML1 | ENSG00000166535 | ENST00000031537 | 8 | chr12:8881299-8881433 | M13-GCTTTCTTTCAGAGGCTGGAG | CTCGTGATCCGCCCATCT | Yes |
| A2ML1 | ENSG00000166535 | ENST00000031537 | 9 | chr12:8882195-8882317 | M13-TTGGAGTAAATCTGTCCCTGG | CCTTTCCCAAATCTTGGAGC | Yes |
| A2ML1 | ENSG00000166535 | ENST00000031537 | 10 | chr12:8882972-8883089 | M13-GAGGTTGGTTTGGATCTTTGG | TAGCTATGTGGCTATGGCTGC | Yes |
| A2ML1 | ENSG00000166535 | ENST00000031537 | 11 | chr12:8885226-8885403 | M13-AGTTTGCACCAACCTAATATTCAC | GGGAGAGCAGGAGTTGTGAG | Yes |
| A2ML1 | ENSG00000166535 | ENST00000031537 | 12 | chr12:8886363-8887226 | M13-GCAATTCAGATAGCCTAGGTGC | AACCGTAACAAGTCCGTGGG | Yes |

When a gene gives rise to multiple transcripts, the primers for shared exons are listed under only one transcript entry. Coding exons larger than 350 bp were amplified and sequenced with multiple primer pairs.

†Gene symbol indicates the approved gene symbol. Approved gene symbols were not available for all genes.

‡Gene ID is a unique number assigned to all transcripts from a given gene as described in the methods.

§Transcript accession ID for the transcript sequenced as described in the methods.

**Region of Interest designates the regions scored for mutations which included the protein encoding portions of gene plus 4 base pairs flanking each exon as well as 4 base pairs flanking the start and stop codons.

§§M13 denotes the universal sequencing primer: 5'-GTAAAACGACGGCCAGT-3'.

††Yes indicates that the primer pair gave high quality sequence in 18 or more of the 24 samples sequenced in the discovery screen.

Note: This is only one page showing 67 primer pairs from the 228,907 primer pairs in the full table.

FIG. 4D table S2. Characteristics of medulloblastoma samples used in Discovery and Prevalence Screens

| Tumor ID | Sample type | Screen | Patient age (years)* | Sex | Pathology by institutional report | Central pathologic review performed | Pathology on central review | MB subtype on central review | Recurrent MB# | Percent tumor nuclei | Race/Ethnicity | Extent of resection total or near-total (<1.5 cm2 residual tumor) | Evidence of leptomeningeal dissemination on MRI at initial diagnosis |
|---|---|---|---|---|---|---|---|---|---|---|---|---|---|
| MB101X | Xenograft | Discovery | 5 | M | MB | Yes | MB | C | No | >80 | White | Yes | No |
| MB104X | Xenograft | Discovery | 8 | F | MB | Yes | MB | C | No | >80 | White | Yes | Yes |
| MB105X | Xenograft | Discovery | 2 | M | MB | Yes | MB | C | No | >80 | White | Yes | No |
| MB106X | Xenograft | Discovery | 16 | M | MB | No | NA | NA | Yes | NA | White | Yes | No |
| MB108C | Cell line | Discovery | Unknown | Unknown | MB | No | NA | NA | Unknown | NA | Unknown | Unknown | Unknown |
| MB109PT | Primary tumor | Discovery | 3 | M | MB | Yes | MB | C | No | >80 | White | Yes | No |
| MB111PT | Primary tumor | Discovery | 5 | M | MB | Yes | MB | C | No | >80 | White | Yes | No |
| MB113PT | Primary tumor | Discovery | 8 | F | MB | Yes | MB | C | No | >80 | White | Yes | Yes |
| MB115PT | Primary tumor | Discovery | 5 | M | MB | Yes | MB | C | No | >80 | White | Yes | No |
| MB117PT | Primary tumor | Discovery | 2 | M | MB | Yes | MB | ND | No | >80 | Hispanic or Latino | Yes | No |
| MB118PT | Primary tumor | Discovery | 9 | F | MB | Yes | MB | C | No | >80 | Pacific Islander | Yes | No |
| MB119PT | Primary tumor | Discovery | 5 | M | MB | Yes | MB | LCA | No | >80 | White | Yes | No |
| MB120PT | Primary tumor | Discovery | 3 | M | MB | Yes | MB | C | No | 50 | White | Yes | No |
| MB121PT | Primary tumor | Discovery | 2 | M | MB | Yes | MB | C | No | >80 | White | Yes | No |

TO FIG. 5A-2
FIG. 5A-1

FROM FIG. 5A-1

| | | | | | | | | | | | |
|---|---|---|---|---|---|---|---|---|---|---|---|
| MB122PT | Primary tumor | Discovery | 13 | M | MB | Yes | MB | LCA | No | >80 | White | Yes | No |
| MB123PT | Primary tumor | Discovery | 4 | M | MB | Yes | MB | C | No | >80 | White | No | Yes |
| MB124PT | Primary tumor | Discovery | 9 | M | MB | Yes | MB | LCA | No | >80 | Hispanic or Latino | Yes | Yes |
| MB125PT | Primary tumor | Discovery | 11 | F | MB | Yes | MB | C | No | >80 | White | Yes | No |
| MB126PT | Primary tumor | Discovery | 11 | M | MB | Yes | MB | LCA | No | 70 | White | Yes | No |
| MB128PT | Primary tumor | Discovery | 6 | M | MB | Yes | MB | C | No | >80 | White | Unknown | Yes |
| MB129PT | Primary tumor | Discovery | Unknown | Unknown | MB | No | N/A | N/A | Unknown | N/A | Unknown | Unknown | Unknown |
| MB130PT | Primary tumor | Discovery | Unknown | Unknown | MB | No | N/A | N/A | Unknown | N/A | Unknown | Unknown | Unknown |
| MB107PT | Primary tumor | Prevalence | 16 | M | MB | Yes | MB | C | Yes | 70 | White | Yes | No |
| MB110PT | Primary tumor | Prevalence | 10 | M | MB | No | N/A | N/A | No | N/A | White | Yes | No |
| MB112PT | Primary tumor | Prevalence | 7 | M | MB | No | N/A | N/A | No | N/A | White | Yes | No |
| MB114PT | Primary tumor | Prevalence | 6 | M | MB | No | N/A | N/A | No | N/A | White | Yes | No |
| MB116PT | Primary tumor | Prevalence | 39 | M | MB | Yes | MB | C | Yes | <25 | White | Yes | No |
| MB127PT | Primary tumor | Prevalence | 10 | M | MB | No | N/A | N/A | No | N/A | White | Yes | No |
| MB131PT | Primary tumor | Prevalence | 4 | M | MB | Yes | MB | ND | No | >80 | Black | Yes | No |
| MB132PT | Primary tumor | Prevalence | Unknown | Unknown | MB | No | N/A | N/A | Unknown | N/A | Unknown | Unknown | Unknown |
| MB133PT | Primary tumor | Prevalence | Unknown | Unknown | MB | No | N/A | N/A | Unknown | N/A | Unknown | Unknown | Unknown |

FROM FIG. 5A-2

| | | | | | | | | | | | |
|---|---|---|---|---|---|---|---|---|---|---|---|
| MB134PT | Primary tumor | Prevalence | Unknown | Unknown | MB | No | NA | NA | Unknown | Unknown | Unknown | Unknown |
| MB135PT | Primary tumor | Prevalence | Unknown | Unknown | MB | No | NA | NA | Unknown | Unknown | Unknown | Unknown |
| MB157PT | Primary tumor | Prevalence | 10 | M | MB | No | NA | NA | Yes | NA | Asian | No |
| MB158PT | Primary tumor | Prevalence | 15 | F | MB | Yes | MB | ND | No | >80 | White | Yes | No |
| MB159PT | Primary tumor | Prevalence | 17 | F | MB | Yes | MB | C | No | >80 | White | Yes | No |
| MB160PT | Primary tumor | Prevalence | 6 | M | MB | Yes | MB | C | No | >80 | Asian | Yes | No |
| MB161PT | Primary tumor | Prevalence | 6 | F | MB | Yes | MB | C | No | >80 | White | Yes | No |
| MB162PT | Primary tumor | Prevalence | 7 | M | MB | No | NA | NA | No | NA | Black | Unknown | Unknown |
| MB163PT | Primary tumor | Prevalence | 11 | F | MB | No | NA | NA | No | NA | White | Yes | No |
| MB164PT | Primary tumor | Prevalence | 8 | M | MB | Yes | MB | C | No | >80 | White | Yes | No |
| MB201PT | Primary tumor | Prevalence | 9 | F | MB | Yes | MB | C | No | >80 | White | Yes | No |
| MB202PT | Primary tumor | Prevalence | 3 | F | MB | Yes | MB | C | No | >80 | White | Yes | Yes |
| MB203PT | Primary tumor | Prevalence | 1 | F | MB | Yes | MB | C | No | 70 | White | Yes | Yes |
| MB204PT | Primary tumor | Prevalence | 10 | F | MB | Yes | MB | C | No | >80 | White | No | Yes |
| MB205PT | Primary tumor | Prevalence | 11 | M | MB | Yes | MB | C | No | >80 | White | Yes | No |
| MB206PT | Primary tumor | Prevalence | Unknown | M | MB | Yes | MB | C | No | >80 | White | Yes | No |
| MB210PT | Primary tumor | Prevalence | 9 | M | MB | Yes | MB | C | No | >80 | Unknown | Yes | Yes |

FROM FIG. 5A-3

| | | | | | | | | | | |
|---|---|---|---|---|---|---|---|---|---|---|
| MB211PT | Primary tumor | Prevalence | 25 | F | MB | Yes | MB | C | Yes | >80 | Unknown | Yes | No |
| MB212PT | Primary tumor | Prevalence | 12 | F | MB | Yes | MB | C | No | >80 | Unknown | No | Yes |
| MB213PT | Primary tumor | Prevalence | 7 | M | MB | Yes | MB | C | No | >80 | Unknown | Yes | No |
| MB214PT | Primary tumor | Prevalence | 4 | F | MB | Yes | MB | C | No | 70 | Unknown | Yes | No |
| MB215PT | Primary tumor | Prevalence | 10 | M | MB | Yes | MB | LCA | No | >80 | Unknown | Yes | No |
| MB216PT | Primary tumor | Prevalence | 33 | F | MB | Yes | MB | LCA | No | >80 | Unknown | Yes | No |
| MB217PT | Primary tumor | Prevalence | 1 | F | MB | Yes | MB | C | No | >80 | Unknown | Yes | No |
| MB218PT | Primary tumor | Prevalence | 31 | M | MB | Yes | MB | C | No | 60 | Unknown | Yes | No |

FIG. 5A-4

| | | | | | | | | | | |
|---|---|---|---|---|---|---|---|---|---|---|
| MB219PT | Primary tumor | Prevalence | 25 | M | MB | Yes | MB | C | No | 60 | Unknown | Yes | No |
| MB220PT | Primary tumor | Prevalence | 7 | F | MB | Yes | MB | C | No | >80 | Unknown | No | No |
| MB221PT | Primary tumor | Prevalence | 33 | M | MB | Yes | MB | C | No | >80 | Unknown | Yes | No |
| MB222PT | Primary tumor | Prevalence | 14 | F | MB | Yes | MB | ND | No | 70 | Unknown | Yes | No |
| MB225PT | Primary tumor | Prevalence | 12 | M | MB | Yes | MB | C | No | >80 | Unknown | No | No |
| MB226PT | Primary tumor | Prevalence | 5 | M | MB | Yes | MB | C | No | >80 | Unknown | No | No |
| MB227PT | Primary tumor | Prevalence | 29 | M | MB | Yes | MB | LCA | No | >80 | Unknown | Yes | No |
| MB228PT | Primary tumor | Prevalence | 18 | F | MB | Yes | MB | C | Yes | >80 | Unknown | Yes | No |
| MB229PT | Primary tumor | Prevalence | 7 | M | MB | Yes | MB | ND | No | 70 | Unknown | No | No |
| MB230PT | Primary tumor | Prevalence | 33 | M | MB | Yes | MB | ND | No | >80 | Unknown | Yes | No |
| MB231PT | Primary tumor | Prevalence | 18 | M | MB | Yes | MB | ND | No | >80 | Unknown | Yes | No |
| MB232PT | Primary tumor | Prevalence | 18 | M | MB | Yes | MB | C | No | >80 | Unknown | Yes | No |
| MB233PT | Primary tumor | Prevalence | 32 | M | MB | Yes | MB | C | No | >80 | Unknown | Yes | No |
| MB234PT | Primary tumor | Prevalence | 23 | M | MB | Yes | MB | C | No | >80 | Unknown | Yes | No |
| MB235PT | Primary tumor | Prevalence | Unknown | M | MB | Yes | MB | C | No | >80 | Unknown | No | Yes |
| MB236PT | Primary tumor | Prevalence | 3 | M | MB | Yes | MB | C | No | 70 | Unknown | Yes | No |
| MB237PT | Primary tumor | Prevalence | 7 | M | MB | Yes | MB | C | No | >80 | Unknown | Yes | No |
| MB238PT | Primary tumor | Prevalence | 11 | F | MB | Yes | MB | C | No | >80 | Unknown | Yes | No |

TO FIG. 5B-2
FIG. 5B-1

FROM FIG. 5B-1

| | | | | | | | | |
|---|---|---|---|---|---|---|---|---|
| MB239PT | Primary tumor | Prevalence | 35 | F | MB | Yes | C | Yes | 70 | White | Yes | No |
| MB240PT | Primary tumor | Prevalence | 20 | M | MB | Yes | C | No | 70 | White | Yes | No |
| MB241PT | Primary tumor | Prevalence | 8 | F | MB | Yes | C | No | >80 | Unknown | Unknown | No |
| MB242PT | Primary tumor | Prevalence | 16 | F | MB | Yes | C | No | >80 | Unknown | Unknown | No |
| MB243PT | Primary tumor | Prevalence | 9 | M | MB | Yes | LCA | No | >80 | Unknown | Unknown | No |
| MB244PT | Primary tumor | Prevalence | 24 | F | MB | Yes | C | No | >80 | Unknown | Unknown | No |
| MB245PT | Primary tumor | Prevalence | 9 | M | MB | Yes | C | No | >80 | Unknown | Unknown | No |
| MB246PT | Primary tumor | Prevalence | 7 | M | MB | Yes | C | No | >80 | Unknown | Unknown | No |
| MB247PT | Primary tumor | Prevalence | 29 | M | MB | Yes | ND | No | >80 | Unknown | Unknown | No |
| MB248PT | Primary tumor | Prevalence | 33 | M | MB | Yes | C | No | >80 | Unknown | Unknown | No |
| MB249PT | Primary tumor | Prevalence | 10 | F | MB | Yes | C | No | >80 | Unknown | Unknown | No |
| MB250PT | Primary tumor | Prevalence | 48 | M | MB | Yes | LCA | No | >80 | Unknown | Unknown | No |
| MB251PT | Primary tumor | Prevalence | 26 | M | MB | Yes | LCA | No | >80 | Unknown | Unknown | No |
| MB252PT | Primary tumor | Prevalence | 21 | F | MB | Yes | LCA | No | >80 | Unknown | Unknown | No |
| MB253PT | Primary tumor | Prevalence | 32 | M | MB | Yes | ND | No | >80 | Unknown | Yes | No |
| MB103X | Xenograft | Copy number | 9 | M | MB | Yes | C | No | >80 | White | Yes | Yes |

*Patient age refers to age at which patient MB sample was obtained. #Recurrent MB designates an MB which was resected >3 months after a prior diagnosis of MB. Abbreviations: MB (medulloblastoma), M (male), F (female), ND (nodular/desmoplastic), LCA (large

FIG. 5B-2

| CSF tumor cytology status at initial diagnosis | Adjuvant (post-operative) radiation therapy | Adjuvant (post-operative) cytotoxic chemotherapy | Vital status at date of last contact | Tumor status at date of last contact | Survival after study tumor sample obtained (years) | PTCH1 mutated | CTNNB1 mutated | MLL2 mutated | TP53 mutated | MYC amplified | PTEN mutated | OTX2 amplified | SMARCA4 mutated | MLL3 mutated | Tumor ID |
|---|---|---|---|---|---|---|---|---|---|---|---|---|---|---|---|
| Positive | Yes | Yes | Deceased | With Tumor | 0.8 | | | | | Yes | | Yes | | | MB101X |
| Positive | Yes | No | Deceased | With Tumor | 0.3 | | | Yes | | Yes | | | | Yes | MB104X |
| Negative | No | Yes | Deceased | With Tumor | 0.7 | | | | | | | | | | MB105X |
| Negative | Yes | No | Deceased | With Tumor | 0.5 | | | | Yes | | Yes | | | | MB106X |
| Unknown | Unknown | Unknown | Unknown | Unknown | Unknown | | | | | | | | Yes | | MB108C |
| Negative | Yes | Yes | Deceased | With Tumor | 2.3 | | | Yes | | | | | | | MB109PT |
| Negative | Yes | Yes | Deceased | With Tumor | 9.0 | | | | | | | | | | MB111PT |
| Positive | Yes | Unknown | Living | Tumor Free | 7.0 | | | | | | | | | | MB113PT |
| Negative | Yes | Yes | Living | Tumor Free | 3.7 | | | Yes | | | | | | | MB115PT |
| Negative | No | Yes | Living | Tumor Free | 1.4 | | | | | | | | | | MB117PT |
| Negative | Yes | Yes | Living | Tumor Free | 0.8 | | | | | | | | | | MB118PT |
| Negative | Yes | Yes | Deceased | With Tumor | 2.7 | | Yes | | | | | | | | MB119PT |
| Negative | Yes | No | Living | Tumor Free | 12.1 | | | | | | | | | | MB120PT |
| Positive | No | Yes | Living | Tumor Free | 4.3 | | | | | | | | | | MB121PT |
| Negative | Yes | Yes | Deceased | With Tumor | 1.4 | | | | | | | | | | MB122PT |

FROM FIG. 5C-1

| | | | | | | |
|---|---|---|---|---|---|---|
| Unknown | Yes | Yes | Living | With Tumor | 2.6 | | MB123PT |
| Unknown | Yes | Yes | Living | Tumor Free | 3.8 | Yes | MB124PT |
| Negative | Yes | Yes | Living | Tumor Free | 3.4 | | MB125PT |
| Negative | Yes | Yes | Living | Tumor Free | 2.2 | Yes | MB126PT |
| Negative | Yes | Yes | Living | Tumor Free | 12.3 | | MB128PT |
| Unknown | Unknown | Unknown | Living | Unknown | Unknown | | MB129PT |
| Unknown | Unknown | Unknown | Living | Unknown | Unknown | Yes | MB130PT |
| Negative | Yes | No | Deceased | With Tumor | 0.5 | | MB107PT |
| Negative | Yes | Yes | Living | Tumor Free | 13.9 | | MB110PT |
| Negative | Yes | Yes | Living | Tumor Free | 12.9 | | MB112PT |
| Negative | Yes | Yes | Living | Tumor Free | 4.7 | Yes | MB114PT |
| Negative | Yes | Yes | Deceased | With Tumor | 0.8 | | MB116PT |
| Negative | Yes | Yes | Living | Tumor Free | 5.7 | Yes | MB127PT |
| Negative | Yes | Yes | Living | Tumor Free | 1.3 | Yes | MB131PT |
| Unknown | Unknown | Unknown | Unknown | Unknown | Unknown | | MB132PT |
| Unknown | Unknown | Unknown | Unknown | Unknown | Unknown | | MB133PT |
| Unknown | Unknown | Unknown | Unknown | Unknown | Unknown | | MB134PT |
| Unknown | Unknown | Unknown | Unknown | Unknown | Unknown | Yes | MB135PT |

FROM FIG. 5C-2

| | | | | | | |
|---|---|---|---|---|---|---|
| Negative | Yes | Yes | Living | With Tumor | 0.5 | | MB157PT |
| Negative | Yes | Yes | Living | Tumor Free | 1.1 | | MB158PT |
| Negative | Yes | Yes | Living | Tumor Free | 6.2 | | MB159PT |
| Negative | Yes | Yes | Living | Tumor Free | 0.6 | | MB160PT |
| Negative | Yes | Yes | Living | Tumor Free | 0.5 | Yes | MB161PT |
| Unknown | Yes | Unknown | Deceased | With Tumor | 7.0 | | MB162PT |
| Negative | Yes | Yes | Living | Tumor Free | 15.7 | | MB163PT |
| Negative | Yes | Yes | Living | Tumor Free | 9.4 | | MB164PT |
| Negative | Yes | Yes | Living | Tumor free | 2.8 | | MB201PT |
| Negative | Yes | Yes | Living | Tumor free | 3.2 | | MB202PT |
| Negative | No | Yes | Living | Tumor free | 2.4 | Yes | MB203PT |
| Negative | Yes | Yes | Living | Tumor free | 1.0 | | MB204PT |
| Negative | Yes | Yes | Living | Tumor free | 1.4 | | MB205PT | Yes
| Negative | Yes | Yes | Living | Tumor free | 2.3 | | MB206PT |
| Negative | Yes | Yes | Living | Unknown | 9.5 | Yes | MB210PT |
| Negative | Yes | Yes | Deceased | Unknown | Unknown | | MB211PT |
| Positive | Yes | Yes | Deceased | Unknown | 0.5 | | MB212PT |
| Negative | Yes | Yes | Deceased | Unknown | 1.4 | | MB213PT |

| | | | | FROM FIG. 5C-3 | | | |
|---|---|---|---|---|---|---|---|
| Negative | Yes | Yes | Living | Unknown | 5.7 | | MB214PT |
| Negative | Yes | Yes | Deceased | Unknown | 4.0 | | MB215PT |
| Negative | Yes | Yes | Living | Unknown | 6.6 | | MB216PT |
| Negative | No | Yes | Deceased | Unknown | 2.4 | Yes | MB217PT |
| Negative | Yes | Yes | Deceased | Unknown | 2.0 | | MB218PT |

FIG. 5C-4

| | | | | | | | | | | | Sample |
|---|---|---|---|---|---|---|---|---|---|---|---|
| Negative | Yes | Yes | Deceased | Unknown | 2.2 | | | | | | MB219PT |
| Negative | Yes | Yes | Living | Unknown | 5.5 | Yes | | | | | MB220PT |
| Negative | Yes | Yes | Living | Unknown | 4.2 | Yes | Yes | | | | MB221PT |
| Negative | Yes | Yes | Living | Unknown | 5.0 | | | | | | MB222PT |
| Negative | Yes | Yes | Living | Unknown | 3.8 | | | | | | MB225PT |
| Negative | Yes | Yes | Deceased | Unknown | 2.1 | | | | | | MB226PT |
| Negative | Yes | Yes | Living | Unknown | 3.6 | Yes | Yes | | Yes | | MB227PT |
| Negative | Yes | Yes | Living | Unknown | 3.5 | Yes | | | | | MB228PT |
| Negative | No | No | Deceased | Unknown | 0.0 | | | Yes | | | MB229PT |
| Negative | Yes | Yes | Living | Unknown | 3.7 | Yes | Yes | | | | MB230PT |
| Negative | No | No | Deceased | Unknown | 1.0 | | | | | Yes | MB231PT |
| Negative | Yes | Yes | Living | Unknown | 3.1 | Yes | | | | | MB232PT |
| Negative | Yes | Yes | Living | Unknown | 2.9 | Yes | | | | | MB233PT |
| Negative | No | No | Deceased | Unknown | 0.5 | | | | | | MB234PT |
| Negative | Yes | Yes | Living | Unknown | 7.1 | | | | | | MB235PT |
| Positive | Yes | Yes | Deceased | Unknown | 0.9 | | | | | | MB236PT |
| Negative | Yes | Yes | Living | Unknown | 1.2 | Yes | | | | | MB237PT |
| Negative | Yes | Yes | Living | Unknown | 0.8 | | | | | | MB238PT |

TO FIG. 5D-2
FIG. 5D-1

FROM FIG. 5D-1

| | | | | | | | | | | | | |
|---|---|---|---|---|---|---|---|---|---|---|---|---|
| Negative | Yes | Yes | Yes | Living | With tumor | 0.4 | | | Yes | | | MB239PT |
| Negative | Unknown | Unknown | Unknown | Living | Unknown | 0.1 | | | | | | MB240PT |
| Unknown | Yes | Yes | Yes | Living | Unknown | 3.4 | | | | | | MB241PT |
| Unknown | No | No | No | Deceased | Unknown | 0.0 | | Yes | | | | MB242PT |
| Unknown | Yes | Yes | Yes | Deceased | With Tumor | 1.5 | | | | | | MB243PT |
| Unknown | No | No | No | Deceased | Unknown | 0.1 | | Yes | | | | MB244PT |
| Unknown | Yes | Yes | Yes | Living | Unknown | 2.1 | | | Yes | | | MB245PT |
| Unknown | Yes | Yes | Yes | Living | Unknown | 2.0 | | Yes | Yes | | Yes | MB246PT |
| Unknown | Yes | Yes | Yes | Living | Unknown | 1.8 | Yes | | | | | MB247PT |
| Unknown | Yes | Yes | Yes | Living | Unknown | 1.9 | Yes | | | | | MB248PT |
| Unknown | Yes | Yes | Yes | Deceased | With Tumor | 0.9 | | Yes | | Yes | | MB249PT |
| Unknown | Yes | Yes | Yes | Living | Unknown | 1.3 | | | | | | MB250PT |
| Unknown | Yes | Yes | Yes | Living | Unknown | 1.1 | Yes | Yes | | | | MB251PT |
| Unknown | No | No | No | Deceased | Unknown | 0.0 | Yes | Yes | | | | MB252PT |
| Negative | Yes | Yes | Yes | Living | Unknown | 0.7 | | | Yes | | | MB253PT |
| Unknown | Yes | Yes | Yes | Deceased | With Tumor | 0.4 | | | Yes | | Yes | MB103X | cell/anaplastic), C (classic, not nodular), N/A (not available).

FIG. 5D-2 table S3. Somatic mutations identified in MB Discovery and Prevalence Screens

| Screen | Gene | Gene Name | Gene Accession | Transcript Accession | Tumor | Nucleotide (genomic)* | Nucleotide (cDNA)† | Amino acid (protein)‡ | Mutation Type | Mutation Class# | CHASM Score§ | CHASM p-value§ | CHASM q-value§ |
|---|---|---|---|---|---|---|---|---|---|---|---|---|---|
| Discovery | A4GALT | alpha 1,4-galactosyltransferase | ENSG00000128274 | ENST00000249005 | MB129PT | g.chr22:41419138C>T | c.764C>T | p.T255M | Missense | C*pG:T | 0.604 | 0.0344 | 0.30 |
| Discovery | ABCG1 | ATP-binding cassette, sub-family G | ENSG00000160179 | ENST00000361802 | MB120PT | g.chr21:42518853G>T | c.46G>T | p.A16S | Missense | G:T | 0.322 | 0.4946 | 0.70 |
| Discovery | ADAM29 | ADAM metallopeptidase domain 29 | ENSG00000168594 | ENST00000359240 | MB129PT | g.chr4:176194786G>A | c.1537G>A | p.A513T | Missense | CpG*:A | 0.884 | 0.3517 | 0.60 |
| Discovery | ADAM8 | ADAM metallopeptidase domain 8 | ENSG00000151651 | ENST00000368566 | MB111PT | g.chr10:134935053G>A | c.1253G>A | p.R418H | Missense | CpG*:A | 0.958 | 0.7660 | 0.85 |
| Discovery | ADAM9 | ADAM metallopeptidase domain 9 | ENSG00000168615 | ENST00000302458 | MB104X | g.chr8:38994088C>T | c.604C>T | p.R202X | Nonsense | C*pG:T | 0.001 | N/A | N/A |
| Discovery | ADCY9 | adenylate cyclase 9 | ENSG00000162104 | ENST00000294016 | MB130PT | g.chr16:3984670G>T | IVS287a+1G>T | Splice Site | Splice site | G:T | . | . | . |
| Discovery | AFM | afamin | ENSG00000079557 | ENST00000226355 | MB121PT | g.chr4:74572332G>T | c.64G>T | p.A21S | Missense | G:T | 0.8 | 0.1745 | 0.50 |
| Discovery | AGGF1 | angiogenic factor with G patch and... | ENSG00000164252 | ENST00000312916 | MB119PT | g.chr5:76394751G>A | c.2063G>A | p.R688Q | Missense | CpG*:A | 0.49 | 0.0128 | 0.20 |
| Discovery | AL158154.28 | NULL | ENSG00000214931 | ENST00000392261 | MB122PT | g.chr9:83725562C>T | c.663C>T | p.P221P | Synonymous | C:T | . | . | . |
| Discovery | AL596087.11 | NULL | ENSG00000215335 | ENST00000400979 | MB130PT | g.chr1:164512480G>T | c.562G>T | p.A188S | Missense | CpG*:T | . | . | . |
| Discovery | ALPK2 | alpha-kinase 2 | ENSG00000198796 | ENST00000398254 | MB105X | g.chr18:54397623C>T | c.1355C>T | p.P455P | Synonymous | C*pG:T | . | . | . |
| Discovery | ANK1 | ankyrin 1; erythrocytic | ENSG00000029534 | ENST00000398842 | MB129PT | g.chr8:41685626G>A | c.1825G>A | p.A609T | Missense | CpG*:A | 0.794 | 0.1647 | 0.50 |
| Discovery | ANK3 | ankyrin 3; node of Ranvier (ankyrin G) | ENSG00000151150 | ENST00000280772 | MB104X | g.chr10:61504116G>T | c.6529G>T | p.D2177Y | Missense | G*pA:T | 0.964 | 0.7351 | 0.85 |
| Discovery | AP4B1 | adaptor-related protein complex 4 | ENSG00000134262 | ENST00000256658 | MB108C | g.chr1:114244244A>C | c.929A>C | p.H310P | Missense | A:C | 0.562 | 0.0248 | 0.30 |
| Discovery | APOA1BP | apolipoprotein A-I binding protein | ENSG00000163382 | ENST00000366235 | MB118PT | g.chr1:154828383A>G | c.163A>G | p.T55A | Missense | A:G | 0.606 | 0.0346 | 0.30 |
| Discovery | ARID1A | AT rich interactive domain 1A (SWI) | ENSG00000117713 | ENST00000324856 | MB118PT | g.chr1:26996495delG | c.1010_1010delG | fs | INDEL | Indel | 0.001 | N/A | N/A |
| Discovery | ATP1A2 | ATPase; Na+/K+ transporting; alph | ENSG00000018625 | ENST00000361216 | MB108C | g.chr1:158368937C>A | c.1753C>A | p.L585I | Missense | C:A | 0.35 | 0.0020 | 0.15 |
| Discovery | ATP1B2 | ATPase; Na+/K+ transporting; beta | ENSG00000129244 | ENST00000250111 | MB128PT | g.chr17:7497975C>T | c.333C>T | p.N111N | Synonymous | C:T | . | . | . |
| Discovery | AZI1 | 5-azacytidine induced 1 | ENSG00000141577 | ENST00000269392 | MB115PT | g.chr17:76768150delG | c.979delG | fs | INDEL | Indel | 0.001 | N/A | N/A |

FROM FIG. 6A-1

| | | | | | | | | | |
|---|---|---|---|---|---|---|---|---|---|
| Discovery | BAZ1A | bromodomain adjacent to zinc fngr ENSG00000198604 ENST00000360310 | MB106X | g.chr14:34413447T>G | IVS113+2T>G | Splice Site | Splice site | T.G | . | . |
| Discovery | BICD1 | bicaudal D homolog 1 (Drosophila) ENSG00000151746 ENST00000281474 | MB122PT | g.chr12:32172626G>A | c.1970G>A | p.R657Q | Missense | CpG*A | 0.91 | 0.4435 | 0.65 |
| Discovery | C14orf101 | chromosome 14 open reading frame ENSG00000070269 ENST00000261556 | MB106X | g.chr14:56142063G>A | c.535G>A | p.G179S | Missense | G.A | 0.782 | 0.1497 | 0.50 |
| Discovery | C17orf104 | chromosome 17 open reading frame ENSG00000180336 ENST00000315313 | MB124PT | g.chr17:40106350C>T | c.1228C>T | p.Q410X | Nonsense | C.T | 0.001 | NA | NA |
| Discovery | C1orf167 | chromosome 1 open reading frame ENSG00000215910 ENST00000312793 | MB106X | t2605delTGGAGTGGTGGGGAGTGGTGGGCCAK | fs | INDEL | Indel | 0.001 | NA | NA |
| Discovery | C20orf70 | chromosome 20 open reading frame ENSG00000131050 ENST00000253352 | MB122PT | g.chr20:31228970C>T | c.507C>T | p.A169A | Synonymous | C*pG.T | . | . | . |
| Discovery | C4BPA | complement component 4 binding ENSG00000123838 ENST00000367070 | MB124PT | g.chr1:205393785G>A | IVS1445-1G>A | Splice Site | Splice site | G.A | . | . | . |
| Discovery | C6orf103 | chromosome 6 open reading frame ENSG00000118492 ENST00000397944 | MB104X | g.chr6:147048594C>T | c.1248G>T | p.N416V | Synonymous | C*pG.T | . | . | . |
| Discovery | C7orf33 | chromosome 7 open reading frame ENSG00000170279 ENST00000307003 | MB106X | t19114_147919125delCAGG14_175delCACGTCAAT | p.P55_N59delinsH | INDEL | Indel | . | . | . |
| Discovery | CA1 | carbonic anhydrase I ENSG00000133742 ENST00000256119 | MB106X | g.chr8:89434303C>A | c.347C>A | p.S116Y | Missense | TpC*A | 0.856 | 0.2806 | 0.60 |
| Discovery | CACNA1D | calcium channel; voltage-dependen ENSG00000157388 ENST00000288139 | MB126PT | g.chr3:53500464G>A | c.313G>A | p.A105T | Missense | CpG*A | 0.904 | 0.4191 | 0.65 |
| Discovery | CASK1N1 | CASK interacting protein 1 ENSG00000167971 ENST00000362453 | MB111PT | g.chr16:2168218C>T | c.2009C>T | p.S670L | Missense | C*pG.T | 0.948 | 0.6284 | 0.75 |
| Discovery | CCDC101 | coiled-coil domain containing 101 ENSG00000176476 ENST00000317058 | MB122PT | g.chr16:28504484G>T | c.166G>T | p.R56W | Missense | C*pG.T | 0.952 | 0.6557 | 0.80 |
| Discovery | CCDC110 | coiled-coil domain containing 110 ENSG00000168491 ENST00000317588 | MB122PT | g.chr4:186617556A>T | c.1179A>T | p.K393N | Missense | A.T | 0.508 | 0.0157 | 0.20 |
| Discovery | CCDC147 | coiled-coil domain containing 147 ENSG00000120051 ENST00000369704 | MB108C | g.chr10:105615572G>T | c.2135G>T | p.R712I | Missense | G*pA.T | 0.86 | 0.2887 | 0.60 |
| Discovery | CCDC155 | coiled-coil domain containing 155 ENSG00000161609 ENST00000293331 | MB125PT | g.chr9:54594155C>A | c.691C>A | p.S176Y | Missense | TpC*A | 0.88 | 0.3390 | 0.60 |
| Discovery | CCDC73 | coiled-coil domain containing 73 ENSG00000186714 ENST00000335185 | MB124PT | g.chr11:32653703T>C | c.6297T>C | p.I210T | Missense | T.C | 0.788 | 0.1574 | 0.50 |
| Discovery | CD177 | CD177 molecule ENSG00000204936 ENST00000378012 | MB109PT | g.chr19:48551514G>C | c.387G>C | p.M129I | Missense | G*pA.C | 0.638 | 0.0468 | 0.30 |
| Discovery | CDCP1 | CUB domain containing protein 1 ENSG00000163814 ENST00000296129 | MB124PT | g.chr3:45105611G>A | c.2020G>A | p.V674M | Missense | G.A | 0.602 | 0.0330 | 0.30 |
| Discovery | CELF6 | CUGBP, Elav-like family member 6 ENSG00000140488 ENST00000267202 | MB128PT | g.chr15:70359117C>T | c.652C>T | p.R218C | Missense | C*pG.T | 0.994 | 0.9715 | 0.95 |
| Discovery | CHD7 | chromodomain helicase DNA bindin ENSG00000171316 ENST00000307121 | MB106X | g.chr8:61833886G>A | IVS2498+1G>A | Splice Site | Splice site | G.A | . | . | . |

FROM FIG. 6A-2

| | | | | | | | | | | | |
|---|---|---|---|---|---|---|---|---|---|---|---|
| Discovery | CHMP4B | chromatin modifying protein 4B | ENSG00000011421 | ENST00000217402 | MB126PT | g.chr20:31903662C>A | c.802C>A | p.S201X | Nonsense | TpC*A | 0.001 | N/A | N/A |
| Discovery | CHRNA5 | cholinergic receptor, nicotinic; alpha | ENSG00000169684 | ENST00000299565 | MB118PT | g.chr15:75669961C>T | c.1173C>T | p.N391N | Synonymous | C.T | . | . | 0.85 |
| Discovery | CIC | capicua homolog (Drosophila) | ENSG00000079432 | ENST00000160740 | MB119PT | g.chr19:47485556C>T | c.1318C>T | p.R440C | Missense | C*pG.T | 0.966 | 0.7574 | N/A |
| Discovery | CLCN7 | chloride channel 7 | ENSG00000103249 | ENST00000302745 | MB106X | 1451639_1451631delCACAC51_2594delCACACAAC | p.P94_E97delinsQ | INDEL | Indel | 0.001 | N/A | N/A |
| Discovery | CLCN7 | chloride channel 7 | ENSG00000103249 | ENST00000302745 | MB122PT | g.chr16:1437669C>T | c.2041C>T | p.R681C | Missense | C*pG.T | 0.914 | 0.4616 | 0.70 |
| Discovery | CNTD1 | cyclin N-terminal domain containing | ENSG00000176563 | ENST00000315086 | MB106X | g.chr17:39211411C>T | c.563C>T | p.T188M | Missense | C*pG.T | 0.754 | 0.1279 | 0.50 |
| Discovery | COL10A1 | collagen; type X; alpha 1 | ENSG00000123500 | ENST00000243222 | MB108C | g.chr6:116549629G>T | c.343G>T | p.G115X | Nonsense | G.T | 0.001 | N/A | N/A |
| Discovery | COL20A1 | collagen; type XX; alpha 1 | ENSG00000101203 | ENST00000326986 | MB106X | g.chr20:61420918C>T | c.2748C>T | p.P916P | Synonymous | C*pG.T | . | . | . |
| Discovery | COL7A1 | collagen; type VII; alpha 1 | ENSG00000114270 | ENST00000328333 | MB126PT | g.chr3:48603986C>T | c.1551C>T | p.T517T | Synonymous | C*pG.T | . | . | . |
| Discovery | CORIN | corin; serine peptidase | ENSG00000145244 | ENST00000273857 | MB120PT | g.chr4:47320396C>T | c.2487C>T | p.G829G | Synonymous | C.T | . | . | . |
| Discovery | CROCC | ciliary rootlet coiled-coil; rootletin | ENSG00000058453 | ENST00000375541 | MB122PT | g.chr1:17153933A>G | c.3439A>G | p.K1147E | Missense | A.G | 0.86 | 0.2887 | 0.60 |
| Discovery | CTNNB1 | catenin (cadherin-associated protein) | ENSG00000168036 | ENST00000405570 | MB118PT | g.chr3:41241104T>G | c.97T>G | p.S33A | Missense | T.G | 0.862 | 0.2920 | 0.60 |
| Discovery | CTTNBP2 | cortactin binding protein 2 | ENSG00000077063 | ENST00000160373 | MB122PT | g.chr7:117155653A>G | c.3881A>G | p.K1294R | Missense | A.G | 0.856 | 0.3018 | 0.60 |
| Discovery | CUL4A | cullin 4A | ENSG00000139842 | ENST00000375440 | MB125PT | g.chr13:112836210A>C | IVS6.76-2A>C | Splice Site | Splice site | A.C | . | . | . |
| Discovery | CYR61 | cysteine-rich; angiogenic inducer; 6 | ENSG00000142871 | ENST00000360431 | MB118PT | g.chr1:85821020A>C | c.853A>C | p.K285Q | Missense | A.C | 0.238 | 0.0008 | 0.15 |
| Discovery | DDX3X | DEAD (Asp-Glu-Ala-Asp) box polyp | ENSG00000215301 | ENST00000399959 | MB130PT | nX:41087954T>C (homozyg) | c.700T>C | p.F234L | Missense | T.C | 0.836 | 0.2374 | 0.55 |
| Discovery | DIO2 | deiodinase, iodothyronine, type II | NM_001007023 | NM_001007023 | MB117PT | g.chr14:79739179A>T | c.542A>T | p.K181I | Missense | A.T | . | . | . |
| Discovery | DIS3 | DIS3 mitotic control homolog (S. c | ENSG00000083520 | ENST00000377767 | MB130PT | g.chr3:72244365A>T | c.1436A>T | p.D479V | Missense | A.T | 0.82 | 0.2069 | 0.50 |
| Discovery | DLGAP2 | discs, large (Drosophila) homolog | NM_004745 | NM_004745 | MB122PT | g.chr8:1494800C>T | c.614C>T | p.P205L | Missense | C*pG.T | . | . | . |
| Discovery | DNAH10 | dynein; axonemal; heavy chain 10 | ENSG00000019763 | ENST00000280576 | MB126PT | g.chr12:122968989G>A | c.6177G>A | p.K2059K | Synonymous | G.A | . | . | . |
| Discovery | DOPEY1 | dopey family member 1 | ENSG00000083097 | ENST00000349129 | MB125PT | g.chr6:33919997C>T | c.6178C>T | p.R2060W | Missense | C*pG.T | 0.946 | 0.5172 | 0.75 |
| Discovery | DYTN | dystrotelin | NM_001193730 | NM_001193730 | MB108C | g.chr2:207272783C>T | c.632C>T | p.P211L | Missense | C*pG.T | . | . | . |

FROM FIG. 6A-3

| | | | | | | | | | | | |
|---|---|---|---|---|---|---|---|---|---|---|---|
| Discovery | ECM1 | extracellular matrix protein 1 | ENSG00000143369 | ENST00000369049 | MB122PT | g.chr1:148752515G>C | c.1662G>C | p.G551A | Missense | G.C | 0.926 | 0.5129 | 0.70 |
| Discovery | ELL2 | elongation factor, RNA polymerase | ENSG00000118985 | ENST00000237853 | MB129PT | g.chr5:95262441C>T | c.841C>T | p.R281W | Missense | C*pG.T | 0.972 | 0.7980 | 0.85 |
| Discovery | EPHA2 | EPH receptor A2 | ENSG00000142627 | ENST00000407976 | MB122PT | g.chr1:16349986G>A | c.146G>A | p.G49D | Missense | G.A | 0.824 | 0.2138 | 0.50 |
| Discovery | ERBB2IP | erbb2 interacting protein | ENSG00000112851 | ENST00000284037 | MB104X | g.chr5:65385253C>A | c.2351C>A | p.S784X | Nonsense | TpC*.A | 0.001 | N/A | N/A |
| Discovery | ESYT2 | extended synaptotagmin-like protein | ENSG00000117868 | ENST00000251527 | MB115PT | g.chr7:158221015C>T | c.2526C>T | p.L842L | Synonymous | C*pG.T | . | . | . |
| Discovery | ESYT2 | extended synaptotagmin-like protein | ENSG00000117868 | ENST00000251527 | MB115PT | g.chr7:158221030G>C | c.2511G>C | p.V837V | Synonymous | G.C | 0.756 | . | . |
| Discovery | FAM38B | family with sequence similarity 38 | ENSG00000175388 | ENST00000383408 | MB129PT | g.chr18:10748129C>A | c.1551C>A | p.D517E | Missense | C.A | . | 0.1236 | 0.50 |

FIG. 6A-4

| | Gene | Description | Sample | Genomic | Coding | Protein | Effect | Context | | | |
|---|---|---|---|---|---|---|---|---|---|---|---|
| Discovery | FAM83G | family with sequence similarity 83; ENSG00000188522 ENST00000388995 | MB126PT | g.chr17:18621668C>T | c.2036C>T | p.A679V | Missense | C*pG.T | 0.984 | 0.8927 | 0.95 |
| Discovery | FLNB | filamin B, beta ENSG00000136068 ENST00000295956 | MB108C | g.chr3:58110714T>C | c.6189T>C | p.F2063P | Synonymous | T.C | - | - | - |
| Discovery | FLNC | filamin C, gamma ENSG00000128591 ENST00000325888 | MB115PT | g.chr7:128273582C>T | c.3966C>T | p.G1322G | Synonymous | C*pG.T | - | - | - |
| Discovery | FRAS1 | Fraser syndrome 1 ENSG00000138759 ENST00000380674 | MB122PT | g.chr4:79606527G>A | c.7174G>A | p.G2392S | Missense | CpG*.A | 0.502 | 0.0143 | 0.20 |
| Discovery | FSHR | follicle stimulating hormone receptor ENSG00000170820 ENST00000406846 | MB106X | g.chr2:49071273T>C | c.382T>C | p.S128P | Missense | T.C | 0.924 | 0.5023 | 0.70 |
| Discovery | GIGYF2 | GRB10 interacting GYF protein 2 ENSG00000204120 ENST00000373553 | MB129PT | g.chr2:233422336G>A | c.3832G>A | p.G1278R | Missense | G.A | - | - | - |
| Discovery | GLS2 | glutaminase 2 (liver, mitochondrial) ENSG00000135423 ENST00000311966 | MB123PT | g.chr12:55158847C>A | c.388C>A | p.R130R | Synonymous | C*pG.A | - | - | - |
| Discovery | GORASP1 | golgi reassembly stacking protein 1 ENSG00000114745 ENST00000319283 | MB118PT | g.chr3:39114915C>T | c.1139C>T | p.A380V | Missense | C*pG.T | 0.92 | 0.4659 | 0.70 |
| Discovery | GPR45 | G protein-coupled receptor 45 ENSG00000135973 ENST00000258456 | MB126PT | g.chr2:105225312C>A | c.565C>A | p.L189I | Missense | C.A | 0.93 | 0.5313 | 0.70 |
| Discovery | GRIA3 | glutamate receptor, ionotropic, A ENSG00000125675 ENST00000264357 | MB113PT | g.chrX:122356503T>C | c.754T>C | p.F252L | Missense | T.C | 0.73 | 0.1012 | 0.45 |
| Discovery | GRID1 | glutamate receptor, ionotropic, del ENSG00000182771 ENST00000327946 | MB113PT | g.chr10:87474126C>T | c.1821C>T | p.S607S | Synonymous | C*pG.T | - | - | - |
| Discovery | GTF2A2 | general transcription factor IIA, 2; 1ENSG00000140307 ENST00000267839 | MB108C | g.chr15:57721740C>T | c.191C>T | p.T64M | Missense | C*pG.T | 0.83 | 0.2248 | 0.55 |
| Discovery | GYLTL1B | glycosyltransferase-like 1B ENSG00000165905 ENST00000401752 | MB109PT | g.chr11:45904997C>T | c.1324C>T | p.R442W | Missense | C*pG.T | - | - | - |
| Discovery | HIRIP3 | HIRA interacting protein 3 ENSG00000149929 ENST00000279392 | MB104X | g.chr16:29613055C>G | c.912C>G | p.D304E | Missense | C.G | 0.9 | 0.4030 | 0.65 |
| Discovery | HNRNPA2B1 | heterogeneous nuclear ribonucleop ENSG00000122666 ENST00000354657 | MB115PT | g.chr7:26203524T>G | c.236T>G | p.M79R | Missense | T.G | 0.664 | 0.0588 | 0.35 |
| Discovery | HNRNPUL1 | heterogeneous nuclear ribonucleop ENSG00000105323 ENST00000378215 | MB130PT | g.chr19:46300358G>T | c.2088G>T | p.P696P | Synonymous | CpC*.T | - | - | - |
| Discovery | ICT1 | immature colon carcinoma transcri ENSG00000167862 ENST00000301585 | MB109PT | g.chr17:70528065C>A | c.346C>A | p.R116R | Synonymous | CpG*.A | - | - | - |
| Discovery | IL19 | interleukin 19 ENSG00000142224 ENST00000340758 | MB108C | g.chr1:205079940C>T | c.447C>T | p.F149F | Synonymous | TpC*.T | - | - | - |
| Discovery | IRGC | immunity-related GTPase family, c ENSG00000124449 ENST00000244314 | MB118PT | g.chr19:48915849G>T | c.1299G>T | p.G433G | Synonymous | G.T | - | - | - |
| Discovery | ISLR | immunoglobulin superfamily contai ENSG00000129009 ENST00000249842 | ME109PT | g.chr15:72254857T>C | c.605T>C | p.I202T | Missense | T.C | 0.844 | 0.2513 | 0.55 |
| Discovery | ITCH | itchy E3 ubiquitin protein ligase hor ENSG00000078747 ENST00000262630 | MB106X | g.chr20:32490060dupC | c.791dupC | fs | INDEL | Indel | 0.001 | N/A | N/A |
| Discovery | ITIH4 | inter-alpha (globulin) inhibitor H4 (ENSG00000055955 ENST00000266041 | MB115PT | g.chr3:52833482G>T | c.1016G>T | p.S339I | Missense | G.T | 0.91 | 0.4435 | 0.65 |

FROM FIG. 6B-1

| | | | | | | | | | | |
|---|---|---|---|---|---|---|---|---|---|---|
| Discovery | ITPRIPL1 | inositol 1,4,5-triphosphate receptor ENSG00000198885 | ENST00000361124 | MB106X | g.chr2:963357210C>T | c.1130C>T | p.R380X | Nonsense | C*pG,T | 0.001 | N/A | N/A |
| Discovery | JAG1 | jagged 1 (Alagille syndrome) | ENSG00000101384 ENST00000254958 | MB128PT | g.chr20:10636098C>T | c.703C>T | p.R235X | Nonsense | C*pG,T | 0.001 | N/A | N/A |
| Discovery | JMJD1C | jumonji domain containing 1C | ENSG00000171988 ENST00000393262 | MB106X | g.chr10:64645359G>A | c.782G>A | p.R261Q | Missense | CpG*,A | 0.606 | 0.0346 | 0.30 |
| Discovery | KCNN2 | potassium intermediate/small cond | ENSG00000080709 ENST00000358446 | MB129PT | g.chr5:113725517>C | IVS1-4T>C | Splice Site | Splice site | T,C | . | . | . |
| Discovery | KDM6B | lysine (K)-specific demethylase 6B | ENSG00000132510 ENST00000254846 | MB129PT | g.chr17:7663889C>T | c.3466C>T | p.R1156X | Nonsense | C*pG,T | 0.001 | N/A | N/A |
| Discovery | KIAA1161 | KIAA1161 | ENSG00000164976 ENST00000297625 | MB130PT | g.chr9:34352705C>T | c.135C>T | p.S45S | Synonymous | C*pG,T | . | . | . |
| Discovery | KIF19 | kinesin family member 19 | ENSG00000196169 ENST00000375373 | MB106X | g.chr17:69334200G>A | c.593G>A | p.P198H | Missense | C,A | 0.896 | 0.3871 | 0.65 |
| Discovery | KIF24 | kinesin family member 24 | ENSG00000186638 ENST00000402558 | MB115PT | g.chr9:34280198T>C | c.1101T>C | p.L367L | Synonymous | T,C | . | . | . |
| Discovery | KIFC3 | kinesin family member C3 | ENSG00000140859 ENST00000379655 | MB108C | g.chr16:56352330G>A (homozyg | c.2041G>A | p.V681M | Missense | CpG*,A | 0.868 | 0.3069 | 0.60 |
| Discovery | KLF7 | Kruppel-like factor 7 (ubiquitous) | ENSG00000118263 ENST00000339446 | MB115PT | g.chr2:207654237C>A | IVS8&6-4C>A | Splice Site | Splice site | C,A | . | . | . |
| Discovery | LAMB1 | laminin, beta 1 | ENSG00000091136 ENST00000333561 | MB104X | g.chr7:107387115C>T | c.2577C>T | p.P859P | Synonymous | C*pG,T | . | . | . |
| Discovery | LHX1 | LIM homeobox 1 | ENSG00000132130 ENST00000264457 | MB130PT | g.chr17:32369612T>G | c.57>G | p.V2G | Missense | T,G | 0.728 | 0.0992 | 0.40 |
| Discovery | LRP1 | low density lipoprotein receptor-rel | ENSG00000123384 ENST00000243077 | MB128PT | g.chr12:5568021 44dupC | c.12572dupC | fs | INDEL | Indel | 0.001 | N/A | N/A |
| Discovery | LRP6 | low density lipoprotein receptor-rel | ENSG00000070018 ENST00000261349 | MB113PT | g.chr12:12283180G>C | c.2641G>C | p.V681L | Missense | CpG*,C | 0.788 | 0.1574 | 0.50 |
| Discovery | LTBP3 | latent transforming growth factor b | ENSG00000168056 ENST00000301873 | MB130PT | g.chr11:65070517G>A | c.2325G>A | p.A775A | Synonymous | CpG*,A | . | . | . |
| Discovery | MAMDC4 | MAM domain containing 4 | ENSG00000177943 ENST00000317446 | MB108C | g.chr9:138871945G>T | c.2340G>T | p.V780V | Synonymous | G,T | . | . | . |
| Discovery | MAPK7 | mitogen-activated protein kinase 7 | ENSG00000166484 ENST00000299612 | MB106X | g.chr17:19226165delC | c.1956delC | fs | INDEL | Indel | 0.001 | N/A | N/A |
| Discovery | MAPKBP1 | mitogen-activated protein kinase bi | ENSG00000137802 ENST00000399531 | MB108C | g.chr15:36892043G>A | c.536G>A | p.R179Q | Missense | CpG*,A | 0.806 | 0.1822 | 0.50 |
| Discovery | MCAM | melanoma cell adhesion molecule | ENSG00000076706 ENST00000264036 | MB122PT | g.chr11:118885308G>A | c.800G>A | p.R267H | Missense | CpG*,A | 0.986 | 0.9116 | 0.95 |
| Discovery | MED12L | mediator complex subunit 12-like | ENSG00000144893 ENST00000273432 | MB111PT | g.chr3:152569863C>T | c.3495C>T | p.A1165A | Synonymous | C*pG,T | . | . | . |
| Discovery | MED23 | mediator complex subunit 23 | ENSG00000112282 ENST00000338358 | MB129PT | g.chr6:131965938C>T | c.1854C>T | p.M518I | Missense | G,T | 0.728 | 0.0992 | 0.45 |
| Discovery | MEI1 | meiosis inhibitor 1 | ENSG00000167077 ENST00000330398 | MB108C | g.chr22:40449801A>C | c.742A>C | p.R248R | Synonymous | A,C | . | . | . |

FROM FIG. 6B-2

| | | | | | | | | | |
|---|---|---|---|---|---|---|---|---|---|
| Discovery | MFSD6L | major facilitator superfamily domain ENSG00000185156 ENST00000329805 | MB130PT | g.chr17:86418151>C | p.F453S | Missense | T,C | 0.854 | 0.2761 | 0.55 |
| Discovery | MIPOL1 | mirror-image polydactyly 1 | ENSG00000151338 ENST00000327441 | MB105X | g.chr14:38347454A>C | p.E269D | Missense | A,C | 0.326 | 0.0016 | 0.15 |
| Discovery | MIR647 | microRNA 647 | hsa-mir-647 | MI0003662 | MB130PT | g.chr20:62044508G>A | p.V6M | Missense | G,A | - | - | - |
| Discovery | MKI67 | antigen identified by monoclonal ar ENSG00000148773 ENST00000368654 | MB105X | 10:129791121_129791120del | c.8973_8974delGC | fs | INDEL | Indel | 0.001 | N/A | N/A |
| Discovery | MLL | myeloid/lymphoid or mixed-lineage ENSG00000118058 ENST00000389313 | MB130PT | g.chr11:117867654G>A | IVS4995+1G>A | Splice Site | Splice site | G,A | - | - | - |
| Discovery | MLL2 | myeloid/lymphoid or mixed-lineage ENSG00000167548 ENST00000301067 | MB104X | g.chr12:47702113C>T | p.R4921X | Nonsense | C*pG,T | 0.001 | N/A | N/A |
| Discovery | MLL2 | myeloid/lymphoid or mixed-lineage ENSG00000167548 ENST00000301067 | MB115PT | g.chr12:47702633G>A | p.R4852Q | Missense | CpG*,A | 0.768 | 0.1326 | 0.50 |
| Discovery | MLL2 | myeloid/lymphoid or mixed-lineage ENSG00000167548 ENST00000301067 | MB124PT | g.chr12:47718726delC | fs | INDEL | Indel | 0.001 | N/A | N/A |
| Discovery | MLL2 | myeloid/lymphoid or mixed-lineage ENSG00000167548 ENST00000301067 | MB126PT | g.chr12:47712043C>T | p.R3568C | Missense | C*pG,T | 0.986 | 0.9116 | 0.95 |
| Discovery | MLL2 | myeloid/lymphoid or mixed-lineage ENSG00000167548 ENST00000301067 | MB130PT | g.chr12:47717812delC | fs | INDEL | Indel | 0.001 | N/A | N/A |
| Discovery | MLL3 | myeloid/lymphoid or mixed-lineage ENSG00000055609 ENST00000262189 | MB104X | g.chr7:151505646C>T | p.R2609X | Nonsense | C*pG,T | 0.001 | N/A | N/A |
| Discovery | MMADHC | methylmalonic aciduria (cobalamin ENSG00000168288 ENST00000303319 | MB108C | g.chr2:150134912C>G | p.T233R | Missense | C,G | 0.918 | 0.4806 | 0.70 |
| Discovery | MTNR1A | melatonin receptor 1A | ENSG00000168412 ENST00000307161 | MB129PT | g.chr4:187391911G>A | p.V327M | Missense | CpG*,A | 0.928 | 0.5215 | 0.70 |
| Discovery | MXI1 | MAX interactor 1 | ENSG00000119950 ENST00000239007 | MB104X | g.chr10:111973959A>G | unknown | unknown | A,G | - | - | - |
| Discovery | MYH3 | myosin, heavy chain 3; skeletal mu ENSG00000109063 ENST00000226209 | MB108C | g.chr17:10498910C>A | p.Y360X | Nonsense | C*pG,A | 0.001 | N/A | N/A |
| Discovery | MYH9 | myosin, heavy chain 9; non-muscle ENSG00000100345 ENST00000216181 | MB130PT | g.chr22:35026660C>T | p.A800V | Missense | C,T | 0.836 | 0.2374 | 0.55 |
| Discovery | MYO3B | myosin IIIB | ENSG00000167originated ENST00000285039 | MB108C | g.chr18:4581728A>G | p.N131S | Missense | A,G | 0.43 | 0.0061 | 0.15 |
| Discovery | NAV1 | neuron navigator 1 | ENSG00000134389 ENST00000367296 | MB115PT | g.chr1:200055616C>A | p.A1836D | Missense | C,A | 0.87 | 0.3130 | 0.60 |
| Discovery | NCKAP5L | NCK-associated protein 5-like | ENSG00000167566 ENST00000335999 | MB105X | g.chr12:49472503C>T | p.T853I | Missense | C,T | 0.904 | 0.4191 | 0.65 |
| Discovery | NCOR1 | nuclear receptor co-repressor 1 | ENSG00000141027 ENST00000395846 | MB126PT | g.chr17:15970171dupA | c.1587dupA | fs | INDEL | Indel | 0.001 | N/A | N/A |
| Discovery | NDUFS4 | NADH dehydrogenase (ubiquinone ENSG00000164258 ENST00000296684 | MB130PT | g.chr5:52977876delG | c.234delG | fs | INDEL | Indel | 0.001 | N/A | N/A |
| Discovery | NEB | nebulin | ENSG00000183091 ENST00000172853 | MB117PT | g.chr2:152177100C>T | p.P3341L | Missense | C,T | 0.77 | 0.1342 | 0.50 |

FROM FIG. 6B-3

| | | | | | | | | | | |
|---|---|---|---|---|---|---|---|---|---|---|
| Discovery | NFASC | neurofascin homolog (chicken) | ENSG00000163531 ENST00000367172 | MB106X | g.chr1:203215237T>C | c.2103T>C | p.R701R | Synonymous | T,C | . | . | . |
| Discovery | NFE2L2 | nuclear factor (erythroid-derived 2) | ENSG00000116044 ENST00000397063 | MB130PT | g.chr2:177807200G>A | c.91G>A | p.G31R | Missense | G,A | 0.592 | 0.0314 | 0.30 |
| Discovery | NLRP5 | NLR family, pyrin domain containin | ENSG00000174487 ENST00000399649 | MB106X | g.chr19:61264575C>A | c.3472C>A | p.L1158M | Missense | C,A | 0.63 | 0.0434 | 0.30 |
| Discovery | NLRP8 | NLR family, pyrin domain containin | ENSG00000179709 ENST00000291971 | MB125PT | g.chr19:61158444G>A | c.1208G>A | p.C403Y | Missense | G,A | 0.776 | 0.1423 | 0.50 |
| Discovery | NOTCH4 | notch 4 | ENSG00000204301 ENST00000375023 | MB130PT | g.chr6:32274238C>T | c.4694C>T | p.A1565V | Missense | C,T | 0.986 | 0.9116 | 0.95 |
| Discovery | NRXN2 | neurexin 2 | ENSG00000110076 ENST00000265459 | MB128PT | g.chr11:64214495dupG | c.808dupG | fs | INDEL | indel | 0.001 | N/A | N/A |
| Discovery | NTSR1 | neurotensin receptor 1 (high affinity) | ENSG00000101188 ENST00000377050 | MB106X | g.chr20:60611204C>A | c.200C>A | p.T67N | Missense | C,A | 0.768 | 0.1326 | 0.50 |

FIG. 6B-4

| | | | | | | | | | | |
|---|---|---|---|---|---|---|---|---|---|---|
| Discovery | OPRM1 | opioid receptor, mu 1 | ENSG00000112038 | ENST00000330432 | MB111PT | g.chr6:154402223C>G | c.37C>G | p.L13V | Missense | C,G | 0.566 | 0.0257 | 0.30 |
| Discovery | OR52L1 | olfactory receptor, family 52, subfa | ENSG00000183313 | ENST00000332249 | MB128PT | g.chr11:5964671C>A | c.66C>A | p.S22R | Missense | C,A | 0.794 | 0.1647 | 0.50 |
| Discovery | OR6A2 | olfactory receptor, family 6, subfam | ENSG00000184933 | ENST00000332601 | MB104X | g.chr11:6773136G>A | c.380G>A | p.R127H | Missense | CpG*,A | 0.818 | 0.2022 | 0.50 |
| Discovery | OR6P1 | olfactory receptor, family 6, subfam | ENSG00000186440 | ENST00000334632 | MB130PT | g.chr1:156799993C>T | c.59C>T | p.T20M | Missense | CpG,T | 0.924 | 0.5023 | 0.70 |
| Discovery | OR7A5 | olfactory receptor, family 7, subfam | ENSG00000188239 | ENST00000322301 | MB130PT | g.chr19:14799555C>T | c.493C>T | p.R165W | Missense | CpG,T | 0.918 | 0.4806 | 0.70 |
| Discovery | OTOA | otoancorin | ENSG00000155719 | ENST00000263149 | MB104X | g.chr16:21647125G>A | c.2121G>A | p.P707P | Synonymous | CpG*,A | - | - | - |
| Discovery | OTOP1 | otopetrin 1 | ENSG00000163982 | ENST00000295358 | MB129PT | chr4:4250495_4250494dupG | c.954_955dupGC | fs | INDEL | Indel | 0.001 | N/A | N/A |
| Discovery | PAK7 | p21 protein (Cdc42/Rac)-activated | ENSG00000101349 | ENST00000378423 | MB111PT | g.chr20:9509423C>T | c.359C>T | p.A120V | Missense | CpG,T | 0.958 | 0.6982 | 0.80 |
| Discovery | PARM1 | prostate androgen-regulated mucin | ENSG00000165116 | ENST00000307428 | MB104X | g.chr4:76077487A>C | c.103A>C | p.S35R | Missense | A,C | 0.932 | 0.5396 | 0.70 |
| Discovery | PAX6 | paired box 6 | ENSG00000007372 | ENST00000241001 | MB130PT | g.chr11:31778965A>G | c.415A>G | p.R139G | Missense | A,G | 0.972 | 0.7980 | 0.90 |
| Discovery | PCSK9 | proprotein convertase subtilisin/kex | ENSG00000169174 | ENST00000302118 | MB104X | g.chr1:55299804C>A | c.1850C>A | p.A617D | Missense | C,A | 0.872 | 0.3162 | 0.60 |
| Discovery | PIGG | phosphatidylinositol glycan anchor | ENSG00000174227 | ENST00000310340 | MB104X | g.chr4:523012G>A | c.2782G>A | p.V928I | Missense | CpG*,A | 0.804 | 0.1802 | 0.50 |
| Discovery | PISD | phosphatidylserine decarboxylase | ENSG00000100141 | ENST00000397508 | MB122PT | g.chr22:30347705G>A | c.486G>A | p.R163H | Missense | CpG*,A | 0.894 | 0.3796 | 0.65 |
| Discovery | PKD1 | polycystic kidney disease 1 (autos | ENSG00000008710 | ENST00000262304 | MB120PT | g.chr16:2082563G>A | c.11188G>A | p.V3730M | Missense | CpG*,A | 0.982 | 0.8784 | 0.95 |
| Discovery | PLEKHA7 | pleckstrin homology domain contain | ENSG00000166689 | ENST00000355861 | MB129PT | g.chr11:16795335C>T | c.1454C>T | p.S485L | Missense | CpG,T | 0.982 | 0.8784 | 0.95 |
| Discovery | PLXNA2 | plexin A2 | ENSG00000076356 | ENST00000321063 | MB108C | g.chr1:208456888A>T | c.1068A>T | p.K356N | Missense | A,T | 0.85 | 0.2676 | 0.55 |
| Discovery | PPAPR3 | lipid phosphate phosphatase-relate | ENSG00000117598 | ENST00000263177 | MB130PT | g.chr8:9919478C>T | c.361C>T | p.R121X | Nonsense | C*pG,T | 0.001 | N/A | N/A |
| Discovery | PRDX6 | peroxiredoxin 6 | ENSG00000117592 | ENST00000340385 | MB117PT | g.chr1:173132486G>A | c.89G>A | p.G30E | Missense | G*pA,A | 0.452 | 0.0073 | 0.15 |
| Discovery | PRMT8 | protein arginine methyltransferase | ENSG00000111218 | ENST00000382622 | MB108C | g.chr12:3548986T>C | c.707T>C | p.I236T | Missense | T,C | 0.622 | 0.0405 | 0.30 |
| Discovery | PTCH1 | patched homolog 1 (Drosophila) | ENSG00000185920 | ENST00000375274 | MB130PT | hr9:97261880_97261879insC | c.2710_2711insCTT | p.K904delinsTX | INDEL | Indel | 0.001 | N/A | N/A |
| Discovery | PTCH1 | patched homolog 1 (Drosophila) | ENSG00000185920 | ENST00000375274 | MB130PT | g.chr9:97264091G>A | c.707G>A | p.W236X | Nonsense | G,A | 0.001 | N/A | N/A |
| Discovery | PTEN | phosphatase and tensin homolog | ENSG00000171862 | ENST00000371953 | MB105X | rl0:89682894C>T (homozyg | c.388C>T | p.R130X | Nonsense | C*pG,T | 0.001 | N/A | N/A |

FROM FIG. 6B-1

| | | | | | | | | | |
|---|---|---|---|---|---|---|---|---|---|
| Discovery | R3HCC1 | R3H domain and coiled-coil contain | NM_001136108 | MB130PT | g.chr8:23208231G>A | c.540G>A | p.A180A | Synonymous | CpG*:A | . | . | . |
| Discovery | RAB11FIP1 | RAB11 family interacting protein 1 | ENSG00000156675 ENST00000330843 | MB105X | g.chr8:37848921G>A | c.2551C>A | p.C851R | Missense | CpG*:A | 0.956 | 0.6825 | 0.80 |
| Discovery | RAB40B | RAB40B; member RAS oncogene | ENSG00000141542 ENST00000269347 | MB128PT | g.chr17:78209074A>C | c.791A>C | p.C264P | Missense | A:C | 0.774 | 0.1391 | 0.50 |
| Discovery | RALYL | RALY RNA binding protein-like | NM_001100391 | MB101X | g.chr8:85604340G>T | c.268G>T | p.A90S | Missense | G:T | . | . | . |
| Discovery | REST | RE1-silencing transcription factor | ENSG00000084093 ENST00000358605 | MB125PT | CAGAAGGAACCTGTTAAGAAGGAACCTGTTA | p.M730_P745del | INDEL | Indel | 0.001 | N/A | N/A |
| Discovery | RIMS2 | regulating synaptic membrane exo | NM_001100117 | MB130PT | g.chr8:105092271C>T | c.2222C>T | p.T741M | Missense | C*pG:T | . | . | . |
| Discovery | RIOK3 | RIO kinase 3 (yeast) | ENST00000339486 | MB115PT | g.chr18:19391432C>T | c.750C>T | p.I250I | Synonymous | TpC*:T | . | . | . |
| Discovery | ROR1 | receptor tyrosine kinase-like orpha | ENSG00000185483 ENST00000371079 | MB120PT | g.chr1:64415780G>A | c.1468G>A | p.G490S | Missense | G:A | 0.462 | 0.0079 | 0.15 |
| Discovery | RPH3A | rabphilin 3A homolog (mouse) | ENSG00000089169 ENST00000399385 | MB124PT | g.chr12:111813134delinsTT | c.1706delinsTT | fs | INDEL | Indel | 0.001 | N/A | N/A |
| Discovery | RPS6KA6 | ribosomal protein S6 kinase; 90kDa | ENSG00000072133 ENST00000262752 | MB119PT | g.chrX:83259119delG | c.790-1delG | Splice Site | INDEL | Indel | . | . | . |
| Discovery | RPS6KL1 | ribosomal protein S6 kinase-like 1 | ENSG00000198208 ENST00000358328 | MB108C | g.chr14:74443482G>C | c.1638G>C | p.K546N | Missense | G:C | 0.948 | 0.6284 | 0.75 |
| Discovery | RYR1 | ryanodine receptor 1 (skeletal) | ENSG00000196218 ENST00000359596 | MB124PT | g.chr19:43657861C>T | c.4224C>T | p.P1408P | Synonymous | C:T | . | . | . |
| Discovery | S1PR2 | sphingosine-1-phosphate receptor | ENSG00000173898 ENST00000317726 | MB108C | g.chr19:10195940C>T | c.642C>T | p.C214C | Synonymous | C*pG:T | . | . | . |
| Discovery | SCTR | secretin receptor | ENSG00000080293 ENST00000019103 | MB122PT | g.chr2:199382190G>A | c.588G>A | p.D196N | Missense | G*pA:A | 0.872 | 0.3162 | 0.60 |
| Discovery | SHPRH | SNF2 histone linker PHD RING hel | ENSG00000146414 ENST00000367503 | MB104X | c.chr6:146317657dupA | c.495dupA | fs | INDEL | Indel | 0.001 | N/A | N/A |
| Discovery | SLC17A5 | solute carrier family 17 (anion/suga | ENSG00000118839 | MB115PT | h6:74404874_74404872delC | c.595_597delCTT | p.L199del | INDEL | Indel | . | . | . |
| Discovery | SLC35E1 | solute carrier family 35, member E | ENSG00000127526 ENST00000249069 | MB129PT | g.chr19:16538349C>A | c.318C>A | p.S106R | Missense | C*pG:A | 0.902 | 0.4117 | 0.65 |
| Discovery | SLC36A2 | solute carrier family 36 (proton/am | ENSG00000186335 ENST00000335244 | MB130PT | g.chr5:150686108G>A | c.942G>A | p.A314A | Synonymous | CpG*:A | . | . | . |
| Discovery | SLITRK2 | SLIT and NTRK-like family, membe | ENSG00000185985 ENST00000394024 | MB124PT | g.chrX:144711623G>A | c.17G>A | p.W6X | Nonsense | G:A | 0.001 | N/A | N/A |
| Discovery | SMARCA4 | SWI/SNF related; matrix associate | ENSG00000127616 ENST00000358026 | MB108C | g.chr19:11005114G>A | c.3695G>A | p.G1232D | Missense | G:A | 0.75 | 0.1191 | 0.50 |
| Discovery | SMC1A | structural maintenance of chromos | ENSG00000072501 ENST00000322213 | MB128PT | g.chrX:53453119A>C | c.1295A>C | p.Q432P | Missense | A:C | 0.916 | 0.4700 | 0.70 |
| Discovery | SND1 | staphylococcal nuclease and tudor | ENSG00000197157 | MB119PT | 127079670insTCCTCCCCGGCCTCCGGCCAGAGCC | p.A2_S3insSSAQSGG | INDEL | Indel | . | . | . |

FROM FIG. 6B-2

| | | | | | | | | | |
|---|---|---|---|---|---|---|---|---|---|
| Discovery | SORCS1 | sortilin-related VPS10 domain cont | ENSG00000108018 | ENST00000344440 | MB130PT | g.chr10:108459015>T | c.1099G>T | p.D367Y | Missense | G*pA.T | 0.914 | 0.4616 | 0.65 |
| Discovery | SPRYD3 | SPRY domain containing 3 | ENSG00000167778 | ENST00000361463 | MB104X | g.chr12:51746735G>T | c.912G>T | p.K304N | Missense | G*pA.T | 0.924 | 0.5023 | 0.70 |
| Discovery | SRBD1 | S1 RNA binding domain 1 | ENSG00000068784 | ENST00000263736 | MB115PT | g.chr2:45470192C>A | c.2749C>A | p.Q917K | Missense | C.A | 0.9 | 0.4030 | 0.65 |
| Discovery | SSPO | SCO-spondin homolog (Bos taurus | NM_198455 | NM_198455 | MB115PT | 7:149147451_149147463dupc.11935_11937dupGTC | | p.V3979dup | INDEL | Indel | . | . | . |
| Discovery | STX8 | syntaxin 8 | ENSG00000170310 | ENST00000306357 | MB109PT | g.chr17:9389321C>A | IVS213-3C>A | Splice Site | Splice site | CA | . | . | . |
| Discovery | SULF1 | sulfatase 1 | ENSG00000137573 | ENST00000260128 | MB106X | g.chr8:70713387C>T | c.2381C>T | p.A794V | Missense | C.T | 0.948 | 0.6284 | 0.75 |
| Discovery | TAF1L | TAF1 RNA polymerase II; TATA bc | ENSG00000122728 | ENST00000242310 | MB119PT | g.chr9:32625188G>T | c.390G>T | p.L130F | Missense | G.T | 0.896 | 0.3871 | 0.65 |
| Discovery | TBR1 | T-box, brain; 1 | ENSG00000136535 | ENST00000389554 | MB125PT | g.chr2:161992663C>T | c.823G>T | p.G275C | Missense | CpG*.T | 0.816 | 0.1985 | 0.50 |
| Discovery | TEC | tec protein tyrosine kinase | ENSG00000135605 | ENST00000381501 | MB101X | g.chr4:47841934A>C | c.1369A>C | p.R457R | Synonymous | A.C | . | . | . |
| Discovery | TG | thyroglobulin | ENSG00000042832 | ENST00000220616 | MB126PT | g.chr8:133994013A>C | c.863A>C | p.Q288P | Missense | A.C | 0.568 | 0.0307 | 0.30 |
| Discovery | TJP1 | tight junction protein 1 (zona occlu | ENSG00000104067 | ENST00000480011 | MB113PT | g.chr15:27783793C>T | c.4840C>T | p.L1617L | Synonymous | C.T | . | . | . |
| Discovery | TMEM181 | transmembrane protein 181 | ENSG00000146433 | ENST00000367090 | MB104X | g.chr6:159948350G>C | c.1071G>C | p.L357L | Synonymous | G.C | . | . | . |
| Discovery | TMEM79 | transmembrane protein 79 | ENSG00000163472 | ENST00000361292 | MB126PT | g.chr1:154620790C>T | c.438C>T | p.I146I | Synonymous | C*pG.T | . | . | . |
| Discovery | TMPRSS9 | transmembrane protease; serine 9 | ENSG00000178297 | ENST00000332578 | MB123PT | g.chr19:2356435C>T | c.632C>T | p.P211L | Missense | C*pG.T | 0.89 | 0.3665 | 0.60 |
| Discovery | TP53 | tumor protein p53 | ENSG00000141510 | ENST00000269305 | MB106X | sr17:7518263G>A (homozygo | c.743G>A | p.R248Q | Missense | CpG*.A | 0.438 | 0.0067 | 0.15 |
| Discovery | TRAP1 | TNF receptor-associated protein 1 | ENSG00000126602 | ENST00000246957 | MB104X | g.chr16:3648827G>C | c.1981G>C | p.E661Q | Missense | CpG*.C | 0.982 | 0.8784 | 0.95 |
| Discovery | TRIM24 | tripartite motif-containing 24 | ENSG00000122779 | ENST00000343526 | MB115PT | g.chr7:137920110G>T | c.3027G>T | p.R1009S | Missense | G.T | 0.926 | 0.5129 | 0.70 |
| Discovery | TSC1 | tuberous sclerosis 1 | ENSG00000165699 | ENST00000298552 | MB124PT | 4765935_137659929delinsG6613_2616delinsGGGGC | | fs | INDEL | Indel | 0.001 | N/A | N/A |
| Discovery | TTC23L | tetratricopeptide repeat domain 23 | NM_144725 | NM_144725 | MB108C | g.chr5:34902265C>T | c.774C>T | p.Y258Y | Synonymous | C*pG.T | . | . | . |
| Discovery | TTC6 | tetratricopeptide repeat domain 6 | ENSG00000139865 | ENST00000332320 | MB120PT | g.chr14:37336570G>C | c.919G>C | p.G307R | Missense | CpG*.C | 0.854 | 0.2761 | 0.60 |
| Discovery | UBE2D2 | ubiquitin-conjugating enzyme E2D | ENSG00000131508 | ENST00000398734 | MB122PT | g.chr5:138974689C>T | c.268C>T | p.R90X | Nonsense | C*pG.T | 0.001 | N/A | N/A |
| Discovery | UPF1 | UPF1 regulator of nonsense trans | ENSG00000005007 | ENST00000262803 | MB108C | g.chr19:18826708C>T | c.1286C>T | p.T429M | Missense | C*pG.T | 0.982 | 0.8784 | 0.95 |

FROM FIG. 6B-3

| | | | | | | | | | | |
|---|---|---|---|---|---|---|---|---|---|---|
| Discovery | USP44 | ubiquitin specific peptidase 44 | ENSG00000136014 ENST00000393091 | MB106X | g.chr12:94446764C>G | c.1574C>G | p.T525R | Missense | C.G | 0.87 | 0.3130 | 0.60 |
| Discovery | WDR16 | WD repeat domain 16 | ENSG00000166696 ENST00000299764 | MB126PT | g.chr17:9460843A>G | c.404A>G | p.Y135C | Missense | A.G | 0.682 | 0.0678 | 0.35 |
| Discovery | WDR17 | WD repeat domain 17 | ENSG00000150627 ENST00000280190 | MB130PT | g.chr4:177293380C>T | c.1298C>T | p.P433L | Missense | C*pG.T | 0.8 | 0.1745 | 0.50 |
| Discovery | WDR60 | WD repeat domain 60 | ENSG00000126870 ENST00000407559 | MB115PT | 7:158356636_158356836del | c.312_314delGAA | p.K105del | INDEL | Indel | . | . | . |
| Discovery | XRRA1 | X-ray radiation resistance associat | ENSG00000166435 ENST00000321448 | MB122PT | g.chr11:74239861C>T | c.1276C>T | p.R426X | Nonsense | C*pG.T | 0.001 | N/A | N/A |
| Discovery | YAP1 | Yes-associated protein 1 | ENSG00000137693 ENST00000282441 | MB108C | g.chr11:101538499G>A | c.675G>A | p.M225I | Missense | G*pA.A | 0.846 | 0.2560 | 0.55 |
| Discovery | ZCCHC7 | zinc finger, CCHC domain containi | ENSG00000147905 ENST00000339755 | MB104X | n9.37116524G>A (homozygc | c.195G>A | p.S65S | Synonymous | CpG*.A | . | . | . |

FIG. 6C-4

| Category | Gene | Description | Transcript | Genomic | cDNA | Protein | Type | Context | Col9 | Col10 | Col11 |
|---|---|---|---|---|---|---|---|---|---|---|---|
| Discovery | ZDHHC3 | zinc finger, DHHC-type containing 3 | ENSG00000099904 | ENST00000405930 | MB123PT | g.chr22:18311098C>A | c.1943C>A | p.A648D | Missense | C:A | 0.33 | 0.5313 | 0.70 |
| Discovery | ZIC4 | Zic family member 4 | ENSG00000174963 | ENST00000383075 | MB130PT | g.chr3:148596668_148596665insTA | c.346_34TinsTA | fs | INDEL | Indel | 0.001 | N/A | N/A |
| Discovery | ZNF219 | zinc finger protein 219 | ENSG00000165804 | ENST00000360947 | MB106X | g.chr14:20830918C>T | c.378C>T | p.R126R | Synonymous | CpG:T | . | . | . |
| Discovery | ZNF280D | zinc finger protein 280D | ENSG00000137871 | ENST00000398245 | MB124PT | g.chr15:54734283G>A | c.1219G>A | p.V407I | Missense | G:A | 0.888 | 0.3625 | 0.60 |
| Discovery | ZNF609 | zinc finger protein 609 | ENSG00000180357 | ENST00000326648 | MB130PT | g.chr15:62753624C>A | c.1518C>A | p.Y506X | Nonsense | C:A | 0.001 | N/A | N/A |
| Discovery | ZNF683 | zinc finger protein 683 | ENSG00000176083 | ENST00000403843 | MB129PT | g.chr1:26561081G>T | c.1223G>T | p.S408I | Missense | G:T | 0.9 | 0.4030 | 0.65 |
| Discovery | ZNF710 | zinc finger protein 710 | ENSG00000140346 | ENST00000268154 | MB106X | g.chr15:88412685C>T | c.1312C>T | p.L438F | Missense | C:T | 0.738 | 0.1081 | 0.45 |
| Discovery | ZNF818 | zinc finger protein 818, pseudogene | ENSG00000204597 | ENST00000344759 | MB122PT | g.chr19:58408338A>G | c.288A>G | p.K96K | Synonymous | A:G | . | . | . |
| Discovery | ZP2 | zona pellucida glycoprotein 2 (sperm...) | ENSG00000103310 | ENST00000219593 | MB106X | g.chr16:21124561G>A | c.520G>A | p.D174N | Missense | CpG*:A | 0.798 | 0.1712 | 0.50 |
| Discovery | ZZEF1 | zinc finger, ZZ-type with EF-hand d... | ENSG00000074755 | ENST00000381633 | MB113PT | g.chr17:3825532C>T | c.3375C>T | p.F1125F | Synonymous | CpG:T | . | . | . |
| Prevalence | CTNNB1 | catenin (cadherin-associated protein) | ENSG00000168036 | ENST00000405570 | MB210PT | g.chr3:41241105C>A | c.98C>A | p.S33Y | Missense | TpC*:A | 0.864 | 0.2871 | 0.60 |
| Prevalence | CTNNB1 | catenin (cadherin-associated protein) | ENSG00000168036 | ENST00000405570 | MB219PT | g.chr3:41241105C>T | c.98C>T | p.S33F | Missense | TpC*:T | 0.808 | 0.1857 | 0.50 |
| Prevalence | CTNNB1 | catenin (cadherin-associated protein) | ENSG00000168036 | ENST00000405570 | MB228PT | g.chr3:41241117C>G | c.110C>G | p.S37C | Missense | TpC*:G | 0.846 | 0.2761 | 0.55 |
| Prevalence | CTNNB1 | catenin (cadherin-associated protein) | ENSG00000168036 | ENST00000405570 | MB231PT | g.chr3:41241105C>G | c.98C>G | p.S33C | Missense | TpC*:G | 0.846 | 0.2560 | 0.55 |
| Prevalence | CTNNB1 | catenin (cadherin-associated protein) | ENSG00000168036 | ENST00000405570 | MB238PT | g.chr3:41241101G>T | c.94G>T | p.D32Y | Missense | G*pA:T | 0.796 | 0.1684 | 0.50 |
| Prevalence | CTNNB1 | catenin (cadherin-associated protein) | ENSG00000168036 | ENST00000405570 | MB242PT | g.chr3:41241105C>T | c.98C>T | p.S33F | Missense | TpC*:T | 0.888 | 0.1857 | 0.50 |
| Prevalence | CTNNB1 | catenin (cadherin-associated protein) | ENSG00000168036 | ENST00000405570 | MB244PT | g.chr3:41241105C>G | c.98C>G | p.S33C | Missense | TpC*:G | 0.846 | 0.2560 | 0.55 |
| Prevalence | CTNNB1 | catenin (cadherin-associated protein) | ENSG00000168036 | ENST00000405570 | MB246PT | g.chr3:41241105C>T | c.98C>T | p.S33F | Missense | TpC*:T | 0.808 | 0.1857 | 0.50 |
| Prevalence | CTNNB1 | catenin (cadherin-associated protein) | ENSG00000168036 | ENST00000405570 | MB249PT | g.chr3:41241105C>G | c.98C>G | p.S33C | Missense | TpC*:G | 0.846 | 0.2560 | 0.55 |
| Prevalence | CTNNB1 | catenin (cadherin-associated protein) | ENSG00000168036 | ENST00000405570 | MB252PT | g.chr3:41241105C>T | c.98C>T | p.S33F | Missense | TpC*:T | 0.808 | 0.1857 | 0.50 |
| Prevalence | MLL | myeloid/lymphoid or mixed-lineage | ENSG00000118058 | ENST00000389313 | MB116PT | g.chr11:117849403G>A | c.2319G>A | p.P773P | Synonymous | CpG*:A | . | . | . |
| Prevalence | MLL2 | myeloid/lymphoid or mixed-lineage | ENSG00000167548 | ENST00000301067 | MB127PT | g.chr12:47720881_47720882insCA15199_5199insCATCCA | fs | INDEL | Indel | 0.001 | N/A | N/A |
| Prevalence | MLL2 | myeloid/lymphoid or mixed-lineage | ENSG00000167548 | ENST00000301067 | MB135PT | g.chr12:47730019_47730018ins | c.1876_1877insG | fs | INDEL | Indel | 0.001 | N/A | N/A |

FROM FIG. 6D-1

| | | | | | | | | | |
|---|---|---|---|---|---|---|---|---|---|
| Prevalence | MLL2 | myeloid/lymphoid or mixed-lineage ENSG00000167548 ENST00000301067 | MB216PT | g.chr12:47730246C>T | c.1652C>T | p.P551L | Missense | CpG.T | 0.978 | 0.8448 | 0.95 |
| Prevalence | MLL2 | myeloid/lymphoid or mixed-lineage ENSG00000167548 ENST00000301067 | MB245PT | 12:47723130_47723147delG c.3860_3863delGACT | fs | INDEL | indel | 0.001 | N/A | N/A |
| Prevalence | MLL2 | myeloid/lymphoid or mixed-lineage ENSG00000167548 ENST00000301067 | MB246PT | g.chr12:47706474G>A | c.1390C>A | p.G4601E | Missense | G.A | 0.856 | 0.2806 | 0.60 |
| Prevalence | MLL2 | myeloid/lymphoid or mixed-lineage ENSG00000167548 ENST00000301067 | MB246PT | g.chr12:47726582dupC | c.2655dupC | fs | INDEL | indel | 0.001 | N/A | N/A |
| Prevalence | MLL2 | myeloid/lymphoid or mixed-lineage ENSG00000167548 ENST00000301067 | MB251PT | g.chr12:47722808C>T | c.4024C>T | p.Q1342X | Nonsense | C.T | 0.001 | N/A | N/A |
| Prevalence | MLL3 | myeloid/lymphoid or mixed-lineage ENSG00000055609 ENST00000262189 | MB253PT | g.chr7:151505496G>T | c.7975C>T | p.E2659X | Nonsense | G*bA.T | 0.001 | N/A | N/A |
| Prevalence | MLL3 | myeloid/lymphoid or mixed-lineage ENSG00000055609 ENST00000262189 | MB205PT | g.chr7:151509289C>T | c.6589C>T | p.Q2197X | Nonsense | TpC*.T | 0.001 | N/A | N/A |
| Prevalence | NLRP8 | NLR family, pyrin domain containin ENSG00000179709 ENST00000291971 | MB239PT | g.chr9:61165370C>T | c.2175C>T | p.A725A | Synonymous | CpG.T | . | . | . |
| Prevalence | PTCH1 | patched homolog 1 (Drosophila) | MB131PT | ns9:97258408G>T (homozyg- | c.3277G>T | p.G1093X | Nonsense | G.T | 0.001 | N/A | N/A |
| Prevalence | PTCH1 | patched homolog 1 (Drosophila) | MB158PT | g.chr9:97287809delT | c.563delT | fs | INDEL | indel | 0.001 | N/A | N/A |
| Prevalence | PTCH1 | patched homolog 1 (Drosophila) | MB203PT | chr9:97271242_97271241delK c.1862_1863delGA | fs | INDEL | indel | 0.001 | N/A | N/A |
| Prevalence | PTCH1 | patched homolog 1 (Drosophila) | MB214PT | 9:97260129_97260126dupC.c.3155_3158dupCGGC | fs | INDEL | indel | 0.001 | N/A | N/A |
| Prevalence | PTCH1 | patched homolog 1 (Drosophila) | MB214PT | chr9:97279806_97279806del | IVS14-*1delG | Splice Site | INDEL | indel | 0.324 | 0.0016 | 0.15 |
| Prevalence | PTCH1 | patched homolog 1 (Drosophila) | MB219PT | ns9:97261822T>C (homozygo | c.2760T>C | p.L928P | Missense | T.C | 0.324 | 0.0016 | 0.15 |
| Prevalence | PTCH1 | patched homolog 1 (Drosophila) | MB221PT | g.chr9:97272008delT | c.1755delT | fs | INDEL | indel | 0.001 | N/A | N/A |
| Prevalence | PTCH1 | patched homolog 1 (Drosophila) | MB221PT | g.chr9:97282158T>A | c.981T>A | p.C327X | Nonsense | T.A | 0.001 | N/A | N/A |
| Prevalence | PTCH1 | patched homolog 1 (Drosophila) | MB227PT | chr9:97270877_97270876ins | c.2227_2226insA | fs | INDEL | indel | 0.001 | N/A | N/A |
| Prevalence | PTCH1 | patched homolog 1 (Drosophila) | MB227PT | g.chr9:97260183T>A | c.3101T>A | p.Y1034E | Missense | T.A | 0.688 | 0.0721 | 0.40 |
| Prevalence | PTCH1 | patched homolog 1 (Drosophila) | MB230PT | g.chr9:97260184G>T | c.3100C>T | p.Y1034L | Missense | CpC*.T | 0.782 | 0.1497 | 0.50 |
| Prevalence | PTCH1 | patched homolog 1 (Drosophila) | MB230PT | 260164_97260165insT (hom c.3119_3120insT | fs | INDEL | indel | 0.001 | N/A | N/A |
| Prevalence | PTCH1 | patched homolog 1 (Drosophila) | MB232PT | insAGTGGTGTTCAATTTTGGTGTTGCAATTTTGCCA | fs | INDEL | indel | 0.001 | N/A | N/A |

FROM FIG. 6D-2

| | | | | | | | | | | | |
|---|---|---|---|---|---|---|---|---|---|---|---|
| Prevalence | PTCH1 | patched homolog 1 (Drosophila) | ENSG00000185920 | ENST00000375274 | MB232PT | g.chr9:97261812G>C | c.2778G>C | p.W926C | Missense | G:C | 0.472 | 0.0096 | 0.15 |
| Prevalence | PTCH1 | patched homolog 1 (Drosophila) | ENSG00000185920 | ENST00000375274 | MB232PT | g.chr9:97284091G>A (homozyg | c.707G>A | p.W236X | Nonsense | G:A | 0.001 | N/A | N/A |
| Prevalence | PTCH1 | patched homolog 1 (Drosophila) | ENSG00000185920 | ENST00000375274 | MB233PT | chr9:97263995_97263995insC (hom | c.2677_2678insC | fs | INDEL | Indel | 0.001 | N/A | N/A |
| Prevalence | PTCH1 | patched homolog 1 (Drosophila) | ENSG00000185920 | ENST00000375274 | MB247PT | chr9:97279749_97279748ins | c.1404_1405insC | fs | INDEL | Indel | 0.001 | N/A | N/A |
| Prevalence | PTCH1 | patched homolog 1 (Drosophila) | ENSG00000185920 | ENST00000375274 | MB246PT | chr9:97279926dupC (homozyg | c.2178dupC | fs | INDEL | Indel | 0.001 | N/A | N/A |
| Prevalence | PTCH1 | patched homolog 1 (Drosophila) | ENSG00000185920 | ENST00000375274 | MB251PT | g.chr9:97284109G>T | c.689C>T | p.T230I | Missense | C:T | 0.228 | 0.0008 | 0.05 |
| Prevalence | PTCH1 | patched homolog 1 (Drosophila) | ENSG00000185920 | ENST00000375274 | MB252PT | 97261128insGCCCGGGATCA/insGCCGGGATCATTG:T1052_A1053insAGIWRI | fs | INDEL | Indel | . | . | . |
| Prevalence | PTEN | phosphatase and tensin homolog | ENSG00000171862 | ENST00000371953 | MB252PT | 701994_89701995insGC (hol | c.632_633insGC | fs | INDEL | Indel | 0.001 | N/A | N/A |
| Prevalence | PTEN | phosphatase and tensin homolog | ENSG00000171862 | ENST00000371953 | MB227PT | g.chr10:89707679G>T | c.724G>T | p.E242X | Nonsense | G*pA:T | 0.001 | N/A | N/A |
| Prevalence | SMARCA4 | SWI/SNF related, matrix associated | ENSG00000127616 | ENST00000358026 | MB239PT | g.chr19:10993513C>T | c.2729C>T | p.T910M | Missense | C*pG:T | 0.694 | 0.0755 | 0.40 |
| Prevalence | SMARCA4 | SWI/SNF related, matrix associated | ENSG00000127616 | ENST00000358026 | MB231PT | g.chr19:11002492C>T | c.3469C>T | p.R1157W | Missense | C*pG:T | 0.93 | 0.5313 | 0.70 |
| Prevalence | TP53 | tumor protein p53 | ENSG00000141510 | ENST00000269305 | MB246PT | chr17:7513688_7513686delA | c.1146_1147delA | fs | INDEL | Indel | 0.001 | N/A | N/A |
| Prevalence | TP53 | tumor protein p53 | ENSG00000141510 | ENST00000269305 | MB116PT | g.chr17:7519182G>A | c.473G>A | p.R158H | Missense | CpG*:A | 0.714 | 0.0657 | 0.40 |
| Prevalence | TP53 | tumor protein p53 | ENSG00000141510 | ENST00000269305 | MB116PT | g.chr17:7519131G>A | c.524G>A | p.R175H | Missense | CpG*:A | 0.714 | 0.0657 | 0.40 |
| Prevalence | TP53 | tumor protein p53 | ENSG00000141510 | ENST00000269305 | MB159PT | g.chr17:7517576T>C | IVS3-2T>C | Splice Site | Splice site | T:C | . | . | . |
| Prevalence | TP53 | tumor protein p53 | ENSG00000141510 | ENST00000269305 | MB229PT | g.chr17:7519179C>A | c.476C>A | p.A159D | Missense | C:A | 0.628 | 0.0432 | 0.30 |

FROM FIG. 6D-3

\*Genomic positions are coordinates in the May 2004, hg17 35.1 UCSC Santa Cruz release of the human genome. Genomic coordinates and sequences of mutations are on the coding strand. All changes are heterozygous unless marked as homozygous. g., genomic sequence; c., cDNA sequence; p., protein sequence; del, deletion; dup, duplication; ins, insertion.

†Mutations in intronic sequences are annotated as intron number preceded by "IVS", with positive numbers starting from the G of the GT splice donor site and negative numbers starting from the G of the AG splice acceptor site. Mutations in untranslated regions are annotated as "UTR", with positive numbers starting at the first nucleotide after the translation start and negative numbers starting at the first nucleotide before the translation initiation.

‡fs, frameshift mutation. The amino acid change resulting from mutation of the translation-initiating methionine is indicated as "unknown".

Reference base affected by mutation is indicated to the left of the period, while the mutated base is indicated to the right of the period. Bases affected by mutation within a CpG, TpC, or GpA dinucleotide contexts are starred.

§CHASM scores are listed whenever they could be calculated (see Bioinformatics section of Supporting Online Material). Nonsense mutations, as well as small insertions or deletions that disrupt the reading frame and are likely to disrupt function, were assigned a CHASM score of "0.001", with p-values and q-values indicated as "N/A".

FIG. 6D-4 table S4. Amplifications detected by Illumina arrays

| Sample Name | Chromosome | Left Boundary (bp) | Right Boundary (bp) | Genes in amplified region | | |
|---|---|---|---|---|---|---|
| MB126PT | 1 | 73,498,586 | 73,502,199 | | | |
| MB115PT | 1 | 76,124,315 | 76,124,455 | | | |
| MB119PT | 1 | 109,116,339 | 109,116,457 | | | |
| MB129PT | 1 | 187,353,840 | 187,354,239 | | | |
| MB126PT | 1 | 194,888,508 | 194,889,123 | | | |
| MB119PT | 2 | 4,294,508 | 4,296,276 | | | |
| MB123PT | 2 | 4,294,508 | 4,296,851 | | | |
| MB123PT | 2 | 15,572,120 | 15,576,003 | | | |
| MB123PT | 2 | 21,977,080 | 21,986,805 | | | |
| MB117PT | 2 | 36,263,684 | 36,263,792 | | | |
| MB118PT | 2 | 36,263,684 | 36,264,162 | | | |
| MB122PT | 3 | 3,568,124 | 3,839,892 | | | |
| MB122PT | 3 | 4,918,652 | 4,954,672 | | | |
| MB122PT | 3 | 36,318,274 | 36,323,972 | | | |
| MB125PT | 3 | 38,350,561 | 38,595,911 | ACVR2B | EXOG | XYLB |
| MB125PT | 3 | 38,606,427 | 38,623,066 | | | |
| MB125PT | 3 | 38,841,595 | 38,980,893 | SCN11A | SCN11A | |
| MB119PT | 5 | 46,269,585 | 46,293,747 | | | |
| MB119PT | 5 | 46,376,015 | 46,435,031 | | | |
| MB124PT | 5 | 46,396,362 | 46,435,031 | | | |
| MB126PT | 5 | 66,657,904 | 66,658,684 | | | |
| MB126PT | 6 | 58,860,048 | 58,870,153 | | | |
| MB126PT | 6 | 62,278,668 | 62,281,216 | | | |
| MB115PT | 6 | 141,457,859 | 141,471,756 | | | |
| MB126PT | 6 | 161,189,087 | 161,198,759 | | | |
| MB119PT | 7 | 57,952,346 | 58,019,815 | | | |
| MB126PT | 7 | 61,750,446 | 61,752,935 | | | |
| MB119PT | 7 | 89,392,191 | 89,392,415 | | | |

FROM FIG. 7A-1

| | | | | | |
|---|---|---|---|---|---|
| MB122PT | 7 | 90,314,769 | 90,358,033 | | |
| MB122PT | 7 | 90,427,687 | 90,447,959 | | |
| MB122PT | 7 | 91,617,907 | 91,865,123 | KRIT1 | hsa-mir-1285-1 |
| MB122PT | 7 | 92,071,300 | 92,405,407 | CDK6 | ENSG00000214343 |
| MB122PT | 7 | 105,586,909 | 105,683,978 | | |
| MB115PT | 8 | 83,355,282 | 83,357,609 | | |
| MB115PT | 8 | 112,118,351 | 112,135,976 | | |
| MB115PT | 8 | 112,203,634 | 112,226,716 | | |
| MB115PT | 8 | 118,797,555 | 118,797,995 | | |
| MB104X | 8 | 128,169,258 | 128,859,798 | MYC* | |
| MB103X | 8 | 128,232,156 | 128,826,532 | MYC* | POU5F1B |
| MB101X | 8 | 128,376,264 | 128,871,130 | MYC* | POU5F1B |
| MB115PT | 8 | 130,577,823 | 130,579,250 | | |
| MB115PT | 8 | 141,189,636 | 141,189,852 | | |
| MB124PT | 9 | 17,342,284 | 17,347,818 | | |
| MB126PT | 10 | 38,815,211 | 38,909,744 | | |
| MB126PT | 10 | 42,114,131 | 42,130,982 | | |
| MB119PT | 11 | 48,675,981 | 48,693,749 | | |
| MB126PT | 11 | 48,690,435 | 48,852,229 | | |
| MB119PT | 11 | 48,899,658 | 48,911,561 | | |
| MB126PT | 11 | 50,372,569 | 50,967,257 | | |
| MB123PT | 11 | 54,591,779 | 54,620,503 | | |
| MB126PT | 11 | 121,392,786 | 121,393,004 | | |
| MB124PT | 11 | 130,640,244 | 130,640,250 | | |
| MB124PT | 12 | 36,524,940 | 36,544,404 | | |
| MB117PT | 12 | 95,744,009 | 95,745,411 | | |
| MB126PT | 13 | 68,556,977 | 68,557,913 | | |
| MB126PT | 13 | 71,206,551 | 71,206,565 | | |

FIG. 7A-2

| | | | | | |
|---|---|---|---|---|---|
| MB126PT | 13 | 113,077,676 | 113,078,124 | | |
| MB126PT | 13 | 113,816,493 | 113,816,604 | | |
| MB103X | 14 | 54,674,688 | 54,687,597 | | |
| MB103X | 14 | 54,961,082 | 54,972,295 | | |
| MB103X | 14 | 55,173,625 | 55,243,440 | | |
| MB103X | 14 | 55,957,690 | 56,626,651 | OTX2 | C14orf101 |
| MB101X | 14 | 56,284,434 | 56,469,542 | OTX2 | |
| MB103X | 14 | 73,021,163 | 73,023,157 | | |
| MB103X | 14 | 73,622,800 | 73,752,126 | | |
| MB103X | 14 | 73,878,908 | 73,885,423 | | |
| MB126PT | 15 | 29,590,148 | 29,590,614 | | |
| MB119PT | 16 | 33,889,259 | 33,892,284 | | |
| MB126PT | 16 | 35,054,181 | 35,143,083 | | |
| MB119PT | 16 | 35,062,145 | 35,141,900 | | |
| MB101X | 17 | 45,598,438 | 45,598,439 | | |
| MB126PT | 17 | 73,357,711 | 73,358,373 | | |
| MB126PT | 18 | 44,290,789 | 44,291,672 | | |
| MB120PT | 20 | 26,227,758 | 26,248,774 | | |
| MB119PT | 20 | 26,227,758 | 26,266,279 | | |
| MB126PT | 20 | 26,247,677 | 26,257,255 | | |
| MB124PT | 21 | 33,615,748 | 33,615,750 | | |
| MB120PT | X | 58,506,270 | 58,539,303 | | |

*Boundaries for the MYC amplicon were determined by visual inspection of chromosome 8q LogR ratio values.

FIG. 7B table S5. Homozygous deletions detected by Illumina arrays

| Sample Name | Chromosome | Left Boundary (bp) | Right Boundary (bp) | Genes in region of homozygous deletion |
|---|---|---|---|---|
| MB121PT | 1 | 26,333,039 | 26,333,369 | |
| MB124PT | 1 | 112,496,243 | 112,497,197 | |
| MB122PT | 1 | 167,495,768 | 167,505,182 | |
| MB113PT | 1 | 220,443,401 | 220,443,721 | |
| MB109PT | 2 | 34,554,235 | 34,582,939 | |
| MB106X | 2 | 44,320,871 | 44,321,576 | |
| MB117PT | 2 | 51,780,103 | 51,781,218 | |
| MB118PT | 2 | 53,412,341 | 53,412,983 | |
| MB117PT | 2 | 59,477,152 | 59,479,126 | |
| MB125PT | 2 | 116,378,779 | 116,379,089 | |
| MB126PT | 2 | 123,197,294 | 123,198,771 | |
| MB109PT | 2 | 208,061,364 | 208,066,083 | |
| MB101X | 3 | 5,235,444 | 5,235,445 | |
| MB103X | 3 | 5,511,975 | 5,513,017 | |
| MB119PT | 3 | 53,003,023 | 53,013,826 | |
| MB104X | 3 | 118,020,423 | 118,033,312 | |
| MB117PT | 3 | 131,271,881 | 131,273,585 | |
| MB108C | 3 | 150,446,085 | 150,450,025 | |
| MB103X | 3 | 176,564,661 | 176,566,093 | |
| MB108C | 3 | 178,777,909 | 178,779,579 | |
| MB129PT | 4 | 34,469,747 | 34,499,424 | |
| MB105X | 4 | 63,352,170 | 63,357,704 | |
| MB126PT | 4 | 64,380,191 | 64,389,207 | |
| MB101X | 4 | 69,126,340 | 69,163,188 | |
| MB129PT | 4 | 69,126,340 | 69,173,198 | |
| MB106X | 4 | 107,823,784 | 107,828,236 | |
| MB128PT | 4 | 123,883,878 | 123,883,895 | BBS12 |
| MB115PT | 4 | 138,312,400 | 138,316,899 | |

FROM FIG. 8A-1

| | | | | |
|---|---|---|---|---|
| MB124PT | 5 | 126,262,789 | 126,265,682 | |
| MB117PT | 5 | 170,062,869 | 170,063,295 | |
| MB119PT | 5 | 180,309,991 | 180,327,250 | BTNL8 |
| MB121PT | 6 | 31,388,080 | 31,391,583 | |
| MB121PT | 6 | 31,394,226 | 31,396,472 | |
| MB118PT | 6 | 31,468,234 | 31,470,909 | |
| MB118PT | 6 | 31,473,287 | 31,475,344 | |
| MB118PT | 6 | 31,479,080 | 31,488,428 | MICA |
| MB118PT | 6 | 31,491,050 | 31,505,856 | |
| MB118PT | 6 | 31,510,389 | 31,540,766 | HCP5 |
| MB118PT | 6 | 31,542,600 | 31,543,848 | |
| MB118PT | 6 | 31,544,455 | 31,559,659 | |
| MB119PT | 6 | 32,561,832 | 32,563,460 | |
| MB105X | 6 | 32,565,228 | 32,567,470 | |
| MB118PT | 6 | 32,746,293 | 32,748,314 | HLA-DQB1 |
| MB101X | 6 | 55,934,096 | 55,954,486 | |
| MB130PT | 6 | 77,498,434 | 77,510,033 | |
| MB130PT | 6 | 79,029,649 | 79,090,197 | |
| MB117PT | 6 | 132,752,524 | 132,754,000 | |
| MB105X | 6 | 139,645,437 | 139,648,424 | |
| MB121PT | 7 | 91,196,567 | 91,196,798 | |
| MB105X | 7 | 109,970,858 | 109,972,221 | |
| MB129PT | 7 | 133,437,483 | 133,444,091 | |
| MB129PT | 7 | 141,420,759 | 141,439,888 | MGAM |

FIG. 8A-2

| | | | | | | |
|---|---|---|---|---|---|---|
| MB104X | 7 | 146,240,646 | 146,338,977 | | | |
| MB101X | 8 | 2,243,942 | 2,249,691 | | | |
| MB101X | 8 | 5,583,199 | 5,592,495 | | | |
| MB118PT | 8 | 16,246,032 | 16,250,206 | | | |
| MB119PT | 8 | 17,782,521 | 17,782,529 | | | |
| MB119PT | 8 | 17,795,520 | 17,796,446 | | | |
| MB125PT | 8 | 25,032,788 | 25,040,703 | | | |
| MB124PT | 8 | 33,623,983 | 33,649,641 | | | |
| MB105X | 8 | 39,351,896 | 39,499,553 | ADAM3A | ADAM5P | |
| MB124PT | 8 | 51,389,781 | 51,390,731 | | | |
| MB124PT | 8 | 68,155,973 | 68,155,974 | | | |
| MB109PT | 8 | 85,420,095 | 85,430,101 | | | |
| MB105X | 8 | 138,891,980 | 138,894,551 | | | |
| MB103X | 9 | 28,039,518 | 28,040,777 | | | |
| MB123PT | 9 | 77,195,075 | 77,198,036 | | | |
| MB108C | 9 | 84,562,724 | 84,571,840 | | | |
| MB117PT | 9 | 106,636,026 | 106,636,232 | | | |
| MB104X | 9 | 128,560,616 | 128,561,879 | | | |
| MB108C | 9 | 132,070,572 | 132,073,252 | | | |
| MB124PT | 9 | 137,335,024 | 137,335,350 | | | |
| MB124PT | 9 | 139,593,550 | 139,632,376 | ARRDC1 | C9orf37 | ZMYND19 |
| MB124PT | 9 | 139,635,696 | 139,732,818 | EHMT1 | | |
| MB124PT | 9 | 139,744,619 | 139,770,293 | EHMT1 | | |
| MB109PT | 10 | 17,998,747 | 17,999,193 | | | |
| MB109PT | 10 | 20,890,630 | 20,897,371 | | | |
| MB106X | 10 | 53,686,068 | 53,686,625 | | | |
| MB109PT | 10 | 69,738,803 | 69,739,239 | | | |
| MB106X | 10 | 94,192,885 | 94,194,314 | | | |
| MB105X | 10 | 124,341,161 | 124,341,587 | DMBT1 | | |

FROM FIG. 8B-1

| | | | | | | | |
|---|---|---|---|---|---|---|---|
| MB129PT | 11 | 1,611,186 | 1,611,326 | | | | |
| MB126PT | 11 | 7,771,230 | 7,785,071 | OR5P2 | | | |
| MB108C | 11 | 41,774,842 | 41,774,946 | | | | |
| MB124PT | 11 | 55,124,465 | 55,209,499 | OR4C11 | OR4C6 | OR4P1P | OR4P4 OR4S2 |
| MB106X | 11 | 92,663,030 | 92,668,588 | | | | |
| MB122PT | 11 | 93,323,328 | 93,325,650 | | | | |
| MB106X | 11 | 101,740,351 | 101,781,327 | BIRC2 | TMEM123 | | |
| MB109PT | 12 | 12,424,251 | 12,433,136 | | | | |
| MB103X | 12 | 33,192,424 | 33,197,122 | | | | |
| MB103X | 12 | 43,994,210 | 43,996,497 | | | | |
| MB103X | 12 | 51,372,912 | 51,373,716 | KRT77 | | | |
| MB109PT | 12 | 98,319,260 | 98,326,639 | | | | |
| MB103X | 12 | 110,462,766 | 110,463,443 | | | | |
| MB109PT | 13 | 113,607,766 | 113,607,861 | | | | |
| MB130PT | 14 | 34,675,767 | 34,677,673 | | | | |
| MB105X | 14 | 34,675,767 | 34,683,370 | | | | |
| MB115PT | 16 | 6,897,924 | 6,897,941 | | | | |
| MB109PT | 16 | 65,645,146 | 65,645,422 | | | | |
| MB115PT | 16 | 83,860,208 | 83,861,626 | | | | |
| MB103X | 16 | 84,094,051 | 84,247,154 | KIAA0182 | | | |
| MB126PT | 17 | 854,657 | 854,657 | | | | |
| MB115PT | 17 | 1,156,618 | 1,156,739 | | | | |
| MB104X | 17 | 15,124,352 | 15,126,210 | | | | |
| MB126PT | 18 | 14,540,022 | 14,540,375 | | | | |
| MB122PT | 18 | 62,058,882 | 62,062,341 | | | | |
| MB109PT | 18 | 75,641,247 | 75,641,332 | | | | |
| MB101X | 19 | 6,641,744 | 6,641,746 | | | | |
| MB123PT | 19 | 33,606,515 | 33,606,816 | | | | |
| MB104X | 19 | 40,548,765 | 40,553,535 | | | | |

FIG. 8B-2

| | | | | |
|---|---|---|---|---|
| MB121PT | 19 | 41,534,966 | 41,535,932 | |
| MB108C | 20 | 1,507,026 | 1,524,714 | SIRPB1 |
| MB125PT | 20 | 51,722,131 | 51,722,650 | |
| MB118PT | 21 | 22,576,805 | 22,583,706 | |
| MB120PT | 22 | 21,808,695¹ | 21,809,273 | |
| MB117PT | 22 | 37,693,776 | 37,707,428 | |
| MB123PT | 22 | 37,768,259 | 37,768,263 | |
| MB105X | X | 46,240,765 | 46,240,983 | |
| MB104X | X | 47,216,035 | 47,218,450 | |
| MB103X | X | 63,264,193 | 63,266,226 | |
| MB123PT | X | 82,085,957 | 82,093,891 | |
| MB128PT | X | 89,780,570 | 89,785,073 | |
| MB108C | X | 111,600,829 | 111,629,152 | |
| MB108C | X | 128,148,291 | 128,154,647 | |
| MB117PT | X | 153,075,038 | 153,075,046 | OPN1LW |

FIG. 8C table S6. Candidate gene sets enriched for genetic alterations in medulloblastomas

| Gene Set | Pathway database | Set size | Number of mutations in set | Number of deletions in set | Number of amplifications in set | Number of samples with mutations, amplifications, or deletions | Statistical significance of altered genes in set | Altered genes (with the number of alterations) | | | | |
|---|---|---|---|---|---|---|---|---|---|---|---|---|
| chromatin-mediated maintenance of transcription | GO | 5 | 6 | 0 | 0 | 6 | <0.001 | ARID1A (1) | MLL2 (5) | | | |
| Signal transduction_ESR1-nuclear pathway | GS | 236 | 10 | 0 | 3 | 12 | <0.001 | ADCY9 (1) | ARID1A (1) | MLL2 (5) | MYC (3) | SMARCA4 (1) TP53 (1) UBE2D2 (1) |
| induction of apoptosis by intracellular signals | GO | 17 | 2 | 0 | 3 | 5 | <0.001 | CUL4A (1) | MYC (3) | TP53 (1) | | |
| positive regulation of epithelial cell differentiation | GO | 4 | 2 | 1 | 0 | 3 | 0.003 | CTNNB1 (1) | DMBT1 (1) | PAX6 (1) | | |
| skeletal morphogenesis | GO | 13 | 0 | 0 | 4 | 4 | 0.003 | ACVR2B (1) | MYC (3) | | | |
| Development_Role Activin A in cell differentiation and proliferation | MA | 32 | 2 | 0 | 4 | 6 | 0.003 | ACVR2B (1) | ADCY9 (1) | FSHR (1) | MYC (3) | |
| negative regulation of survival gene product expression | GO | 5 | 0 | 0 | 3 | 3 | 0.004 | MYC (3) | | | | |
| transcription initiation | GO | 16 | 1 | 0 | 3 | 4 | 0.004 | MYC (3) | TAF1L (1) | | | |
| Signal transduction_AKT signaling | MA | 61 | 4 | 0 | 3 | 6 | 0.005 | MYC (3) | PTEN (1) | TP53 (1) | | |
| release of cytochrome c from mitochondria | GO | 18 | 1 | 0 | 3 | 4 | 0.006 | MYC (3) | TP53 (1) | | | |
| regulation of smoothened signaling pathway | GO | 6 | 2 | 0 | 2 | 3 | 0.006 | OTX2 (2) | PTCH1 (2) | | | |
| gastrulation with mouth forming second | GO | 25 | 3 | 0 | 1 | 4 | 0.01 | ACVR2B (1) | CTNNB1 (1) | LHX1 (1) | LRP6 (1) | |
| Development_Regulation of angiogenesis | GS | 300 | 9 | 0 | 3 | 10 | 0.01 | AGGF1 (1) | CTNNB1 (1) | EPHA2 (1) | MAPK7 (1) | MYC (3) NTSR1 (1) OPRM1 (1) PKD1 (1) PTCH1 (2) |
| Development_WNT signaling pathway, Part 2 | MA | 83 | 3 | 0 | 3 | 6 | 0.01 | CTNNB1 (1) | MYC (3) | REST (1) | SMARCA4 (1) | |
| protein processing | GO | 24 | 2 | 0 | 3 | 4 | 0.01 | MYC (3) | PTCH1 (2) | | | |
| detection of mechanical stimulus involved in sensory perception of s | GO | 8 | 0 | 0 | 3 | 3 | 0.011 | MYC (3) | | | | |
| middle ear morphogenesis | GO | 8 | 0 | 0 | 3 | 3 | 0.011 | MYC (3) | | | | |

FROM FIG. 9B

FROM FIG. 9D

| | | | | | | | | | | | | |
|---|---|---|---|---|---|---|---|---|---|---|---|---|
| Signal Transduction_Cholecystokinin signaling | GG | 198 | 3 | 0 | 3 | 6 | 0.191 | ADCY9(1) | MYC(3) | NTSR1(1) | OPRM1(1) | |
| dendrite morphogenesis | GO | 12 | 2 | 0 | 0 | 2 | 0.192 | KLF7(1) | TG(1) | | | |
| Development_Blood vessel morphogenesis | GG | 336 | 7 | 0 | 3 | 8 | 0.193 | CTNNB1(1) | CYR61(1) | JAG1(1) | MAPK7(1) | MYC(3) | NOTCH4(1) NTSR1(1) OPRM1(1) |
| Development_PDGF signaling via STATs and NF-kB | MA | 41 | 0 | 1 | 3 | 3 | 0.193 | MYC(3) | | | | |

FIG. 9E table S7. Discovery Screen mutations and patient age

| Sample[*] | Patient age (years) | Number of Sequence Alterations[+] | Number of Sequence and Copy Number Alterations[+] |
|---|---|---|---|
| MB122PT | 13.5 | 18 | 20 |
| MB126PT | 10.9 | 16 | 17 |
| MB125PT | 10.7 | 6 | 8 |
| MB118PT | 9.2 | 9 | 12 |
| MB124PT | 8.9 | 10 | 14 |
| MB113PT | 8.2 | 4 | 4 |
| MB128PT | 6.0 | 4 | 5 |
| MB111PT | 5.2 | 5 | 5 |
| MB115PT | 5.0 | 17 | 17 |
| MB119PT | 4.5 | 3 | 4 |
| MB123PT | 4.3 | 4 | 4 |
| MB120PT | 3.4 | 5 | 5 |
| MB109PT | 2.7 | 5 | 5 |
| MB121PT | 2.1 | 1 | 1 |
| MB117PT | 2.1 | 3 | 4 |

[*]Only primary tumor samples from non-recurrent MBs in patients of known age (n=15) were included.

[+]Sequence alterations included non-silent (NS) and silent (S) changes; Copy number alterations incldued focal amplifications and homozygous deletions.

FIG. 10 table S8. *CAN*-gene mutations and patient age in Discovery and Prevalence screens

| | MB patient age* | | |
|---|---|---|---|
| *CAN*-gene alteration | < 5 years | 5-14 years | > 14 years |
| *PTCH1* mutation | 3/11 (27%) | 0/38 (0%) | 10/21 (48%) |
| *MLL2/MLL3* mutation | 0/11 (0%) | 8/38 (21%) | 3/21 (14%) |
| *CTNNB1* mutation | 0/11 (0%) | 5/38 (13%) | 6/21 (29%) |
| Any *CAN*-gene altered | 3/11 (27%) | 12/38 (32%) | 16/21 (76%) |

*Patient age refers to age at which the MB sample was obtained. Only primary tumor samples (n=70) from non-recurrent MBs in patients of known age at diagnosis were included: 11 patients < 5 years, 38 patients 5-14 years, 21 patients > 14 years.

FIG. 11 table S9. Mutations of *PTCH1*, *MLL2/MLL3*, *CTNNB1* and MB subtype

|  | MB subtype | | |
| --- | --- | --- | --- |
|  | Large cell / anaplastic | Nodular / desmoplastic | Classic, non-nodular |
| *PTCH1* | 3/11 (27%) | 5/10 (50%) | 6/53 (11%) |
| *MLL2/MLL3* | 4/11 (36%) | 1/10 (10%) | 6/53 (11%) |
| *CTNNB1* | 1/11 (9%) | 0/10 (0%) | 10/53 (19%) |

Only tumors (n=74) that underwent central pathologic review were included: 11 large cell/anaplastic MBs, 10 nodular/desmoplastic MBs, and 53 classic MBs.

FIG. 12

MEDULLOBLASTOMA GENES AS TARGETS FOR DIAGNOSIS AND THERAPEUTICS

This invention was made using funds from the U.S. National Institutes of Health. The U.S. government therefore retains certain rights in the invention according to the terms of grant nos. CA 57345 and CA 121113.

TECHNICAL FIELD OF THE INVENTION

This invention is related to the area of cancer diagnosis, therapeutics, and theranostics. In particular, it relates to childhood cancers.

BACKGROUND OF THE INVENTION

Medulloblastomas (MBs) originate in the cerebellum and have a propensity to disseminate throughout the central nervous system (1). Although aggressive multimodal therapy has improved the prognosis for children with MB, a significant proportion of patients are currently incurable (2). Moreover, survivors often suffer significant treatment-related morbidities, including neurocognitive deficits related to radiation therapy. New insights into the pathogenesis of these tumors are therefore sorely needed. Gene-based research has identified two subgroups of MBs, one associated with mutated genes within the sonic hedgehog pathway and the other associated with altered Wnt pathway genes (3, 4). Amplifications of MYC and OTX2 (5-7), mutations in TP53 (8), and a number of chromosomal alterations have also been identified in MBs. These discoveries have helped define the pathogenesis of MB and have improved our ability to identify patients who might benefit from therapies targeting these pathways. However, most MB patients do not have alterations in these genes and the compendium of genetic alterations causing MB is unknown.

There is a continuing need in the art to obtain improved tools for diagnosing, treating, and predicting the course of brain tumors; childhood tumors, and medulloblastomas.

SUMMARY OF THE INVENTION

One aspect of the invention is a method for diagnosing medulloblastoma in a human. A somatic mutation in a gene or its encoded mRNA, cDNA, or protein is determined in a test sample relative to a normal sample of the human. The gene is selected from the group consisting of those listed in Table S3, S4, S5, or 2. When a somatic mutation is determined the sample is identified as a medulloblastoma.

Another aspect of the invention is a method to stratify medulloblastomas for testing candidate or known anti-cancer therapeutics. A CAN-gene mutational signature is determined for a medulloblastoma by determining at least one somatic mutation in a test sample relative to a normal sample of a human. The at least one somatic mutation is in one or more genes selected from the group consisting of Table S3, S4, S5, or 2. A first group of medulloblastomas that have the CAN-gene mutational signature is formed. Efficacy of a candidate or known anti-cancer therapeutic on the first group is compared to efficacy on a second group of medulloblastomas that has a different CAN-gene mutational signature. A CAN gene mutational signature which correlates with increased or decreased efficacy of the candidate or known anti-cancer therapeutic relative to other groups is thereby identified.

An additional aspect of the invention is a method of characterizing a medulloblastoma in a human. A somatic mutation in a gene or its encoded mRNA, cDNA, or protein is determined in a test sample relative to a normal sample of the human. The gene is selected from the group consisting of those listed in Table S3, S4, S5, or 2

Yet another aspect of the invention is method of classifying a medulloblastoma tumor. A sample of the medulloblastoma is tested for a mutation in MLL2 or MLL3 gene or its encoded mRNA, cDNA, or protein. The medulloblastoma is classified into a group that shares its MLL2 or MLL3 mutation status.

Still another aspect of the invention is a method of treating a medulloblastoma in a human. A wild-type human MLL2 or MLL3 coding sequence is administered to a patient with a mutation in MLL2 or MLL3 in its medulloblastoma. The wild-type coding sequence is thereby expressed.

Yet another aspect of the invention is a method of detecting a medulloblastoma in a human. A blood sample of the human is tested for the presence of a mutant MLL2 or MLL3 coding sequence. The presence of the sequence indicates a medulloblastoma in the human.

A further aspect of the invention is a method of treating a medulloblastoma in a human. A wild-type human coding sequence of a gene selected from the group consisting of those listed in Table S3, S4, S5, or 2 is provided to a patient with a mutation in the gene in its medulloblastoma. The coding sequence is thereby expressed.

Still another aspect of the invention is a method of detecting a medulloblastoma in a human. A blood sample of the human is tested for the presence of a mutant coding sequence of a gene selected from the group consisting of those listed in Table S3, S4, S5, or 2. The presence of the mutant coding sequence indicates a medulloblastoma in the human.

These and other embodiments which will be apparent to those of skill in the art upon reading the specification provide the art with methods for detecting, diagnosing, categorizing, and treating medulloblastomas.

BRIEF DESCRIPTION OF THE DRAWINGS

FIG. 4A-4D. (Table S1.) Primers used in medulloblastoma Discovery and Prevalence Screen. Forward Primers are consecutively SEQ ID NO: 1-67. Reverse Primers are consecutively SEQ ID NO: 68-134. M13 universal sequencing primer is SEQ ID NO: 135.

FIG. 5 (Table S2). Characteristics of medulloblastoma samples used in Discovery and Prevalence Screens FIG. 6 (Table S3.) Somatic mutations in medulloblastoma Discovery and Prevalence Screen FIG. 7 (Table S4.) Amplifications detected by Illumina arrays FIG. 8 (Table S5.) Homozygous deletions detected by Illumina arrays FIG. 9 (Table S6.) Candidate gene sets enriched for genetic alterations in medulloblastomas FIG. 10 (Table S7.) Discovery Screen mutations and patient age FIG. 11 (Table S8.) CAN-gene mutations and patient age in Discovery and Prevalence Screens FIG. 12 (Table S9.) CAN-gene mutations and histologic subtype

DETAILED DESCRIPTION OF THE INVENTION

Figure 1:
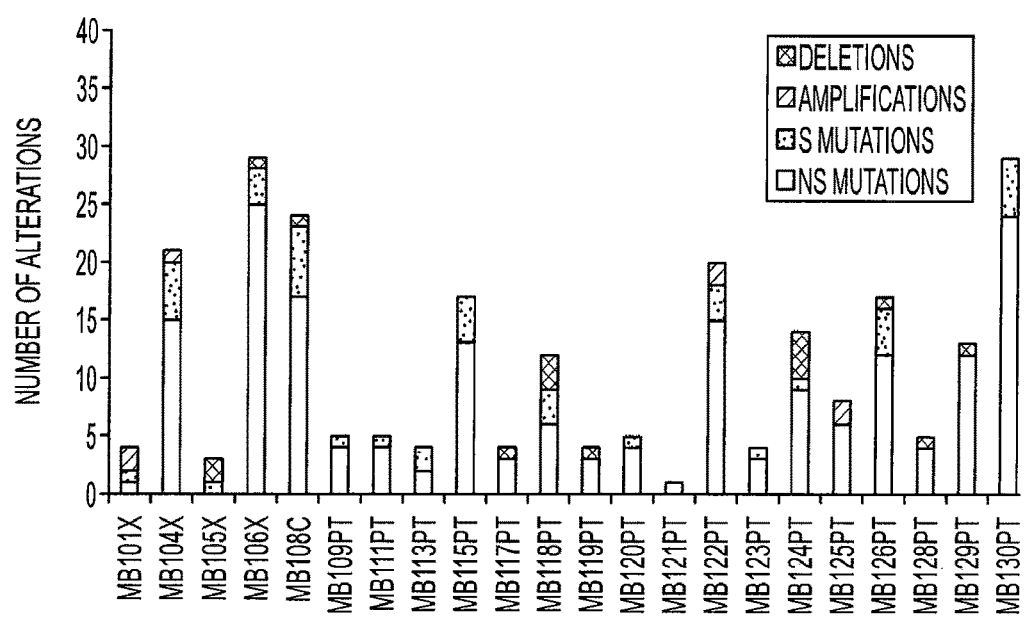
FIG. 1. Number of genetic alterations detected through sequencing and copy number analyses in each of the 22 cancers. NS, non-silent mutations (including non-synonymous alterations, insertions, duplications, deletions, and splice site changes); S, silent mutations; Deletions, gene-containing regions absent in tumor samples; Amplifications, gene-containing regions focally amplified at levels >10 copies per nucleus (21).

The inventors have developed a comprehensive genetic overview of medulloblastomas. The inventors found that medulloblastomas contain far fewer mutations than adult tumors, but a larger proportion of the mutations are nonsense, insertion, deletion, and duplication mutations. The most frequently mutated genes in the samples studies included two that have not been previously identified with medulloblastoma, MLL2 and MLL3. Mutations in these genes are inactivating mutations of histone H3K4 trimethylases, enzymes involved in chromatin remodeling and transcriptional regulation. Other genes found mutated involved in the same pathway as the MLL2 and MLL3 genes include SMARCA4 and ARID1A, in which mutations have also been found.

These data provide the first comprehensive view of a solid tumor arising in children. The most impressive difference between this tumor type and those affecting adults is the number of genetic alterations observed. This result could not have been predicted on the basis of prior evidence (27). In fact, at the karyotypic level, the incidence of chromosomal changes in MBs is often described as high as that in adult solid tumors (reviewed in (27)).

What does the smaller number of mutations reveal about the tumorigenesis of MBs? Most mutations observed in adult tumors are predicted to be passenger alterations (19). Passenger mutations provide an evolutionary clock that precisely records the number of divisions that a cell has undergone during both normal development and tumor progression. Therefore, the cell division number is linearly related to the number of passenger mutations detected in a tumor (28). This concept is consistent with the positive correlation we identified between increasing patient age and the number of mutations found in their MBs. This relationship was observed for both the mutations detected in the exomes of the Discovery Screen tumors (r=0.73, p<0.01) as well as the number of alterations observed in the subset of 15 genes analyzed in the Discovery and Prevalence Screen samples (r=0.32, p<0.01) (tables S7 and S8). Even if we assume that all but one of the mutations in each MB is a passenger, the number of passenger mutations in MBs is still substantially smaller than the number of passenger mutations in adult solid tumors (16-19). The smaller number of passenger mutations in MBs implies that a smaller number of cell divisions is required to reach clinically-detectable tumor size in MBs. Theoretically, this could be due to one of three factors: the number of tumor cells required for clinical detection could be lower, the net tumor cell proliferation rate in tumors could be higher, or the number of driver mutations needed for tumor formation could be lower. The first two possibilities can be excluded; the size of MBs is not notably different than that of other tumors, particularly glioblastoma multiforme, and the cell division time of MBs is not much different from that of other tumors (29). These data therefore suggest that fewer driver mutations are required for MB tumorigenesis and that driver mutations in MB confer a greater selective advantage than those of adult solid tumors. It is interesting to note that adult leukemias also appear to harbor a relatively small number of somatic alterations (11, 15) and that both leukemias and MBs are more responsive to chemotherapy than most adult solid tumors. How the number of alterations affects response to therapy remains a subject for future research. Additionally, it will be informative to determine whether a smaller number of mutations is characteristic of all pediatric solid tumors.

Previously, most insights into the molecular basis of MB emerged from the study of hereditary tumor syndromes (27), including Gorlin Syndrome, caused by germline mutations of PTCH1, Turcot Syndrome, caused by germline mutations of APC, and the Li-Fraumeni Syndrome, caused by germline mutations of TP53. In our study, we found both PTCH1 and TP53 to be somatically mutated in MBs (tables 2 and S3), at frequencies similar to those observed in earlier studies. We also identified amplifications of MYC and OTX2, both previously implicated in MB (6, 7).

The ability to investigate the sequence of all coding genes in MBs has also revealed mutated genes not previously implicated in MBs (table S3). Among these, MLL2 and MLL3 were of greatest interest, as the frequency of inactivating mutations unequivocally establishes them as MB tumor suppressor genes. This genetic evidence is consistent with functional studies showing that knock-out of murine MLL3 results in ureteral epithelial cancers (30). These genes are large and have been reported in the COSMIC database to be altered in occasional cancers, but not at a sufficiently high frequency to distinguish them from passenger alterations (and with no evidence of a high fraction of inactivating mutations) (31).

The general role of genes controlling histone methylation has become increasingly recognized as a common feature of human cancers. For example, inactivating mutations of the histone H3K27 demethylase gene UTX have been observed in multiple myelomas, esophageal cancers and renal cell cancers (32). In addition, a small fraction of renal cell cancers contain mutations in the histone methyltransferase gene SETD2 and the histone demethylase gene JARID1C (33), and the histone methyltransferase gene EZH2 has been found to be mutated in non-Hodgkin's lymphomas (34). Most recently, frequent mutations of the chromatin remodeling gene ARID1A have been discovered in ovarian clear cell carcinomas (20, 35); of note, one ARID1A mutation was discovered in our MB patients (table S3). A link between histone methylation genes (although not MLL2 or MLL3) and MB has also previously been hypothesized based on the observation that copy number alterations affecting chromosomal regions containing histone methyltransferases or demethylases occur in a subset of MBs (36).

The mechanism(s) through which MLL genes contribute to tumorigenesis are not known but some clues can be gleaned from the literature. The MLL family of histone H3K4 trimethylases includes seven genes (MLL1, MLL2, MLL3, MLL4, MLL5, SET1A and SET1B) (37). MLL-family genes have been shown to regulate HOX gene expression (38, 39), and an attractive possibility is that they normally down-regulate OTX2, an MB oncogene (6, 7, 40).

Another possibility is suggested by the observation that β-catenin brings MLL complexes to the enhancers of genes regulating the Wnt pathway, thereby activating their expression (41). A third possibility is that MLL family genes are important for transcriptional regulation of normal brain development and differentiation (42) and their disruption may lead to aberrant proliferation of precursor cells.

The identification of MLL2 and MLL3 as novel and frequently-inactivated MB genes supports the concept that MB is fundamentally characterized by dysregulation of core developmental pathways (43). Although alterations of classic cancer genes (e.g. TP53, MYC, and PTEN) were identified in these childhood tumors, our sequence analysis demonstrated that mutations of genes involved in normal developmental processes, such as MLL family genes and Hedgehog and Wnt pathway genes, were much more frequent. The fact that a relatively small number of somatic mutations is sufficient for MB pathogenesis as compared to adult solid tumors provides further evidence that the temporally-restricted subversion of normal cerebellar development is critical in the development of these tumors. This is consistent with the observation that the incidence of MB decreases significantly after childhood, with the tumors becoming quite rare after the age of 40 years (1). It will be interesting to determine if genetic alterations in developmental pathways are a key feature of all childhood malignancies.

The development of an improved classification system for MB that could be used to guide targeted risk-adapted therapy to patients is a primary goal of current MB research. The designation of specific histologic subtypes of MB has proven to be of some prognostic value. For example, large-cell/anaplastic MBs, which are aggressive tumors often associated with MYC amplification, carry a relatively poor prognosis (44), while desmoplastic MBs, which frequently have alterations of PTCH1 or other Hedgehog pathway genes (4), are more easily treatable. However, molecular studies have revealed that these histologic subtypes are biologically heterogeneous (3); in addition, most MBs are of the classic subtype and do not have defining molecular alterations. Our results add an additional layer of complexity to these classifications. Although activation of the Wnt and Hedgehog pathways are generally considered to define two MB subtypes (3), our data revealed that these groups overlap, as two adult MBs were found to contain mutations of both PTCH1 and CTNNB1 (tables S2 and S3). Similarly, MLL2/MLL3 mutations were identified in both pediatric and adult MBs (table S8), were not exclusive to any histologic subtype (although they were most common in large-cell/anaplastic MBs (table S2 and S9), and were occasionally found in tumors with PTCH1 or CTNNB1 mutations (tables S2, S3). Further studies of these genes in larger number of MBs that have been analyzed for pathologic subtypes will be needed to clarify the molecular classification of this tumor.

We conclude that each MB is driven by a small number of driver mutations, and in our cohort, the most commonly altered gene-set included MLL2. However, there are several limitations to our study. Though in a few cases we have identified two or three bona fide cancer genes that are mutated in individual MBs, other cases show no mutations of any known cancer gene, and only one alteration of any gene (FIG. 1. and table S3). Several explanations for the relative absence of genetic alterations in occasional MBs can be offered. First, despite the use of classic Sanger sequencing, a small fraction of the exome cannot be examined, either because of a very high GC content or of homology to highly related genes. Second, it is possible that mutations in the non-coding regions of the genome could occur and these would not be detected. Third, copy-neutral genetic translocations, not evaluated in our study, could be present in those tumors with very few point mutations, amplifications, or homozygous deletions. Fourth, it is possible that low copy number gains or loss-of-heterozygosity (LOH) of specific regions containing histone-modifying genes could mimic the intragenic mutations that we observed (36). Finally, it is possible that heritable epigenetic alterations are responsible for initiating some MBs. The last explanation, involving covalent changes in chromatin proteins and DNA, is intriguing given the new data on MLL2 in this tumor type. It should thus be informative to characterize the methylation status of histones and DNA in MBs with and without MLL2/MLL3 gene alterations, as well as to determine the expression changes resulting from these gene mutations. These data highlight the important connection between genetic alterations in the cancer genome and epigenetic pathways and provide potentially new avenues for research and disease management in MB patients.

Somatic mutations are mutations that occur or are present in a somatic tissue but not in other somatic tissues or in the germ line. Such mutations can be initially determined by comparison to a reference wild-type or mutant sequence in a database for example. To confirm that the mutation is indeed a somatic mutation, however, one can compare it to a nucleic acid isolated from another somatic tissue or a germ line tissue of the same individual. One somatic tissue which can be used for comparison is a brain tissue that is not apparently neoplastic. Typically tissues that will be tested will be tissues that are suspected of being medulloblastoma or of being medulloblastoma meatastases. Blood or other bodily fluids that may contain shed tumor cells or tumor DNA or tumor protein may also be tested.

A CAN gene mutational signature may comprise one or more of the genes shown in Table 2. For example, the signature may comprise at least 1, 2, 3, 4, 5, 6, or 7 genes. Groups of tumors can be classified or stratified on the basis of these signatures. The classified or stratified tumors may be used, e.g., to make prescribing decisions, to make prognoses, to test new drugs or old drugs.

Mutation detection can be carried out by any techniques known in the art. These include without limitation, sequencing of proteins or nucleic acids, immunological techniques, such as protein blots or immunohistochemistry, hybridization techniques such as on probe arrays, primer extension methods, and amplification methods such as allele-specific amplification. Other methods may be used, and methods may be combined as desirable. The method may involve sequence determination of all or part of a gene, cDNA, or protein. The method may involve mutation-specific reagents such as probes, primers, or antibodies. The method may be based on amplification, hybridization, antibody-antigen reactions, primer extension, etc. Any technique or method known in the art for determining a sequence-based feature may be used.

Genes whose mutations appear to disrupt normal function may be supplemented therapeutically by supplying to a patient with such a mutation the wild-type version of the protein or nucleic acid. These may be supplied by any means known in the art. Typically these will be targeted to the tumor, where the defect is. Vectors for nucleic acids which can be used include viral and non-viral vectors.

Efficacy can be determined by any of the standard means known in the art. Any index of efficacy can be used. The index may be life span, disease free remission period, tumor shrinkage, tumor growth arrest, improvement of quality of life, decreased side effects, decreased pain, etc. Any useful measure of patient health and well-being can be used. In addition, in vitro testing may be done on tumor cells that have particular signatures. Tumor cells with particular signatures can also be tested in animal models.

Once a signature has been correlated with sensitivity or resistance to a particular therapeutic regimen, that signature can be used for prescribing a treatment to a patient. Thus determining a signature is useful for making therapeutic decisions. The signature can also be combined with other physical or biochemical findings regarding the patient to arrive at a therapeutic decision. A signature need not be the sole basis for making a therapeutic decision.

An anti-cancer agent associated with a signature may be, for example, docetaxel, paclitaxel, topotecan, adriamycin, etoposide, fluorouracil (5-FU), or cyclophosphamide. The agent may be an alkylating agent (e.g., nitrogen mustards), antimetabolites (e.g., pyrimidine analogs), radioactive isotopes (e.g., phosphorous and iodine), miscellaneous agents (e.g., substituted ureas) and natural products (e.g., vinca alkyloids and antibiotics). The therapeutic agent may be allopurinol sodium, dolasetron mesylate, pamidronate disodium, etidronate, fluconazole, epoetin alfa, levamisole HCL, amifostine, granisetron HCL, leucovorin calcium, sargramostim, dronabinol, mesna, filgrastim, pilocarpine HCL, octreotide acetate, dexrazoxane, ondansetron HCL, ondansetron, busulfan, carboplatin, cisplatin, thiotepa, melphalan HCL, melphalan, cyclophosphamide, ifosfamide, chlorambucil, mechlorethamine HCL, carmustine, lomustine, polifeprosan 20 with carmustine implant, streptozocin, doxorubicin HCL, bleomycin sulfate, daunirubicin HCL, dactinomycin, daunorucbicin citrate, idarubicin HCL, plimycin, mitomycin, pentostatin, mitoxantrone, valrubicin, cytarabine, fludarabine phosphate, floxuridine, cladribine, methotrexate, mercaptipurine, thioguanine, capecitabine, methyltestosterone, nilutamide, testolactone, bicalutamide, flutamide, anastrozole, toremifene citrate, estramustine phosphate sodium, ethinyl estradiol, estradiol, esterified estrogens, conjugated estrogens, leuprolide acetate, goserelin acetate, medroxyprogesterone acetate, megestrol acetate, levamisole HCL, aldesleukin, irinotecan HCL, dacarbazine, asparaginase, etoposide phosphate, gemcitabine HCL, altretamine, topotecan HCL, hydroxyurea, interferon alpha-2b, mitotane, procarbazine HCL, vinorelbine tartrate, *E. coli* L-asparaginase, *Erwinia* L-asparaginase, vincristine sulfate, denileukin diftitox, aldesleukin, rituximab, interferon alpha-2a, paclitaxel, docetaxel, BCG live (intravesical), vinblastine sulfate, etoposide, tretinoin, teniposide, porfimer sodium, fluorouracil, betamethasone sodium phosphate and betamethasone acetate, letrozole, etoposide citrororum factor, folinic acid, calcium leucouorin, 5-fluorouricil, adriamycin, cytoxan, or diamino-dichloro-platinum.

The signatures of CAN genes according to the present invention can be used to determine an appropriate therapy for an individual. For example, a sample of a tumor (e.g., a tissue obtained by a biopsy procedure) can be provided from the individual, such as before a primary therapy is administered. The gene expression profile of the tumor can be determined, such as by a nucleic acid array (or protein array) technology, and the expression profile can be compared to a database correlating signatures with treatment outcomes. Other information relating to the human (e.g., age, gender, family history, etc.) can factor into a treatment recommendation. A healthcare provider can make a decision to administer or prescribe a particular drug based on the comparison of the CAN gene signature of the tumor and information in the database. Exemplary healthcare providers include doctors, nurses, and nurse practitioners. Diagnostic laboratories can also recommend a therapy based on signatures and other information about the patient.

Following treatment with a primary cancer therapy, the patient can be monitored for an improvement or worsening of the cancer. A tumor tissue sample (such as a biopsy) can be taken at any stage of treatment. In particular, a tumor tissue sample can be taken upon tumor progression, which can be determined by tumor growth or metastasis. A CAN gene signature can be determined, and one or more secondary therapeutic agents can be administered to increase, or restore, the sensitivity of the tumor to the primary therapy. Treatment predictions may be based on pre-treatment CAN gene signatures. Secondary or subsequent therapeutics can be selected based on the subsequent assessments of the patient and the later signatures of the tumor. The patient will typically be monitored for the effect on tumor progression.

A medical intervention can be selected based on the identity of the CAN gene signature. For example, individuals can be sorted into subpopulations according to their genotype. Genotype-specific drug therapies can then be prescribed. Medical interventions include interventions that are widely practiced, as well as less conventional interventions. Thus, medical interventions include, but are not limited to, surgical procedures, administration of particular drugs or dosages of particular drugs (e.g., small molecules, bioengineered proteins, and gene-based drugs such as antisense oligonucleotides, ribozymes, gene replacements, and DNA- or RNA-based vaccines), including FDA-approved drugs, FDA-approved drugs used for off-label purposes, and experimental agents. Other medical interventions include nutritional therapy, holistic regimens, acupuncture, meditation, electrical or magnetic stimulation, osteopathic remedies, chiropractic treatments, naturopathic treatments, and exercise.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

The determination of the human genome sequence and improvements in sequencing and bioinformatic technologies have recently permitted genome-wide analyses of human cancers. To date, the sequences of all protein-encoding genes have been reported in 83 human cancers (9-20), representing a variety of adult tumors. In this study, we provide the first comprehensive sequence analysis of a solid tumor of childhood. Our data point to a major genetic difference between adult and childhood solid tumors and provide new information to guide further research on this disease.

Sequencing Strategy

In the first stage of our analysis, called the Discovery Screen, 457,814 primers (table S1) were used to amplify and sequence 225,752 protein coding exons, adjacent intronic splice donor and acceptor sites, and miRNA genes in 22 pediatric MB samples and one matched normal sample (table S2). These analyses corresponded to 50,191 transcripts representing at least 21,039 protein encoding genes present in the Ensembl, CCDS and RefSeq databases and 715 microRNA genes from the miRBase database. A total of 404,438 primers were described in our previous publications and an additional 53,376 primers were newly designed to amplify technically-challenging genomic regions, miRNAs, or newly discovered Ensembl genes (table S1). The data were assembled for each amplified region and evaluated using stringent quality control criteria, resulting in the successful amplification and sequencing of 96% of targeted amplicons and 95% of targeted bases in the 22 tumors. A total of 735 Mb of tumor sequence data were generated in this manner.

Following automated and manual curation of the sequence traces, regions containing potential sequence alterations (single base mutations and small insertions and deletions) not present in the reference genome or single nucleotide polymorphism (SNP) databases were re-amplified in both the tumor and matched normal tissue DNA and analyzed either through sequencing by synthesis on an Illumina GAIT instrument or by conventional Sanger sequencing (21). This process allowed us to confirm the presence of the mutation in the tumor sample and determine whether the alteration was somatic (i.e. tumor-specific). Additionally, mutations identified in the four xenograft samples were confirmed to be present in the corresponding primary tumors.

EXAMPLE 2

Analysis of Sequence and Copy Number Alterations

A total of 225 somatic mutations were identified in this manner (Table 1 and Table S3). Of these, 199 (88%) were point mutations and the remainder were small insertions, duplications or deletions, ranging from 1 to 48 bp in length. Of the point mutations, 148 (74%) were predicted to result in non-synonymous changes, 42 (21%) were predicted to be synonymous, and 9 (5%) were located at canonical splice site residues that were likely to alter normal splicing. 36 of the 225 (16%) somatic mutations were predicted to prematurely truncate the encoded protein, either through newly generated nonsense mutations or through insertions, duplications or deletions leading to a change in reading frame. The mutation spectrum observed for MB was similar to those seen in pancreatic, colorectal, glial and other malignancies (22), with 5'-CG to 5'-TA transitions observed more commonly than other substitutions (Table 1). Such transitions are generally associated with endogenous processes, such as deamination of 5-methylcytosine residues, rather than exposure to exogenous carcinogens (23).

TABLE 1

Summary of somatic sequence mutations in five tumor types.

|  | Medulloblastoma* | Pancreas* | Glioblastoma† | Colorectal‡ | Breast‡ |
|---|---|---|---|---|---|
| Number of samples analyzed | 22 | 24 | 21 | 11 | 11 |
| Number of mutated genes | 218 | 1007 | 685 | 769 | 1026 |
| Number of non-silent mutations | 183 | 1163 | 748 | 849 | 1112 |
| Missense§ | 130 (71.0) | 974 (83.7) | 622 (83.2) | 722 (85) | 909 (81.7) |
| Nonsense§ | 18 (9.8) | 60 (5.2) | 43 (5.7) | 48 (5.7) | 64 (5.8) |
| Insertion§ | 5 (2.7) | 4 (0.3) | 3 (0.4) | 4 (0.5) | 5 (0.4) |
| Deletion§ | 14 (7.7) | 43 (3.7) | 46 (6.1) | 27 (3.2) | 78 (7.0) |
| Duplication§ | 7 (3.8) | 31 (2.7) | 7 (0.9) | 18 (2.1) | 3 (0.3) |
| Splice site or UTR§ | 9 (4.9) | 51 (4.4) | 27 (3.6) | 30 (3.5) | 53 (4.8) |
| Average number of non-silent mutations per sample | 8 | 48 | 36 | 77 | 101 |
| Total number of substitutions** | 199 | 1486 | 937 | 893 | 1157 |
| Substitutions at C:G base pairs |  |  |  |  |  |
| C:G to T:A†† | 109 (54.8) | 798 (53.8) | 601 (64.1) | 534 (59.8) | 422 (36.5) |
| C:G to G:C†† | 12 (6.0) | 142 (9.6) | 67 (7.2) | 61 (6.8) | 325 (28.1) |
| C:G to A:T†† | 41 (20.6) | 246 (16.6) | 114 (12.1) | 130 (14.6) | 175 (15.1) |
| Substitutions at T:A base pairs |  |  |  |  |  |
| T:A to C:G†† | 19 (9.5) | 142 (9.6) | 87 (9.3) | 69 (7.7) | 102 (8.8) |
| T:A to G:C†† | 14 (7.0) | 79 (5.3) | 24 (2.6) | 59 (6.6) | 57 (4.9) |
| T:A to A:T†† | 4 (2.0) | 77 (5.2) | 44 (4.7) | 40 (4.5) | 76 (6.6) |
| Substitutions at specific dinucleotides |  |  |  |  |  |
| 5'-CpG-3'†† | 85 (42.7) | 563 (37.9) | 404 (43.1) | 427 (47.8) | 195 (16.9) |
| 5'-TpC-3'†† | 14 (7.0) | 218 (14.7) | 102 (10.9) | 99 (11.1) | 395 (34.1) |

*Based on 22 tumors analyzed in the current study
*Based on 24 tumors analyzed in Jones et al, Science, 321: 1801-1806, 2008.
†Based on 21 nonhypermutable tumors analyzed in Parsons et al., Science 321: 1807-1812, 2008.
‡Based on 11 breast and 11 colorectal tumors analyzed in Wood et al., Science 20: 1108-13 2007
§Numbers in parentheses refer to percentage of total non-silent mutations.
**Includes synonymous as well as nonsynonymous point mutations identified in the indicated study.
††Numbers in parentheses refer to percentage of total substitutions The distribution of somatic mutations among the 22 MBs is illustrated in FIG. 1. Two key differences were observed in this cancer as compared to the typical adult solid tumor. First, the average number of non-silent (NS) somatic mutations (non-synonymous missense mutations, indels, or splice site alterations) per MB patient was only 8.3, which is 5 to 10-fold less than the average number of alterations detected in any previously studied solid tumor type (Table 1). Second, the relative proportion of nonsense, insertion, and duplication mutations was about two-fold higher, and the proportion of missense mutations was smaller, in MBs than in any of the adult solid tumors analyzed.

We evaluated copy number alterations using Illumina SNP arrays containing ~1 million probes in a set of 23 MBs, including all Discovery Screen samples. Using stringent criteria for focal amplifications and homozygous deletions, we identified 78 and 125 of these alterations, respectively, in these tumors (tables S4 and S5) (21). High level amplifications indicate an activated oncogene within the affected region, whereas homozygous deletions may signal inactivation of a tumor suppressor gene. The total number of copy number changes affecting coding genes in each tumor is plotted in FIG. 1. Similar to the point mutation data, we found considerably fewer amplifications (an average of 0.4 per tumor) and homozygous deletions (an average of 0.8 per tumor) than observed in adult solid tumors (which average 1.6 amplifications and 1.9 homozygous deletions) (16, 17, 24).

We next evaluated a subset of the mutated genes in an additional 67 primary MBs, including both pediatric and adult tumors (table S2). This "Prevalence Screen" comprised sequence analysis of the coding exons of all genes that were either found to be mutated twice or more in the Discovery Screen or were mutated once in the Discovery Screen and had previously been reported to be mutated in other tumor types. NS somatic mutations were identified in 7 of these 15 genes (table S3). In the Prevalence Screen, the non-silent mutation frequency was calculated to be 9.5 mutations per Mb, far higher than the rate found in the Discovery Screen (0.24 mutations per Mb; P<0.001, binomial test). The ratio of NS to S mutations in the Prevalence Screen was 24 to 1, which is over 4-fold higher than the 4.4 to 1 ratio determined in the Discovery Screen (P<0.01, binomial test). In addition, 23 of the 50 Prevalence Screen mutations (46%) were nonsense alterations or insertions or deletions that were expected to truncate the encoded protein. These data suggest that the genes selected for the Prevalence Screen were enriched for functionally important genes.

EXAMPLE 3

Frequent Mutation of MLL2 and MLL3 in MB

Somatic mutations in tumor DNA can either provide a selective advantage to the tumor cell (driver mutations) or have no net effect on tumor growth (passenger mutations). A variety of methods are available to help distinguish whether a specific gene or individual mutation is likely to be a driver. At the gene level, the "passenger probability" score corresponds to a metric reflecting the frequency of mutations, including point mutations, indels, amplifications, and homozygous deletions, normalized for sequence context as well nucleotide composition and length of the gene. The lower the passenger probability score, the less likely it is that mutations in the specific gene represent passengers. Passenger probability scores of the candidate cancer genes (CAN-genes) identified in MB are listed in Table 2.

TABLE 2

Medulloblastoma CAN-genes*

| Gene | Number of Mutations | Number of Amplifications | Number of Deletions | Passenger Probability |
|---|---|---|---|---|
| PTCH1 | 22/89 | 0/23 | 0/23 | <0.001 |
| MLL2 | 12/89 | 0/23 | 0/23 | <0.001 |
| CTNNB1 | 11/89 | 0/23 | 0/23 | <0.001 |
| TP53 | 6/89 | 0/23 | 0/23 | <0.001 |
| MYC | 0/89 | 3/23 | 0/23 | <0.001 |
| PTEN | 3/89 | 0/23 | 0/23 | 0.008 |
| OTX2 | 0/89 | 2/23 | 0/23 | 0.015 |
| SMARCA4 | 3/89 | 0/23 | 0/23 | 0.10 |
| MLL3 | 3/89 | 0/23 | 0/23 | 0.10 |

*CAN-genes were defined as those having at least two non-silent alterations in the samples analyzed. Passenger probabilities were calculated as described in (21).

At the individual mutation level, the CHASM score is a metric reflecting the likelihood that a missense mutation alters the normal function of the respective protein and provides a selective advantage to the tumor cell (25). The CHASM score is based on 73 biochemical features, including conservation of the wild-type amino acid and the mutation's predicted effects on secondary structure. The CHASM score for each mutation observed in this study and the associated P-value listed in table S3. Nonsense mutations, as well as small insertions or deletions that disrupt the reading frame are likely to disrupt function and are assigned a score of 0.001 in this Table. Approximately 27% of the observed mutations in MB were predicted to disrupt gene function using this approach.

Finally, we evaluated the Discovery Screen mutational data (including both sequence and copy number alterations) at a higher "gene-set" level. There is now abundant evidence that alterations of driver genes can be productively organized according to the biochemical pathways and biological processes through which they act. The number of gene-sets that define these pathways and processes is much less than the number of genes and can provide clarity to lists of genes identified through mutational analyses. In the current study, we used a recently described approach that scores each gene-set at the patient rather than the gene level and is more powerful than conventional gene-oriented approaches (21, 26). The most statistically significant pathways and biologic processes highlighted by this gene-set analysis are depicted in table S6. Of these, two—the Hedgehog and Wnt signaling pathways—have been previously shown to play a critical role in MB development. In the Hedgehog pathway, PTCH1 was mutated in 15 of 89 (17%) tumors, and in the Wnt pathway, CTNNB1 was mutated in 11 of 89 (12%) tumors (table S3).

Figure 2:
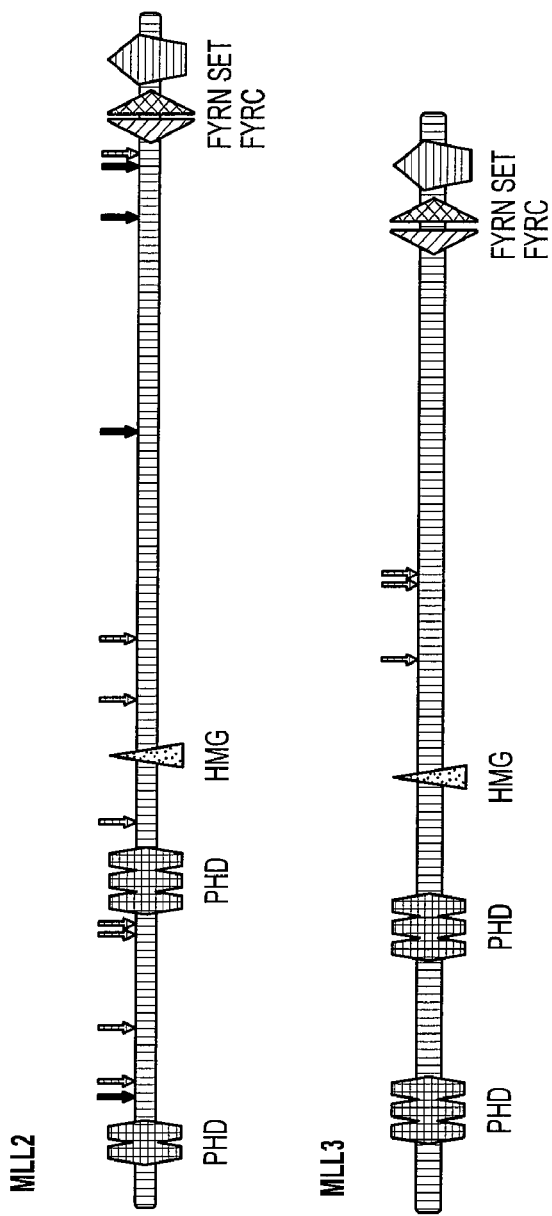
FIG. 2. Somatic mutations in MLL2 and MLL3 genes. Nonsense mutations and out of frame insertions and deletions are indicated as hatched-line arrows, while missense mutations are indicated as black arrows. Domains indicated include PHD, plant homeodomain finger, HMG, high mobility group box, FYRN, FY-rich N-terminal domain, FYRC, FY-rich C-terminal domain, SET, Su(var)3-9 Enhancer-of-zeste Trithorax methyltransferase domain.

Remarkably, however, the pathways most highly enriched for genetic alterations had not previously been implicated in MB. These involved genes responsible for chromatin remodeling and transcriptional regulation, particularly the histone-lysine N-methyltransferase MLL2. Seventeen of the 89 (19%) tumors harbored a mutation in one of three genes within these pathways or in a related gene member: MLL2 (mutated in 12 tumors), MLL3 (3 tumors), SMARCA4 (3 tumors), and ARID1A (1 tumor). The mutations in these genes could be clearly distinguished from passenger alterations. In MLL2, for example, 8 of the 12 mutations (67%) were predicted to truncate the encoded proteins as a result of nonsense mutations, out-of-frame indels, or splice site mutations. In contrast, only 31 of the 223 mutations (14%) not affecting core genes of the Hedgehog, Wnt, or MLL2-related pathways (PTCH1, CTNNB1, MLL2, MLL3, SMARCA4, and ARID1A) resulted in predicted protein truncations (p<0.001, Fisher's exact test). The probability that by chance alone 11 of the 15 mutations in the two histone methyltransferase genes would cause truncations is very small (p<0.001, binomial test). All truncating mutations in MLL2 and MLL3 were predicted to result in protein products lacking the key methyltransferase domain (FIG. 2). These data not only provide strong evidence that these pathways are important to MBs, but they also show that MLL2 and MLL3 are, on the basis of genetic criteria, tumor suppressor genes that are inactivated by mutation.

REFERENCES

The disclosure of each reference cited is expressly incorporated herein.
1. F. Giangaspero et al., in *WHO Classification of the Central Nervous System*, H. O. D. N. Louis, O. D. Wiestler, W. K. Cavenee, Ed. (WHO Press, Lyon, 2007).
2. W. R. Polkinghorn, N. J. Tarbell, *Nat Clin Pract Oncol* 4, 295 (May, 2007).
3. P. A. Northcott et al., *J Clin Oncol*, (September 7).
4. M. C. Thompson et al., *J Clin Oncol* 24, 1924 (Apr. 20, 2006).
5. S. H. Bigner, H. S. Friedman, B. Vogelstein, W. J. Oakes, D. D. Bigner, *Cancer Res* 50, 2347 (Apr. 15, 1990).
6. K. Boon, C. G. Eberhart, G. J. Riggins, *Cancer Res* 65, 703 (Feb. 1, 2005).
7. C. Di et al., *Cancer Res* 65, 919 (Feb. 1, 2005).
8. R. L. Saylors, 3rd et al., *Cancer Res* 51, 4721 (Sep. 1, 1991).
9. L. Ding et al., *Nature* 464, 999 (Apr. 15, 2010).
10. W. Lee et al., *Nature* 465, 473 (May 27, 2010).
11. E. R. Mardis et al., *N Engl J Med* 361, 1058 (Sep. 10, 2009).
12. E. D. Pleasance et al., *Nature* 463, 191 (Jan. 14, 2009).
13. E. D. Pleasance et al., *Nature* 463, 184 (Jan. 14, 2010).
14. S. P. Shah et al., *Nature* 461, 809 (Oct. 8, 2009).
15. T. J. Ley et al., *Nature* 456, 66 (Nov. 6, 2008).
16. S. Jones et al., *Science* 321, 1801 (Sep. 26, 2008).
17. D. W. Parsons et al., *Science* 321, 1807 (Sep. 26, 2008).
18. T. Sjoblom et al., *Science* 314, 268 (Oct. 13, 2006).
19. L. D. Wood et al., *Science* 318, 1108 (Nov. 16, 2007).
20. S. Jones et al., *Science*, (September 8).
21. Materials and methods are available as supporting material on *Science* Online.
22. C. Greenman et al., *Nature* 446, 153 (Mar. 8, 2007).
23. T. Soussi, C. Beroud, *Hum Mutat* 21, 192 (March, 2003).
24. R. J. Leary et al., *Proc Natl Acad Sci USA* 105, 16224 (Oct. 21, 2008).
25. H. Carter et al., *Cancer Res* 69, 6660 (Aug. 15, 2009).
26. K. K. Boca S M, Velculescu V E, Vogelstein B, Parmigiani G, *Submitted*, (2010).
27. P. A. Northcott, J. T. Rutka, M. D. Taylor, *Neurosurg Focus* 28, E6 (January).
28. N. Beerenwinkel et al., *PLoS Comput Biol* 3, e225 (November 2007).
29. C. E. Furneaux et al., *Br J Cancer* 99, 1678 (Nov. 18, 2008).
30. J. Lee et al., *Proc Natl Acad Sci USA* 106, 8513 (May 26, 2009).
31. S. A. Forbes et al., *Nucleic Acids Res* 38, D652 (January 2009).
32. G. van Haaften et al., *Nat Genet* 41, 521 (May, 2009).
33. G. L. Dalgliesh et al., *Nature* 463, 360 (Jan. 21, 2010).
34. R. D. Morin et al., *Nat Genet* 42, 181 (February).
35. K. C. Wiegand et al., *N Engl J Med*, (2010).
36. P. A. Northcott et al., *Nat Genet* 41, 465 (April, 2009).
37. M. Vermeulen, H. T. M. Timmers, *Epigenomics* 2, 395 (June, 2010, 2010).
38. K. I. Ansari, S. S. Mandal, *FEBS J* 277, 1790 (April).
39. K. Agger et al., *Nature* 449, 731 (Oct. 11, 2007).
40. D. C. Adamson et al., *Cancer Res* 70, 181 (January 1).
41. J. Sierra, T. Yoshida, C. A. Joazeiro, K. A. Jones, *Genes Dev* 20, 586 (Mar. 1, 2006).
42. D. A. Lim et al., *Nature* 458, 529 (Mar. 26, 2009).
43. R. J. Gilbertson, D. W. Ellison, *Annu Rev Pathol* 3, 341 (2008).
44. C. G. Eberhart et al., *Cancer* 94, 552 (Jan. 15, 2002).

EXAMPLE 4

Materials and Methods
Medulloblastoma (MB) DNA Samples

Tumor DNA was obtained from MB xenografts, cell lines, and primary tumors, as previously described (1). The Discovery Screen consisted of 22 tumor samples (17 primary tumors, 4 xenografts, and 1 cell line), with the Prevalence Screen including another 67 primary tumors. Clinical data regarding Discovery Screen and Prevalence Screen samples are available in Table S2. All samples had been given a diagnosis of MB (WHO grade IV) by institutional report. All samples with available hematoxylin and eosin-stained (H+E) slides or available tissue blocks from which new H+E slides could be produced were subjected to central review by a pediatric neuropathologist (PB). For each slide the percentage of tumor cells present was estimated, and the MBs were subclassified as large cell/anaplastic (LCA), nodular/desmoplastic (ND), or classic, non-nodular (C) when possible. All tumor samples were obtained at the time of the original surgery except one Discovery Screen sample (MB106X) and 6 Prevalence Screen samples (MB107PT, MB116PT, MB157PT, MB211PT, MB230PT, MB239PT), which were obtained at the time of MB recurrence. One sample (MB122PT) was obtained from a patient with Li-Fraumeni syndrome (germline mutation of TP53).

Overview of Samples Used in the Discovery and Prevalence Screens:

|  | Discovery | Prevalence | Total |
| --- | --- | --- | --- |
| Number of tumor samples | 22 | 67 | 89 |
| Patient age | | | |
| Mean age (years) | 6.7 | 15.7 | 13.6 |
| Median age (years) | 5.5 | 10.5 | 10.1 |
| Patients <18 years old | 19 | 39 | 58 |
| Patients >=18 years old | 0 | 22 | 22 |
| Unknown | 3 | 6 | 9 |
| Patient sex | | | |
| Male | 15 | 40 | 55 |
| Female | 4 | 23 | 27 |
| Unknown | 3 | 4 | 7 |
| Sample source | | | |
| Primary tumor | 17 | 67 | 84 |
| Xenograft | 4 | 0 | 4 |
| Cell line | 1 | 0 | 1 |
| Sample type | | | |
| New diagnosis MB | 18 | 57 | 75 |
| Recurrent MB | 1 | 6 | 7 |
| Unknown | 3 | 4 | 7 |
| Histologic subtype | | | |
| Large cell/anaplastic | 4 | 7 | 11 |
| Nodular/desmoplastic | 1 | 9 | 10 |
| Classic, non-nodular | 13 | 40 | 53 |
| Not determined | 4 | 11 | 15 |

Identification of Transcripts for Sequence Analysis

Protein encoding transcripts were derived from three sources. The majority of protein encoding transcripts (46,482) were derived from the 61,043 transcripts present in the Ensembl database downloaded from the UCSC Genome Bioinformatics site (ensGene.txt, File Date Aug. 27, 2008). The Ensembl transcripts were then compared to 20,025 transcripts present in the CCDS database downloaded from the UCSC Genome Bioinformatics Site (ccdsGene.txt, File Date Feb. 2, 2009). This comparison identified 132 protein encoding transcripts not represented in Ensembl which were added to the list of transcripts to be considered for sequencing. The above 46,614 protein encoding transcripts were then compared to 29,996 transcripts present in the RefSeq database downloaded from the UCSC Genome Bioinformatics Site (refGene.txt, File Date Jan. 18, 2009). This analysis identified a further 4,407 protein encoding transcripts that were unique to RefSeq bringing the total number of transcripts under consideration to 51,021. 446 Ensembl derived transcripts were eliminated because they lacked uninterrupted open reading frames. Finally, 1,099 transcripts that mapped to the mitochondrial genome, chromosome Y or alternate haplotypes were eliminated bringing the total number of protein encoding transcripts targeted for sequencing to 49,476.

The protein encoding transcripts were supplemented with microRNA (miRNA) transcripts. Coordinates for 718 miRNAs were downloaded from the Sanger miRBase Sequence Database (Release 13.0) and 715 were added to the list of transcripts targeted for sequencing after excluding 3 miRNAs mapped to the mitochondrial genome. This addition brought the total number of transcripts targeted for sequencing to 50,191. The combined set of transcripts represented 24,893 genes (24,178 protein encoding and 715 miRNA) and comprised 226,467 unique exons (225,752 protein encoding and 715 miRNA) covering 36,909,796 bases. For the purposes of considering protein encoding genes, transcripts were grouped into genes using their Ensembl gene names. CCDS and RefSeq transcripts not present in Ensembl were assumed to represent distinct genes and were designated with their transcript names. For miRNA, each distinct transcript was assumed to represent a different gene.

Primer Design and Sequence Analysis

A total of 36,909,796 bases were identified within the regions of interest (ROIs) of the 50,191 targeted transcripts. The ROIs comprised the entire transcribed portion of the 715 miRNA exons and the protein encoding portion plus 4 bases of flanking sequence for the 225,752 protein encoding exons. For clarity, the 4 bases of flanking sequence for the protein encoding exons would thus encompass sequences upstream of the start codon, downstream of the stop codon, and splice acceptors and splice donors. A total of 228,907 primer pairs were designed that could amplify 35,190,701 (95.3%) bases of the ROIs (table S1). These primer pairs were then used to amplify and sequence DNA from the 22 medulloblastoma samples and one normal sample as previously described (2,3). The vast majority of these primers (219,532; 95.9%) yielded PCR products and high quality sequencing results in 18 or more of the 23 samples sequenced. A total of 735,126,675 bases were evaluated for mutations in the 22 medulloblastomas (average of 31,962,029 bases per sample, range 28,031,708 to 32,395,730) (sequence data are available at the cgap.nci.nih.gov website). Of the evaluated bases, 99.3% had a Phred score of 20 or more and 97.9% had a score of 30 or more. All coordinates listed in the Supplementary Tables correspond to the human reference genome hg18 release (NCBI 36.1, March 2006).

The sequencing data were analyzed using Mutation Surveyor (SoftGenetics, State College, Pa.) coupled to a relational database (Microsoft SQL Server). Following automated and manual curation of the sequence traces, regions containing potential single base mutations and small insertions and deletions (indels) not present in the reference genome or single nucleotide polymorphism (SNP) databases (dbSNP release 125 variants that had been validated by the HapMap project) were re-amplified in both the tumor and matched normal tissue DNA and analyzed either through sequencing by synthesis on an Illumina GAII instrument or by conventional Sanger sequencing. This process allowed us to confirm the presence of the mutation in the tumor sample and determine whether the alteration was somatic (i.e., tumor-specific). BLAT and In Silico PCR (available at the genome.ucsc.edu website) were used to perform homology searches in the human and mouse genomes and to remove variants present in related genomic regions. Additionally, mutations identified in the xenografts were confirmed to be present in the corresponding primary tumors at this stage of the analysis.

We further evaluated a set of 15 mutated genes that were mutated twice or more in the Discovery Screen samples (either by two sequence alterations or a sequence and copy number alteration) or were mutated once in the Discovery Screen and had previously been reported to be mutated in other tumor types in a second (Prevalence) screen, which included an additional 67 MBs (table S2). The primers used (table S1) and methods of analysis and curation of potential mutations were the same as described for the Discovery Screen.

Copy Number Alterations

The Illumina Infinium™ II Whole Genome Genotyping Assay employing the BeadChip platform was used to analyze tumor samples at 1,199,187 (1M-Duo) SNP loci. All SNP positions were based on the hg18 (NCBI Build 36, March 2006) version of the human genome reference sequence. The genotyping assay begins with hybridization to a 50 nucleotide oligo, followed by a two-color fluorescent single base extension. Fluorescence intensity image files were processed using Illumina BeadStation software to provide normalized intensity values (R) for each SNP position. For each SNP, the normalized experimental intensity value (R) was compared to the intensity values for that SNP from a training set of normal samples and represented as a ratio (called the "Log R Ratio") of log 2(Rexperimental/Rtraining set).

The SNP array data were analyzed using modifications of a previously described method (4). Homozygous deletions (HDs) were defined as two or more consecutive SNPs with a Log R Ratio value of $\leq -2$. The first and last SNPs of the HD region were considered to be the boundaries of the alteration for subsequent analyses. To eliminate chip artifacts and potential copy number polymorphisms, we removed all HDs that were observed with identical boundaries in two or more samples. Adjacent homozygous deletions separated by two or fewer SNPs were considered to be part of the same deletion. To identify the target genes affected by HDs, we compared the location of coding exons in the RefSeq, CCDS and Ensembl databases with the genomic coordinates of the observed HDs. Any gene with a portion of its coding region contained within a homozygous deletion was considered to be affected by the deletion.

As outlined in (4), amplifications were defined by regions with an average Log R ratio≥0.9, containing at least one SNP with a Log R ratio≥1.4 and at least one SNP with a Log R ratio≥1 every ten SNPs. As focal amplifications are more likely to be useful in identifying specific target genes, a second set of criteria were used to remove complex amplifications, large chromosomal regions or entire chromosomes that showed copy number gains. Amplifications >3 Mb in size and groups of nearby amplifications (within 1 Mb) that were also >3 Mb in size were removed. Amplifications or groups of amplifications that occurred at a frequency of ≥4 distinct amplifications in a 10 Mb region or ≥5 amplifications per chromosome were removed. The amplifications remaining after these filtering steps were considered to be focal amplifications and were the only ones included in subsequent statistical analyses. To identify protein coding genes affected by amplifications, we compared the location of the start and stop positions of each gene within the RefSeq, CCDS and Ensmbl databases with the genomic coordinates of the observed amplifications. As amplifications containing only a fraction of a gene are less likely to have a functional consequence, we only considered genes whose entire coding regions were included in the observed amplifications.

Statistical Analysis

Overview of Statistical Analysis

The statistical analyses focused on quantifying the evidence that the mutations in a gene or a biologically defined set of genes reflect an underlying mutation rate that is higher than the passenger rate. In both cases, the analysis integrates data on point mutations with data on copy number alterations (CNA). The methodology for the analysis of point mutations is based on that described in (3) while the methodology for integration across point mutations and CNA's is based on (2). This methodology was used before in both (2) and (3). We provide a self-contained summary herein, as some modifications to the previously described methods were required.

Statistical Analyses of CAN-Genes

The mutation profile of a gene refers to the number of each of the twenty-five context-specific types of mutations defined earlier (5). The evidence on mutation profiles is evaluated using an Empirical Bayes analysis (6) comparing the experimental results to a reference distribution representing a genome composed only of passenger genes. This is obtained by simulating mutations at the passenger rate in a way that precisely replicates the experimental plan. Specifically, we consider each gene in turn and simulate the number of mutations of each type from a binomial distribution with success probability equal to the context-specific passenger rate. The number of available nucleotides in each context is the number of successfully sequenced nucleotides for that particular context and gene in the samples studied. When considering non-synonymous mutations other than indels, we focus on nucleotides at risk, as defined previously (5).

Using these simulated datasets, we evaluated the passenger probabilities for each of the genes that were analyzed in this study. These passenger probabilities represent statements about specific genes rather than about groups of genes. Each passenger probability is obtained via a logic related to that of likelihood ratios: the likelihood of observing a particular score in a gene if that gene is a passenger is compared to the likelihood of observing it in the real data. The gene-specific score used in our analysis is based on the Likelihood Ratio Test (LRT) for the null hypothesis that, for the gene under consideration, the mutation rate is the same as the passenger mutation rate. To obtain a score, we simply transform the LRT to s=log(LRT). Higher scores indicate evidence of mutation rates above the passenger rates. This general approach for evaluating passenger probabilities follows that described by Efron and Tibshirani (6). Specifically, for any given score s, F(s) represents the proportion of simulated genes with scores higher than s in the experimental data, F0 is the corresponding proportion in the simulated data, and p0 is the estimated overall proportion of passenger genes (discussed below). The variation across simulations is small but nonetheless we generated and collated 250 datasets to estimate F0. We then numerically estimated the density functions f and $f_0$ corresponding to F and F0 and calculated, for each score s, the ratio $p_0 \cdot f_0(s)/f(s)$, also known as "local false discovery rate" (6). Density estimation was performed using the function "density" in the R statistical programming language with default settings. The passenger probability calculations depend on an estimate of $p_0$, the proportion of true passengers. Our implementation seeks to give an upper bound to $p_0$ and thus provide conservatively high estimates of the passenger probability. To this end we set $p_0=1$. We also constrained the passenger probability to change monotonically with the score by starting with the lowest values and recursively setting values that decrease in the next value to their right. We similarly constrain passenger probabilities to change monotonically with the passenger rate.

An open source package for performing these calculations in the R statistical environment, named CancerMutationAnalysis, is available at the astor.som.jhmi.edu website. A detailed mathematical account of our specific implementation is provided in (7) and general analytic issues are discussed in (8). The only difference in the present study is that a gene passed into the Prevalence Screen if it had at least two non-silent alterations in at least two tumor samples in the Discovery Screen or at least one nonsynonymous mutation in the Discovery Screen and had also been previously altered in other tumor types. Under the null hypothesis, the assumptions were that a gene passed into the Prevalence Screen if it had at least two nonsynonymous mutations in the Discovery Screen or it had at least one nonsynonymous mutation in the Discovery Screen and it was on a fixed list of known candidate cancer genes.

Statistical Analysis of CNA

For each of the genes involved in amplifications or deletions, we further quantified the strength of the evidence that they drive tumorigenesis through estimations of their passenger probabilities. In each case, we obtain the passenger probability as an a posteriori probability that integrates information from the somatic mutation analysis above with the data presented in this article. The passenger probabilities derived from the point mutation analysis serve as a priori probabilities. Then, a likelihood ratio for "driver" versus "passenger" was evaluated using as evidence the number of samples in which a gene was found to be amplified (or deleted). The passenger term is the probability that the gene in question is amplified (or deleted) at the frequency observed. For each sample, we begin by computing the probability that the observed amplifications (and deletions)

will include the gene in question by chance. Inclusion of all available SNPs is required for amplification, while any overlap of SNPs is sufficient for deletions. Specifically, if in a specific sample N SNPs are typed, and K amplifications are found, whose sizes, in terms of SNPs involved, are $A_1 \ldots A_K$, a gene with G SNPs will be included at random with probability $(A_1-G+1)/N+ \ldots +(A_K-G+1)/N$ for amplifications and
$(A_1+G-1)/N+ \ldots +(A_K+G-1)/N$ for deletions.

We then compute the probability of the observed number of amplifications (or deletions) assuming that the samples are independent but not identically distributed Bernoulli random variables, using the Thomas and Taub algorithm (9). Our approach to evaluating the likelihood under the null hypothesis is highly conservative, as it assumes that all the deletions and amplifications observed only include passengers. The driver term of the likelihood ratio was approximated as for the passenger term, after multiplying the sample-specific passenger rates above by a gene-specific factor reflecting the increase (alternative hypothesis) of interest. This increase is estimated by the ratio between the empirical deletion rate of the gene and the expected deletion rate for that gene under the null. Genes that occurred in the same amplification or deletion as known cancer genes were excluded from this analysis.

This combination approach makes an approximating assumption of independence of amplifications and deletions. In reality, amplified genes cannot be deleted, so independence is technically violated. However, because of the relatively small number of amplification and deletion events, this assumption is tenable for the purposes of our analysis. Inspection of the likelihood, in a logarithmic scale, suggests that it is roughly linear in the overall number of events, supporting the validity of this approximation as a scoring system.

Analysis of Mutated Gene Pathways and Groups

Four types of data were obtained from the MetaCore database (GeneGo, Inc., St. Joseph, Mich.): pathway maps, Gene Ontology (GO) processes, GeneGo process networks, and protein-protein interactions. The memberships of each of the analyzed transcripts in these categories were retrieved from the databases using RefSeq identifiers. In GeneGo pathway maps, 22,622 relations were identified, involving 4,175 transcripts and 509 pathways. For Gene Ontology processes, a total of 66,397 pairwise relations were identified, involving 12,373 transcripts and 4,426 GO groups. For GeneGo process networks, a total of 23,356 pairwise relationships, involving 6,158 transcripts and 127 processes, were identified. The predicted protein products of each mutated gene were also evaluated with respect to their physical interactions with proteins encoded by other mutated genes as inferred from the MetaCore database.

For each of the gene sets considered, we quantified the strength of the evidence that they were altered in a higher-than-average proportion of samples from the Discovery Screen, calculating p-values using a patient-oriented gene-set analysis (the permutation null without heterogeneity method from (10)). We then corrected for multiplicity by the q-value method with an alpha of 0.2 (11). An open source R package for the implementation of this method, PatientGeneSets, is currently in the Development Version of Bioconductor and is available at the bioconductor.org website.

Bioinformatics Analysis

CHASM uses a supervised machine learning method called Random Forest (12,13) to distinguish putative driver mutations on the basis of their similarity to a positive class of driver missense mutations versus a negative class of passenger missense mutations. The Random Forest is an ensemble of CART decision trees (14), each of which is trained on a different subset of training examples and features. The training set used here is larger than the set used in (15). The positive class consists of all missense mutations in the COSMIC database (16) that occur in genes meeting criteria to be considered as tumor suppressors or oncogenes (3299). Tumor suppressor genes are required to harbor at least 6 mutations and to have a ratio of truncating (nonsense, splice site, frameshift) to other non-silent mutations >0.2. Oncogenes are required to have at least one amino acid position that is mutated in at least two tumors.

We generated 5000 random passenger missense mutations for training and another 5000 for feature selection, according to base substitution rates estimated from the medulloblastoma sequencing data, in eight di-nucleotide contexts (Supp CHASM Table 1).

Base Substitution Rates in 8 Di-Nucleotide Contexts in Medulloblastoma.

|   | C in CpG | G in CpG | C in TpC | G in GpA | A | C | G | T |
|---|---|---|---|---|---|---|---|---|
| A | 0.07 | 1.73 | 0.09 | 0.12 | — | 0.06 | 0.10 | 0.03 |
| C | — | 0.04 | — | 0.06 | 0.03 | — | 0.04 | 0.04 |
| G | 0.04 | — | 0.08 | — | 0.05 | 0.04 | — | 0.03 |
| T | 1.49 | 0.09 | 0.11 | 0.13 | 0.03 | 0.08 | 0.08 | — |

We selected 73 predictive features for each missense mutation, which passed a minimum threshold of 0.001 bits of mutual information with class labels. These features included general and position-specific properties of amino acid substitution, predicted protein local structure, evolutionary conservation and curated annotations from the UniProt Knowledgebase (15,17) According to the Random Forest feature importance criterion (13), the most discriminatory features are:

Location in an enzymatic domain involved in post-translational modification;

Compatibility with observed amino acid residues in an alignment of protein orthologs;

Frequency of SNPs in the exon in which the mutation occurs;

Average PhastCons (18) nucleotide-level conservation in the exon in which the mutation occurs;

Change in amino acid polarity resulting from the substitution;

Negative entropy in the column of amino acids that align to the mutated position in a protein superfamily multiple sequence alignment.

The CHASM score for a mutation is the fraction of decision trees in the Random Forest that vote for the passenger class. The score ranges from 0 (unanimous vote for driver) to 1 (unanimous for passenger). We compute P-values and Benjamini-Hochberg false discovery rate (11) using an empirical null score distribution (of ~5000 random mutations generated in a set of genes unlikely to be involved in cancer, based on the Atlas of Genetics and Cytogenetics in Oncology and Haematology (available at atlasgeneticsoncology.org), COSMIC, and the MSigDB C4 gene set collection (19).

The density distribution of mutation scores $f_G$ can be written as a mixture of two score density distributions: $f_D(s)$ for driver scores and $f_P(s)$ for passenger scores (Figure below), with mixing parameter λ, which is the proportion of drivers (Eq 1).

$$f_G = \lambda f_D(s) + (1-\lambda)f_P(s) \qquad \text{Eq 1}$$

We used kernel density estimation (20) to obtain $f_G(.)$. To estimate $f_D(.)$ and $f_P(.)$, we used a trained Random Forest to compute scores for a held-out partition of training set driver and passenger mutations. The proportion of drivers λ was estimated by finding λ*, the value that minimizes the distance between the observed $f_G$ and the mixture of observed $f_D$ and $f_P$ in the interval (0, 0.5) of $f_G(.)$ that we know with more confidence consists of mostly drivers (Eq 2) (15).

$$\lambda^* = \underset{\lambda}{\operatorname{argmin}} \langle f_G, \lambda f_D + (1-\lambda)f_P \rangle_{(0,0.5)} \qquad \text{Eq 2}$$

where the distance metric between two densities $\langle f_1, f_2 \rangle$ is defined as the total squared difference between the two densities, so that $$\lambda^* = \underset{\lambda}{\operatorname{argmin}} \int_0^{0.5} ((\lambda f_D(u) + (1-\lambda)f_P(u) - f_G(u))^2 du \qquad \text{Eq 3}$$

We numerically solved for λ*, using R statistical software.

Figure 3:
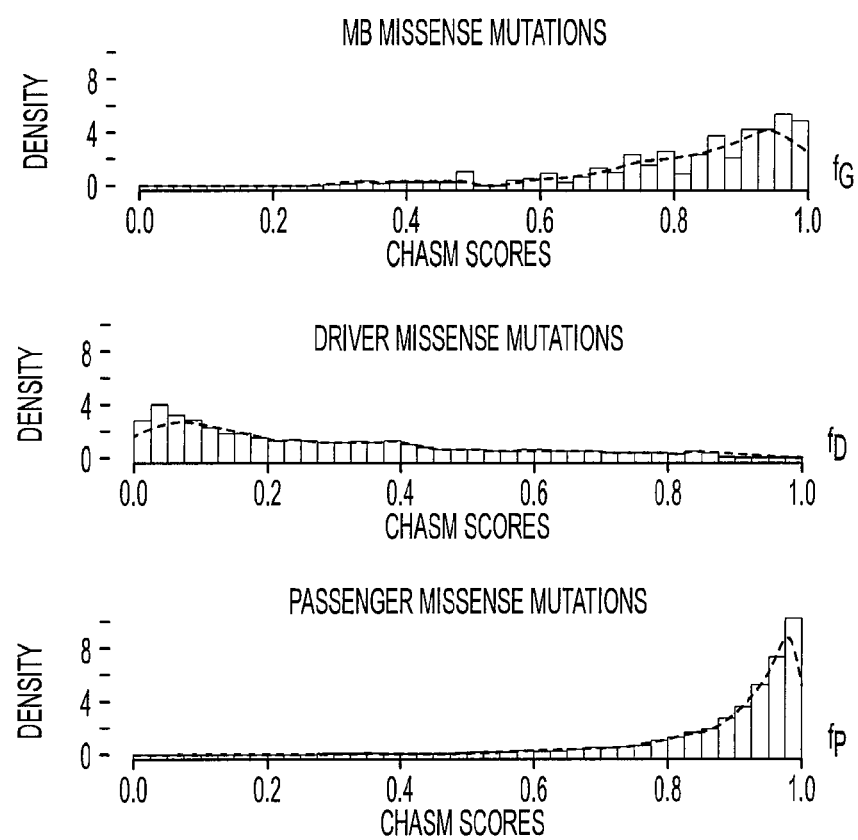
FIG. 3 shows the results of a bioinformatics analysis. CHASM uses a supervised machine learning method called Random Forest (12,13) to distinguish putative driver mutations on the basis of their similarity to a positive class of driver missense mutations versus a negative class of passenger missense mutations.

This method does not consider whether the gene in which a mutation occurs is expressed, but rather predicts whether the mutation would behave as a driver if the gene were expressed. See FIG. 3.

The MB missense mutations modeled as a mixture of drivers and passengers. The densities $f_G$, $f_D$ and $f_P$ (red curves) were calculated by histogram analysis and kernel density estimation of the CHASM scores for the MB somatic missense mutations, and held-out partitions of training set driver missense mutations and training set passenger missense mutations. The driver fraction was estimated by optimizing the value of the mixing parameter λ (Eqs 2 and 3).

We applied CHASM to the 141 unique somatic missense mutations detected in this study to assess their role in medulloblastoma. Fourteen of the mutations scored as putative drivers (FDR<0.20), one of which occurred in TP53 and was previously known to act as a driver. Three of the mutations occurred in PTCH1, a gene in the sonic hedgehog signaling pathway that has previously been implicated in medulloblastoma.

SUPPLEMENTAL REFERENCES FOR EXAMPLE 4

1. T. Sjoblom et al., *Science* 314, 268 (2006).
2. S. Jones et al., *Science* 321, 5897 (2008).
3. D. W. Parsons et al., *Science* 321, 5897 (2008).
4. R. J. Leary et al., *Proc Natl Acad sci USA*. 105, 16224 (2008).
5. L. D. Wood et al., *Science* 318, 1108 (2007).
6. B. Efron, R. Tibshirani, *Genet Epidemiol* 23, 70 (2002).
7. G. Parmigiani et al., "Statistical Methods for the Analysis of Cancer Genome Sequencing Data" (Johns Hopkins University, 2006).
8. G. Parmigiani et al., *Genomics* 93, 17 (2009).
9. M. A. Thomas, A. E. Taub, *Journal of Statistical Computation and Simulation* 14, 125 (1982).
10. S. M. Boca et al., *Submitted* (2010).
11. Y. Benjamini, Y. Hochberg, *Journal of the Royal Statistical Society. Series B (Methodological)* 57 289 (1995).
12. Y. Amit, D. Geman, *Neural Computation* 9, 1545 (1997).
13. L. Breiman, *Machine Learning* 45, 5 (2001).
14. L. Breiman, "Classification and regression trees: Regression Trees, The Wadsworth Statistics/Probability Series" (Wadsworth International Group, 1984).
15. H. Carter et al., *Cancer Res* 69, 6660 (2009).
16. S. Forbes et al., *Br J Cancer* 94, 318 (2006).
17. C. H. Wu et al., *Nucleic Acids Res* 34, D1897 (2006).
18. A. Siepel et al., *Genome Res* 15, 1034 (2005).
19. A. Subramanian et al., *Proc Natl Acad Sci USA* 102, 15545 (2005).
20. E. Parzen, *Ann Math Stat* 33, 1065 (1962).

The invention claimed is:

1. A method of testing a medulloblastoma tumor, comprising:
   testing a gene or its encoded mRNA, cDNA, or protein in a sample of the medulloblastoma tumor and detecting in the gene or its encoded mRNA, cDNA, or protein in the sample of the medulloblastoma tumor a somatic mutation in genes MLL2 or MLL3.

2. The method of claim 1 further comprising testing a matched non-tumor sample for the mutation.

3. The method of claim 1 wherein the gene is tested.

4. The method of claim 1 wherein the cDNA is tested.

5. The method of claim 1 wherein the protein is tested.

6. The method of claim 1 wherein a mutation in gene MLL2 is detected.

7. The method of claim 1 wherein a mutation in gene MLL3 is detected.

8. The method of claim 1 wherein the step of testing comprises sequence determination of all or part of a gene or cDNA.

9. The method of claim 1 wherein the step of testing employs a mutation-specific probe or a mutation-specific primer.

10. The method of claim 1 wherein the step of testing comprises amplification of nucleic acids.

11. The method of claim 1 wherein the step of testing employs a primer extension reaction.

12. The method of claim 1 wherein the step of testing employs nucleic acid hybridization.

13. The method of claim 1 wherein the mutation is a nonsense, out-of-frame insertion, out-of-frame deletion, or splice site mutation.

14. The method of claim 1 wherein the medulloblastoma is a large cell/anaplastic medulloblastoma tumor.

15. The method of claim 1 wherein the mutation is selected from the group consisting of: c14761C>T, c14555G>A, c6941delC, c10972C>T, c7851delC, c1876_1877insG, c1652C>T, c3880_3883delGaCT, c13802G>A, c2655dupC, and c4024C>T.

16. The method of claim 1 wherein the mutation is selected from the group consisting of: P551L, G4601E, Q1342X, R4921X, R4852Q, and R3658C.

17. The method of claim 15 which employs a mutation-specific probe or primer.

* * * * *

UNITED STATES PATENT AND TRADEMARK OFFICE
CERTIFICATE OF CORRECTION

PATENT NO. : 9,695,479 B2
APPLICATION NO. : 13/884154
DATED : July 4, 2017
INVENTOR(S) : Bert Vogelstein et al.

Page 1 of 1

It is certified that error appears in the above-identified patent and that said Letters Patent is hereby corrected as shown below:

In the Specification

On Column 1, first paragraph (government support statement) please replace with the following:
STATEMENT OF GOVERNMENTAL INTEREST
This invention was made with government support under grant number CA057345, CA121113, awarded by the National Institutes of Health. The government has certain rights in the invention.

Signed and Sealed this
Twenty-eighth Day of May, 2019

Andrei Iancu
*Director of the United States Patent and Trademark Office*

SEQUENCE LISTING

<160> NUMBER OF SEQ ID NOS: 135

<210> SEQ ID NO 1
<211> LENGTH: 21
<212> TYPE: DNA
<213> ORGANISM: Homo sapiens

<400> SEQUENCE: 1
ctcagaagtt caccctttgc c                                            21

<210> SEQ ID NO 2
<211> LENGTH: 21
<212> TYPE: DNA
<213> ORGANISM: Homo sapiens

<400> SEQUENCE: 2
gaaggacaaa cacgggaaga g                                            21

<210> SEQ ID NO 3
<211> LENGTH: 20
<212> TYPE: DNA
<213> ORGANISM: Homo sapiens

```
<400> SEQUENCE: 3
ggtgacttgg aggaagggag                                                20

<210> SEQ ID NO 4
<211> LENGTH: 21
<212> TYPE: DNA
<213> ORGANISM: Homo sapiens

<400> SEQUENCE: 4
ctccatccct gtctccttca c                                              21

<210> SEQ ID NO 5
<211> LENGTH: 20
<212> TYPE: DNA
<213> ORGANISM: Homo sapiens

<400> SEQUENCE: 5
gaagggtgtt cctgggattg                                                20

<210> SEQ ID NO 6
<211> LENGTH: 18
<212> TYPE: DNA
<213> ORGANISM: Homo sapiens

<400> SEQUENCE: 6
gacgcccaag gaaagagg                                                  18

<210> SEQ ID NO 7
<211> LENGTH: 18
<212> TYPE: DNA
<213> ORGANISM: Homo sapiens

<400> SEQUENCE: 7
agggaagatg aagccggg                                                  18

<210> SEQ ID NO 8
<211> LENGTH: 18
<212> TYPE: DNA
<213> ORGANISM: Homo sapiens

<400> SEQUENCE: 8
gatttccgcg aggaggag                                                  18

<210> SEQ ID NO 9
<211> LENGTH: 24
<212> TYPE: DNA
<213> ORGANISM: Homo sapiens

<400> SEQUENCE: 9
cagaaatgtt gcaatttcct tctc                                           24

<210> SEQ ID NO 10
<211> LENGTH: 22
<212> TYPE: DNA
<213> ORGANISM: Homo sapiens

<400> SEQUENCE: 10
aatcaacgtg aattgggcta ac                                             22

<210> SEQ ID NO 11
<211> LENGTH: 21
<212> TYPE: DNA
```

```
<213> ORGANISM: Homo sapiens

<400> SEQUENCE: 11
aaagctccaa acggattaag g                                              21

<210> SEQ ID NO 12
<211> LENGTH: 21
<212> TYPE: DNA
<213> ORGANISM: Homo sapiens

<400> SEQUENCE: 12
aagctgctga agcacagagt g                                              21

<210> SEQ ID NO 13
<211> LENGTH: 22
<212> TYPE: DNA
<213> ORGANISM: Homo sapiens

<400> SEQUENCE: 13
tctatttcat ttctggcttg gc                                             22

<210> SEQ ID NO 14
<211> LENGTH: 19
<212> TYPE: DNA
<213> ORGANISM: Homo sapiens

<400> SEQUENCE: 14
atttggccca cagccatac                                                 19

<210> SEQ ID NO 15
<211> LENGTH: 21
<212> TYPE: DNA
<213> ORGANISM: Homo sapiens

<400> SEQUENCE: 15
cattcaagac ctcaagggtc a                                              21

<210> SEQ ID NO 16
<211> LENGTH: 21
<212> TYPE: DNA
<213> ORGANISM: Homo sapiens

<400> SEQUENCE: 16
agaaggctgg agtgagacag g                                              21

<210> SEQ ID NO 17
<211> LENGTH: 22
<212> TYPE: DNA
<213> ORGANISM: Homo sapiens

<400> SEQUENCE: 17
aagtggaccc atccaatgta tc                                             22

<210> SEQ ID NO 18
<211> LENGTH: 21
<212> TYPE: DNA
<213> ORGANISM: Homo sapiens

<400> SEQUENCE: 18
ggcacatccc aactacacat c                                              21

<210> SEQ ID NO 19
<211> LENGTH: 21
```

```
<212> TYPE: DNA
<213> ORGANISM: Homo sapiens

<400> SEQUENCE: 19
tgtcccagga atgtcatcaa c                                              21

<210> SEQ ID NO 20
<211> LENGTH: 21
<212> TYPE: DNA
<213> ORGANISM: Homo sapiens

<400> SEQUENCE: 20
tgattctgac acaggtggtt g                                              21

<210> SEQ ID NO 21
<211> LENGTH: 20
<212> TYPE: DNA
<213> ORGANISM: Homo sapiens

<400> SEQUENCE: 21
ggatggccct agtcttcgtg                                                20

<210> SEQ ID NO 22
<211> LENGTH: 21
<212> TYPE: DNA
<213> ORGANISM: Homo sapiens

<400> SEQUENCE: 22
cagacacaga gcttcccact g                                              21

<210> SEQ ID NO 23
<211> LENGTH: 22
<212> TYPE: DNA
<213> ORGANISM: Homo sapiens

<400> SEQUENCE: 23
tttgggacca gatggattgt ag                                             22

<210> SEQ ID NO 24
<211> LENGTH: 21
<212> TYPE: DNA
<213> ORGANISM: Homo sapiens

<400> SEQUENCE: 24
tgcagttctt accaacctcc c                                              21

<210> SEQ ID NO 25
<211> LENGTH: 20
<212> TYPE: DNA
<213> ORGANISM: Homo sapiens

<400> SEQUENCE: 25
tccagggaag agtgcaacag                                                20

<210> SEQ ID NO 26
<211> LENGTH: 22
<212> TYPE: DNA
<213> ORGANISM: Homo sapiens

<400> SEQUENCE: 26
cgaggacagt ctggtctttg tc                                             22

<210> SEQ ID NO 27
```

```
<211> LENGTH: 21
<212> TYPE: DNA
<213> ORGANISM: Homo sapiens

<400> SEQUENCE: 27
gggagtttga aggcttctcc t                                            21

<210> SEQ ID NO 28
<211> LENGTH: 21
<212> TYPE: DNA
<213> ORGANISM: Homo sapiens

<400> SEQUENCE: 28
gccttcaaac tcccatagag c                                            21

<210> SEQ ID NO 29
<211> LENGTH: 23
<212> TYPE: DNA
<213> ORGANISM: Homo sapiens

<400> SEQUENCE: 29
tgaaatcttc atttgagagg agg                                          23

<210> SEQ ID NO 30
<211> LENGTH: 22
<212> TYPE: DNA
<213> ORGANISM: Homo sapiens

<400> SEQUENCE: 30
agcagaggga agtacagaca gg                                           22

<210> SEQ ID NO 31
<211> LENGTH: 21
<212> TYPE: DNA
<213> ORGANISM: Homo sapiens

<400> SEQUENCE: 31
tcacaccggt tatctgacca c                                            21

<210> SEQ ID NO 32
<211> LENGTH: 24
<212> TYPE: DNA
<213> ORGANISM: Homo sapiens

<400> SEQUENCE: 32
gtgacttgta caatgctgtt tcaa                                         24

<210> SEQ ID NO 33
<211> LENGTH: 19
<212> TYPE: DNA
<213> ORGANISM: Homo sapiens

<400> SEQUENCE: 33
gtcctcagtg cctggaacc                                               19

<210> SEQ ID NO 34
<211> LENGTH: 21
<212> TYPE: DNA
<213> ORGANISM: Homo sapiens

<400> SEQUENCE: 34
gcatgcctac atttgaagca g                                            21
```

```
<210> SEQ ID NO 35
<211> LENGTH: 26
<212> TYPE: DNA
<213> ORGANISM: Homo sapiens

<400> SEQUENCE: 35
ccaaagaatt tattcattca tgtgac                                          26

<210> SEQ ID NO 36
<211> LENGTH: 21
<212> TYPE: DNA
<213> ORGANISM: Homo sapiens

<400> SEQUENCE: 36
ctgccactac cttgctgaat g                                               21

<210> SEQ ID NO 37
<211> LENGTH: 21
<212> TYPE: DNA
<213> ORGANISM: Homo sapiens

<400> SEQUENCE: 37
ctctgcaaat gcgagtgaat g                                               21

<210> SEQ ID NO 38
<211> LENGTH: 25
<212> TYPE: DNA
<213> ORGANISM: Homo sapiens

<400> SEQUENCE: 38
cattattcct gttcttttct ccttg                                           25

<210> SEQ ID NO 39
<211> LENGTH: 21
<212> TYPE: DNA
<213> ORGANISM: Homo sapiens

<400> SEQUENCE: 39
tggattgctt gtcaaattca a                                               21

<210> SEQ ID NO 40
<211> LENGTH: 23
<212> TYPE: DNA
<213> ORGANISM: Homo sapiens

<400> SEQUENCE: 40
caatgtgagc taatggatgt gtt                                             23

<210> SEQ ID NO 41
<211> LENGTH: 21
<212> TYPE: DNA
<213> ORGANISM: Homo sapiens

<400> SEQUENCE: 41
tgctttatgg tgcaatttgg t                                               21

<210> SEQ ID NO 42
<211> LENGTH: 21
<212> TYPE: DNA
<213> ORGANISM: Homo sapiens

<400> SEQUENCE: 42
aaatcgcagc atctagtggt c                                               21
```

```
<210> SEQ ID NO 43
<211> LENGTH: 20
<212> TYPE: DNA
<213> ORGANISM: Homo sapiens

<400> SEQUENCE: 43
ttccgttcct gcttctgtgt                                                   20

<210> SEQ ID NO 44
<211> LENGTH: 21
<212> TYPE: DNA
<213> ORGANISM: Homo sapiens

<400> SEQUENCE: 44
tgcatcgaac tacctcctac g                                                 21

<210> SEQ ID NO 45
<211> LENGTH: 21
<212> TYPE: DNA
<213> ORGANISM: Homo sapiens

<400> SEQUENCE: 45
ggcatagtcc tagcttctgg g                                                 21

<210> SEQ ID NO 46
<211> LENGTH: 24
<212> TYPE: DNA
<213> ORGANISM: Homo sapiens

<400> SEQUENCE: 46
ggaggttgga gagtggatag tttc                                              24

<210> SEQ ID NO 47
<211> LENGTH: 24
<212> TYPE: DNA
<213> ORGANISM: Homo sapiens

<400> SEQUENCE: 47
aaggaaacta tccactctcc aacc                                              24

<210> SEQ ID NO 48
<211> LENGTH: 21
<212> TYPE: DNA
<213> ORGANISM: Homo sapiens

<400> SEQUENCE: 48
tcctctgagg ctttccctta g                                                 21

<210> SEQ ID NO 49
<211> LENGTH: 21
<212> TYPE: DNA
<213> ORGANISM: Homo sapiens

<400> SEQUENCE: 49
gcactggcat tgcatagaaa g                                                 21

<210> SEQ ID NO 50
<211> LENGTH: 21
<212> TYPE: DNA
<213> ORGANISM: Homo sapiens

<400> SEQUENCE: 50
tgtgatccgt gtatttgcct g                                                 21
```

<210> SEQ ID NO 51
<211> LENGTH: 21
<212> TYPE: DNA
<213> ORGANISM: Homo sapiens

<400> SEQUENCE: 51
ggcttgggta ctttcacctt g                                              21

<210> SEQ ID NO 52
<211> LENGTH: 21
<212> TYPE: DNA
<213> ORGANISM: Homo sapiens

<400> SEQUENCE: 52
agtccctcac atgggtcttt g                                              21

<210> SEQ ID NO 53
<211> LENGTH: 21
<212> TYPE: DNA
<213> ORGANISM: Homo sapiens

<400> SEQUENCE: 53
tcagagaaag ggttagggac g                                              21

<210> SEQ ID NO 54
<211> LENGTH: 21
<212> TYPE: DNA
<213> ORGANISM: Homo sapiens

<400> SEQUENCE: 54
gctgtggaat gcttaacatg g                                              21

<210> SEQ ID NO 55
<211> LENGTH: 25
<212> TYPE: DNA
<213> ORGANISM: Homo sapiens

<400> SEQUENCE: 55
ttctcaaatt tctagcatgg aagtg                                          25

<210> SEQ ID NO 56
<211> LENGTH: 22
<212> TYPE: DNA
<213> ORGANISM: Homo sapiens

<400> SEQUENCE: 56
cccaacacat ctcctaaacc tg                                             22

<210> SEQ ID NO 57
<211> LENGTH: 21
<212> TYPE: DNA
<213> ORGANISM: Homo sapiens

<400> SEQUENCE: 57
tgaggtttga cagagtcagc g                                              21

<210> SEQ ID NO 58
<211> LENGTH: 21
<212> TYPE: DNA
<213> ORGANISM: Homo sapiens

<400> SEQUENCE: 58
ttgaatgaac aggaaacagg g                                             21

<210> SEQ ID NO 59
<211> LENGTH: 21
<212> TYPE: DNA
<213> ORGANISM: Homo sapiens

<400> SEQUENCE: 59
cacagtcctc ctgtgttcca g                                             21

<210> SEQ ID NO 60
<211> LENGTH: 21
<212> TYPE: DNA
<213> ORGANISM: Homo sapiens

<400> SEQUENCE: 60
ttcactgcta cttgctgagc g                                             21

<210> SEQ ID NO 61
<211> LENGTH: 21
<212> TYPE: DNA
<213> ORGANISM: Homo sapiens

<400> SEQUENCE: 61
tcactgttgg gttgagacca g                                             21

<210> SEQ ID NO 62
<211> LENGTH: 21
<212> TYPE: DNA
<213> ORGANISM: Homo sapiens

<400> SEQUENCE: 62
tttgaatcga tgctgaacca g                                             21

<210> SEQ ID NO 63
<211> LENGTH: 21
<212> TYPE: DNA
<213> ORGANISM: Homo sapiens

<400> SEQUENCE: 63
gctttctttc agaggctgga g                                             21

<210> SEQ ID NO 64
<211> LENGTH: 21
<212> TYPE: DNA
<213> ORGANISM: Homo sapiens

<400> SEQUENCE: 64
ttggagtaaa tctgtccctg g                                             21

<210> SEQ ID NO 65
<211> LENGTH: 21
<212> TYPE: DNA
<213> ORGANISM: Homo sapiens

<400> SEQUENCE: 65
gaggttggtt tggatctttg g                                             21

<210> SEQ ID NO 66
<211> LENGTH: 25
<212> TYPE: DNA
<213> ORGANISM: Homo sapiens

<400> SEQUENCE: 66
agtttgcacc aacctaatat ttcac					25

<210> SEQ ID NO 67
<211> LENGTH: 22
<212> TYPE: DNA
<213> ORGANISM: Homo sapiens

<400> SEQUENCE: 67
gcaattcaga tagcctaggt gc					22

<210> SEQ ID NO 68
<211> LENGTH: 21
<212> TYPE: DNA
<213> ORGANISM: Homo sapiens

<400> SEQUENCE: 68
tatggctgct tctgtcactg g					21

<210> SEQ ID NO 69
<211> LENGTH: 21
<212> TYPE: DNA
<213> ORGANISM: Homo sapiens

<400> SEQUENCE: 69
tgcgtctcat aaactgcaag g					21

<210> SEQ ID NO 70
<211> LENGTH: 20
<212> TYPE: DNA
<213> ORGANISM: Homo sapiens

<400> SEQUENCE: 70
gtgaggtctg ggaatggtgg					20

<210> SEQ ID NO 71
<211> LENGTH: 21
<212> TYPE: DNA
<213> ORGANISM: Homo sapiens

<400> SEQUENCE: 71
tcaggatgaa tgtggtcatg c					21

<210> SEQ ID NO 72
<211> LENGTH: 21
<212> TYPE: DNA
<213> ORGANISM: Homo sapiens

<400> SEQUENCE: 72
aaagttggta ttggaccctg g					21

<210> SEQ ID NO 73
<211> LENGTH: 21
<212> TYPE: DNA
<213> ORGANISM: Homo sapiens

<400> SEQUENCE: 73
agactcagcc aaggcaaaga g					21

<210> SEQ ID NO 74
<211> LENGTH: 18
<212> TYPE: DNA
<213> ORGANISM: Homo sapiens

<400> SEQUENCE: 74
gacccagcgc taaccagg                                                    18

<210> SEQ ID NO 75
<211> LENGTH: 21
<212> TYPE: DNA
<213> ORGANISM: Homo sapiens

<400> SEQUENCE: 75
acccatccac tttgaggaca c                                                21

<210> SEQ ID NO 76
<211> LENGTH: 23
<212> TYPE: DNA
<213> ORGANISM: Homo sapiens

<400> SEQUENCE: 76
aagagcacat ttacacagcc ttg                                              23

<210> SEQ ID NO 77
<211> LENGTH: 20
<212> TYPE: DNA
<213> ORGANISM: Homo sapiens

<400> SEQUENCE: 77
cccagcattc cttcaaagac                                                  20

<210> SEQ ID NO 78
<211> LENGTH: 26
<212> TYPE: DNA
<213> ORGANISM: Homo sapiens

<400> SEQUENCE: 78
ggattattca gtatcaacgt ttgaag                                           26

<210> SEQ ID NO 79
<211> LENGTH: 21
<212> TYPE: DNA
<213> ORGANISM: Homo sapiens

<400> SEQUENCE: 79
aacagccact gaccaagaag g                                                21

<210> SEQ ID NO 80
<211> LENGTH: 21
<212> TYPE: DNA
<213> ORGANISM: Homo sapiens

<400> SEQUENCE: 80
ggcaaacttc agaaagcatt g                                                21

<210> SEQ ID NO 81
<211> LENGTH: 21
<212> TYPE: DNA
<213> ORGANISM: Homo sapiens

<400> SEQUENCE: 81
cagggaatgg aatcaactgt g                                                21

<210> SEQ ID NO 82
<211> LENGTH: 21
<212> TYPE: DNA
<213> ORGANISM: Homo sapiens

```
<400> SEQUENCE: 82
ttcctcgaca catacaccct c                                              21

<210> SEQ ID NO 83
<211> LENGTH: 21
<212> TYPE: DNA
<213> ORGANISM: Homo sapiens

<400> SEQUENCE: 83
ttcccaccct tagacacctt g                                              21

<210> SEQ ID NO 84
<211> LENGTH: 22
<212> TYPE: DNA
<213> ORGANISM: Homo sapiens

<400> SEQUENCE: 84
tgttattagg gctcagccac ac                                             22

<210> SEQ ID NO 85
<211> LENGTH: 22
<212> TYPE: DNA
<213> ORGANISM: Homo sapiens

<400> SEQUENCE: 85
tgagtcatta aatcatgtgg ca                                             22

<210> SEQ ID NO 86
<211> LENGTH: 23
<212> TYPE: DNA
<213> ORGANISM: Homo sapiens

<400> SEQUENCE: 86
caaacatttc tgtgattcaa tgg                                            23

<210> SEQ ID NO 87
<211> LENGTH: 22
<212> TYPE: DNA
<213> ORGANISM: Homo sapiens

<400> SEQUENCE: 87
tctggaaagg catttcttta gg                                             22

<210> SEQ ID NO 88
<211> LENGTH: 21
<212> TYPE: DNA
<213> ORGANISM: Homo sapiens

<400> SEQUENCE: 88
tgaaagattg gttcctttcc g                                              21

<210> SEQ ID NO 89
<211> LENGTH: 20
<212> TYPE: DNA
<213> ORGANISM: Homo sapiens

<400> SEQUENCE: 89
ctctcaaacc taggcccacc                                                20

<210> SEQ ID NO 90
<211> LENGTH: 24
<212> TYPE: DNA
```

```
<213> ORGANISM: Homo sapiens

<400> SEQUENCE: 90
ccttaggaag gctttgcata ttag                                          24

<210> SEQ ID NO 91
<211> LENGTH: 21
<212> TYPE: DNA
<213> ORGANISM: Homo sapiens

<400> SEQUENCE: 91
ttcttatgca tggccttcaa c                                             21

<210> SEQ ID NO 92
<211> LENGTH: 21
<212> TYPE: DNA
<213> ORGANISM: Homo sapiens

<400> SEQUENCE: 92
ccaaagtagg cctgtaggct g                                             21

<210> SEQ ID NO 93
<211> LENGTH: 21
<212> TYPE: DNA
<213> ORGANISM: Homo sapiens

<400> SEQUENCE: 93
tcttcctctc cctggtcttc c                                             21

<210> SEQ ID NO 94
<211> LENGTH: 24
<212> TYPE: DNA
<213> ORGANISM: Homo sapiens

<400> SEQUENCE: 94
catgcctgta tcaataaatg gagt                                          24

<210> SEQ ID NO 95
<211> LENGTH: 21
<212> TYPE: DNA
<213> ORGANISM: Homo sapiens

<400> SEQUENCE: 95
catgggaaat ggaaagactc c                                             21

<210> SEQ ID NO 96
<211> LENGTH: 19
<212> TYPE: DNA
<213> ORGANISM: Homo sapiens

<400> SEQUENCE: 96
tttgtgttgc cactgctcc                                                19

<210> SEQ ID NO 97
<211> LENGTH: 21
<212> TYPE: DNA
<213> ORGANISM: Homo sapiens

<400> SEQUENCE: 97
tctgaaacac tcacaatggg c                                             21

<210> SEQ ID NO 98
<211> LENGTH: 21
```

```
<212> TYPE: DNA
<213> ORGANISM: Homo sapiens

<400> SEQUENCE: 98
gactgccttc cagtcaattc c                                              21

<210> SEQ ID NO 99
<211> LENGTH: 21
<212> TYPE: DNA
<213> ORGANISM: Homo sapiens

<400> SEQUENCE: 99
cccagatcca agaagaagga a                                              21

<210> SEQ ID NO 100
<211> LENGTH: 22
<212> TYPE: DNA
<213> ORGANISM: Homo sapiens

<400> SEQUENCE: 100
ccttcaatcg gtttctaatt gc                                             22

<210> SEQ ID NO 101
<211> LENGTH: 27
<212> TYPE: DNA
<213> ORGANISM: Homo sapiens

<400> SEQUENCE: 101
tctaaagagc ttcatgatta cttgctc                                        27

<210> SEQ ID NO 102
<211> LENGTH: 21
<212> TYPE: DNA
<213> ORGANISM: Homo sapiens

<400> SEQUENCE: 102
tcttgaggtg aattattgcc g                                              21

<210> SEQ ID NO 103
<211> LENGTH: 21
<212> TYPE: DNA
<213> ORGANISM: Homo sapiens

<400> SEQUENCE: 103
atgagaggag agagggcttt g                                              21

<210> SEQ ID NO 104
<211> LENGTH: 21
<212> TYPE: DNA
<213> ORGANISM: Homo sapiens

<400> SEQUENCE: 104
ttccttacca atgaaagccc a                                              21

<210> SEQ ID NO 105
<211> LENGTH: 23
<212> TYPE: DNA
<213> ORGANISM: Homo sapiens

<400> SEQUENCE: 105
agaccatctg caacataagg agt                                            23

<210> SEQ ID NO 106
```

```
<211> LENGTH: 24
<212> TYPE: DNA
<213> ORGANISM: Homo sapiens

<400> SEQUENCE: 106
cagcctaaca catgtacctc catt                                              24

<210> SEQ ID NO 107
<211> LENGTH: 21
<212> TYPE: DNA
<213> ORGANISM: Homo sapiens

<400> SEQUENCE: 107
agaagctttc cttgatgacc c                                                 21

<210> SEQ ID NO 108
<211> LENGTH: 22
<212> TYPE: DNA
<213> ORGANISM: Homo sapiens

<400> SEQUENCE: 108
ttcccatctc aatccttgat ta                                                22

<210> SEQ ID NO 109
<211> LENGTH: 22
<212> TYPE: DNA
<213> ORGANISM: Homo sapiens

<400> SEQUENCE: 109
tgaggcaacc tgaaatctaa cc                                                22

<210> SEQ ID NO 110
<211> LENGTH: 29
<212> TYPE: DNA
<213> ORGANISM: Homo sapiens

<400> SEQUENCE: 110
cagaaagtaa atcaagagag agataggac                                         29

<210> SEQ ID NO 111
<211> LENGTH: 21
<212> TYPE: DNA
<213> ORGANISM: Homo sapiens

<400> SEQUENCE: 111
aatgcattga tggtgcttca g                                                 21

<210> SEQ ID NO 112
<211> LENGTH: 22
<212> TYPE: DNA
<213> ORGANISM: Homo sapiens

<400> SEQUENCE: 112
caagcccaaa gaagaagaga ag                                                22

<210> SEQ ID NO 113
<211> LENGTH: 25
<212> TYPE: DNA
<213> ORGANISM: Homo sapiens

<400> SEQUENCE: 113
ttgctttcaa tcatacttct atccc                                             25
```

```
<210> SEQ ID NO 114
<211> LENGTH: 25
<212> TYPE: DNA
<213> ORGANISM: Homo sapiens

<400> SEQUENCE: 114
tctgattacc ttgctaatct tggtg                                     25

<210> SEQ ID NO 115
<211> LENGTH: 21
<212> TYPE: DNA
<213> ORGANISM: Homo sapiens

<400> SEQUENCE: 115
gaagcctgtt gctgtgaagt g                                         21

<210> SEQ ID NO 116
<211> LENGTH: 22
<212> TYPE: DNA
<213> ORGANISM: Homo sapiens

<400> SEQUENCE: 116
gggatggata tgggtaagga tg                                        22

<210> SEQ ID NO 117
<211> LENGTH: 21
<212> TYPE: DNA
<213> ORGANISM: Homo sapiens

<400> SEQUENCE: 117
cacaggaggt aggagtgagg g                                         21

<210> SEQ ID NO 118
<211> LENGTH: 20
<212> TYPE: DNA
<213> ORGANISM: Homo sapiens

<400> SEQUENCE: 118
tttggccctc tttgactttg                                           20

<210> SEQ ID NO 119
<211> LENGTH: 21
<212> TYPE: DNA
<213> ORGANISM: Homo sapiens

<400> SEQUENCE: 119
gtccacgtcc ctaacccttt c                                         21

<210> SEQ ID NO 120
<211> LENGTH: 22
<212> TYPE: DNA
<213> ORGANISM: Homo sapiens

<400> SEQUENCE: 120
tcctggatgg acaatgtaaa cc                                        22

<210> SEQ ID NO 121
<211> LENGTH: 20
<212> TYPE: DNA
<213> ORGANISM: Homo sapiens

<400> SEQUENCE: 121
gcaggaacct gctgacaatc                                           20
```

```
<210> SEQ ID NO 122
<211> LENGTH: 25
<212> TYPE: DNA
<213> ORGANISM: Homo sapiens

<400> SEQUENCE: 122
aaagcatttg aagaattcta ccctc                                          25

<210> SEQ ID NO 123
<211> LENGTH: 24
<212> TYPE: DNA
<213> ORGANISM: Homo sapiens

<400> SEQUENCE: 123
tctgcacaat ttaattaagg accc                                           24

<210> SEQ ID NO 124
<211> LENGTH: 21
<212> TYPE: DNA
<213> ORGANISM: Homo sapiens

<400> SEQUENCE: 124
cttccttggc ctgtatccca c                                              21

<210> SEQ ID NO 125
<211> LENGTH: 24
<212> TYPE: DNA
<213> ORGANISM: Homo sapiens

<400> SEQUENCE: 125
gattgcttat gggtaatgat ttgg                                           24

<210> SEQ ID NO 126
<211> LENGTH: 20
<212> TYPE: DNA
<213> ORGANISM: Homo sapiens

<400> SEQUENCE: 126
gcttcctctt catgcgtcag                                                20

<210> SEQ ID NO 127
<211> LENGTH: 21
<212> TYPE: DNA
<213> ORGANISM: Homo sapiens

<400> SEQUENCE: 127
aaccgtgggt gagttatagc c                                              21

<210> SEQ ID NO 128
<211> LENGTH: 22
<212> TYPE: DNA
<213> ORGANISM: Homo sapiens

<400> SEQUENCE: 128
tgtagcgcag catgtattca ac                                             22

<210> SEQ ID NO 129
<211> LENGTH: 19
<212> TYPE: DNA
<213> ORGANISM: Homo sapiens

<400> SEQUENCE: 129
ccacatccca tgtcatccc                                                 19
```

```
<210> SEQ ID NO 130
<211> LENGTH: 18
<212> TYPE: DNA
<213> ORGANISM: Homo sapiens

<400> SEQUENCE: 130
ctcgtgatcc gcccatct                                                 18

<210> SEQ ID NO 131
<211> LENGTH: 20
<212> TYPE: DNA
<213> ORGANISM: Homo sapiens

<400> SEQUENCE: 131
cctttcccaa atcttggagc                                               20

<210> SEQ ID NO 132
<211> LENGTH: 21
<212> TYPE: DNA
<213> ORGANISM: Homo sapiens

<400> SEQUENCE: 132
tagctatgtg gctatggctg c                                             21

<210> SEQ ID NO 133
<211> LENGTH: 20
<212> TYPE: DNA
<213> ORGANISM: Homo sapiens

<400> SEQUENCE: 133
gggagagcag gacttgtgag                                               20

<210> SEQ ID NO 134
<211> LENGTH: 20
<212> TYPE: DNA
<213> ORGANISM: Homo sapiens

<400> SEQUENCE: 134
aaccgtaaca agtccgtggg                                               20

<210> SEQ ID NO 135
<211> LENGTH: 17
<212> TYPE: DNA
<213> ORGANISM: Inovirus eterobacteria phage M13

<400> SEQUENCE: 135
gtaaaacgac ggccagt                                                  17
```